US012371498B2

(12) United States Patent
Frendéus et al.

(10) Patent No.: US 12,371,498 B2
(45) Date of Patent: Jul. 29, 2025

(54) COMBINATION AND USE OF ANTIBODIES

(71) Applicants: BIOINVENT INTERNATIONAL AB, Lund (SE); UNIVERSITY OF SOUTHAMPTON, Southampton (GB)

(72) Inventors: Björn Frendéus, Lund (SE); Ingrid Teige, Lund (SE); Linda Mårtensson, Bjärred (SE); Mark Cragg, Southampton (GB); Stephen Beers, Southampton (GB); Ali Roghanian, Southampton (GB); Robert Oldham, Southampton (GB)

(73) Assignees: BIOVENT INTERNATIONAL AB, Lund (SE); UNIVERSITY OF SOUTHAMPTON, Southampton (GB)

( * ) Notice: Subject to any disclaimer, the term of this patent is extended or adjusted under 35 U.S.C. 154(b) by 1253 days.

(21) Appl. No.: 16/959,425

(22) PCT Filed: Jan. 10, 2019

(86) PCT No.: PCT/EP2019/050566
§ 371 (c)(1),
(2) Date: Jun. 30, 2020

(87) PCT Pub. No.: WO2019/138005
PCT Pub. Date: Jul. 18, 2019

(65) Prior Publication Data
US 2020/0362036 A1 Nov. 19, 2020

(30) Foreign Application Priority Data

Jan. 10, 2018 (GB) ...................... 1800395
Jan. 11, 2018 (GB) ...................... 1800461

(51) Int. Cl.
*C07K 16/28* (2006.01)
*A61P 35/00* (2006.01)

(52) U.S. Cl.
CPC ............ *C07K 16/283* (2013.01); *A61P 35/00* (2018.01); *C07K 16/28* (2013.01); *C07K 2317/54* (2013.01); *C07K 2317/55* (2013.01); *C07K 2317/569* (2013.01)

(58) Field of Classification Search
CPC .......... A61K 2039/507; C07K 2317/76; C07K 16/283; C07K 2317/71; C07K 2317/54; C07K 2317/55
See application file for complete search history.

(56) References Cited

U.S. PATENT DOCUMENTS

2015/0344575 A1* 12/2015 Koenig ............ A61K 39/3955 424/143.1
2016/0145336 A1  5/2016 Francis et al.
2017/0107293 A1* 4/2017 Frendéus ................ A61P 43/00

FOREIGN PATENT DOCUMENTS

| EP | 0 605 442 B1 | 4/2003 |
|---|---|---|
| GB | 2 526 139 A | 11/2015 |
| WO | 2006/073921 A2 | 7/2006 |
| WO | 2008/002933 A2 | 1/2008 |
| WO | 2015/173384 A1 | 11/2015 |
| WO | 2017/089334 A1 | 6/2017 |
| WO | 2017/103895 A1 | 6/2017 |
| WO | 2017/174331 A1 | 10/2017 |

OTHER PUBLICATIONS

Sfanos et al (Clinical Cancer Research, 2008, vol. 14, pp. 3254-3261) (Year: 2008).*
Barbee and Horvat (Annals of Pharmacotherapy, 2015, vol. 49, pp. 907-937) (Year: 2015).*
Beers et al., "Antigenic modulation limits the efficacy of anti-CD20 antibodies: implications for antibody selection" Blood, 115(25):5191-201 (2010).
Beers et al., "Type II (tositumomab) anti-CD20 monoclonal antibody out performs type I (rituximab-like) reagents in B-cell depletion regardless of complement activation" Blood, 112(10):4170-4177 (2008).
Bianchi et al., "High level expression and rational mutagenesis of a designed protein, the minibody: From an insoluble to a soluble molecule" J. Mol. Biol., 236(2): 649-59 (1994).
Buchan et al., "The immunobiology of CD27 and OX40 and their potential as targets for cancer immunotherapy", Blood, 131:39-48 (2018).
Cleary et al., "Antibody Distance from the Cell Membrane Regulates Antibody Effector Mechanisms" J Immunol, 198:3999-4011 (2017).
Clynes et al., "Inhibitory Fc receptors modulate in vivo cytotoxicity against tumor targets", Nat Med, 6:443-446 (2000).
Dahal et al., "FcγR requirements leading to successful immunotherapy", Immunol Rev., 268(1):104-122 (2015).
Gao et al., "Molecular Cloning of a Proteolytic Antibody Light Chain", J. Biol. Chem., 269(51):32389-32393 (1994).

(Continued)

*Primary Examiner* — Karen A. Canella
(74) *Attorney, Agent, or Firm* — Fuller IP Law LLC; Rodney J. Fuller

(57) ABSTRACT

Described is the use of a first antibody molecule that specifically binds FcγRIIb via its Fab region, but lacks Fc region or has reduced binding to Fcγ receptors via its Fc region, for use in combination with a second antibody molecule that specifically binds to a receptor present on an immune cell, wherein the immune cell is an immune cell that suppresses anti-cancer immunity, which second antibody molecule has an Fc region that binds to at least one activating Fcγ receptor, and wherein the binding of the second antibody molecule to the receptor on the immune cell causes depletion and/or deactivation of the immune cell in the treatment of an FcγRIIb-negative cancer in a patient, as well as pharmaceutical compositions and kits comprising these to antibody molecules, and methods of treating cancer using these two antibodies.

16 Claims, 25 Drawing Sheets

Specification includes a Sequence Listing.

(56) References Cited

OTHER PUBLICATIONS

Glennie et al., "Preparation and performance of bispecific F(ab' gamma)2 antibody containing thioether-linked Fab' gamma fragments", J Immunol., 139(7):2367-2375 (1987).
Greenman et al., "A controlled clinical trial of E5 murine monoclonal IgM antibody to endotoxin in the treatment of gram-negative sepsis. The XOMA Sepsis Study Group", JAMA, 266(8):1097-1102 (1991).
Heap et al., "Analysis of a 17-amino acid residue, virus-neutralizing microantibody", J. Gen. Virol., 86:1791-1800 (2005).
Hogarth, PM, "Fc Receptors: Introduction" Immunological Reviews, 268:1-5 (2015).
Ladner, "Antibodies cut down to size", Nature Biotechnology, 25:875-877 (2007).
Laune et al., "Systematic exploration of the antigen binding activity of synthetic peptides isolated from the variable regions of immunoglobulins" JBC, 272:30937-30944 (1997).
Monnet et al., "Synthetic peptides derived from the variable regions of an anti-CD4 monoclonal antibody bind to CD4 and inhibit HIV-1 promoter activation in virus-infected cells", JBC, 274: 3789-3796 (1999).
Montfoort et al., "Fcγ Receptor IIb Strongly Regulates Fcγ Receptor-Facilitated T Cell Activation by Dendritic Cells" J Immunol., 189(1):92-101 (2012).
Nicaise et al., "Affinity transfer by CDR grafting on a nonimmunoglobulin scaffold", Protein Science, 13(7):1882-1891 (2004).
Nimmerjahn et al., "Divergent immunoglobulin g subclass activity through selective Fc receptor binding", Science, 310(5753):1510-1512 (2005).
Pessi et al., "A designed metal-binding protein with a novel fold", Nature, 362:367-369 (1993).
Qiu et al., "Small antibody mimetics comprising two complementarity-determining regions and a framework region for tumor targeting", Nature Biotechnology, 25:921-929 (2007).
Quiocho et al., "Protein engineering. Making of the minibody", Nature, 362:293-294 (1993).
Roghanian et al., "Antagonistic Human FcγRIIB (CD32B) Antibodies Have Anti-Tumor Activity and Overcome Resistance to Antibody Therapy In Vivo", Cancer Cell, 27:473-488 (2015).
Roghanian et al., "Filament-associated TSGA10 protein is expressed in professional antigen presenting cells and Interacts with vimentin", Cell Immunol., 265(2):120-126 (2010).
Rozan et al., "Single-Domain Antibody-Based and Linker-Free Bispecific Antibodies Targeting FcγRIII Induce Potent Antitumor Activity without Recruiting Regulatory T Cells", Mol Cancer Ther., 12(8):1481-1491 (2013).
Stopforth et al., "Regulation of Monoclonal Antibody Immunotherapy by FcγRIIB", J. Clin. Immunol., 36:S88-94 (2016).
Tipton et al., "Antigenic modulation limits the effector cell mechanisms employed by type I anti-CD20 monoclonal antibodies", Blood, 125:1901-1909 (2015).
Tutt et al., "Development and Characterization of Monoclonal Antibodies Specific for Mouse and Human Fcγ Receptors", J. Immunol., 195(11):5503-5516 (2015).
Tutt et al., "Monoclonal Antibody Therapy of B Cell Lymphoma: Signaling Activity on Tumor Cells Appears More Important Than Recruitment of Effectors" J Immunol., 161(6):3176-3185 (1998).
Vaughan & Sollazzo, "Of Minibody, Camel and Bacteriophage", Combinatorial Chemistry & High Throughput Screening, 4(5):417-430 (2001).
Williams et al., "Development and characterisation of monoclonal antibodies specific for the murine inhibitory FcgammaRIIB (CD32B)", Eur J Immunol., 42(8):2109-2120 (2012).
Williams et al., "Immunotherapy Targeting Inhibitory Fcγ Receptor IIB (CD32b) in the Mouse Is Limited by Monoclonal Antibody Consumption and Receptor Internalization", J Immunol., 191(8):4130-4140 (2013).
Selby, Mark J. et al., "Anti-CTLA-4 Antibodies of IgG2a Isotype Enhance Antitumor Activity through Reduction of Intratumoral Regulatory T Cells", Cancer Immunology Research, 1(1):32-42 (Apr. 7, 2013).
Dahan, Rony et al., "Fc[gamma]Rs Modulate the Anti-tumor Activity of Antibodies Targeting the PD-1/PD-L1 Axis", Cancer Cell, 28(3):285-295 (Sep. 14, 2015).
Hamilton, G. et al., "Avelumab: combining immune checkpoint inhibition and antibody-dependent cytotoxicity", Expert Opinion on Biological Therapy, 17(4):515-523 (Feb. 22, 2017).
Arce Vargas, Frederick et al., "Fc-Optimized Anti-CD25 Depletes Tumor-Infiltrating Regulatory T Cells and Synergizes with PD-1 Blockade to Eradicate Established Tumors", 46(4):577-586 (Apr. 1, 2017).
Teige, Ingrid et al., "Targeting the Antibody Checkpoints to Enhance Cancer Immunotherapy-Focus on Fc[gamma] RIIB", Frontiers in Immunology, vol. 10, pp. 1-14 (Mar. 12, 2019).
Arce Vargas, Frederick et al., "Fc Effector Function Contributes to the Activity of Human Anti-CTLA-4 Antibodies", Cancer Cell, 33(4):649-663 (Mar. 22, 2018).
Buchan, Sarah L. et al., "Antibodies to Costimulatory Receptor 4-1BB Enhance Anti-tumor Immunity via T Regulatory Cell Depletion and Promotion of CD8 T Cell Effector Function", Immunity, 49:1-13 (Nov. 20, 2018).
Zak, K.M., et al. "Structural Biology of the Immune Checkpoint Receptor PD-1 and Its Ligands PD-L1/PD-L2," Structure, 2017, 25(8), 1163-1174.
Kim, H.R., et al., "PD-L1 expression on immune cells, but not on tumor cells, is a favorable prognostic factor for head and neck cancer patients," Sci. Rep., 2016, 6:36956.

* cited by examiner

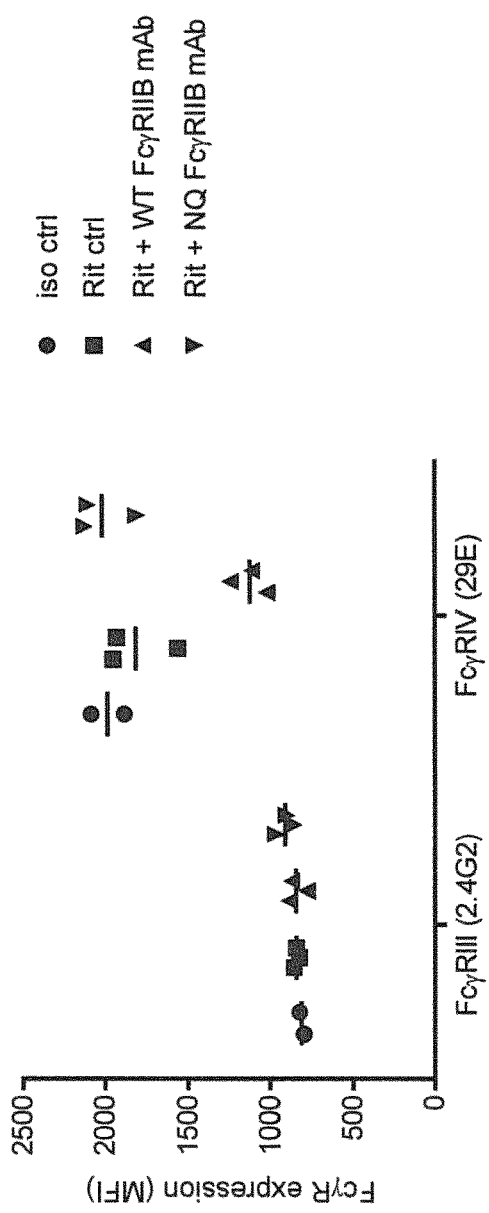
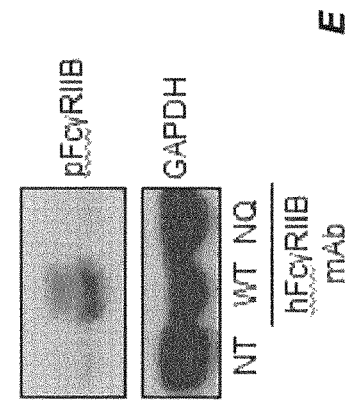
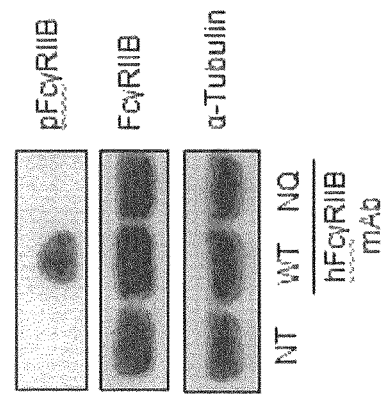
*Fig. 2, cont.*

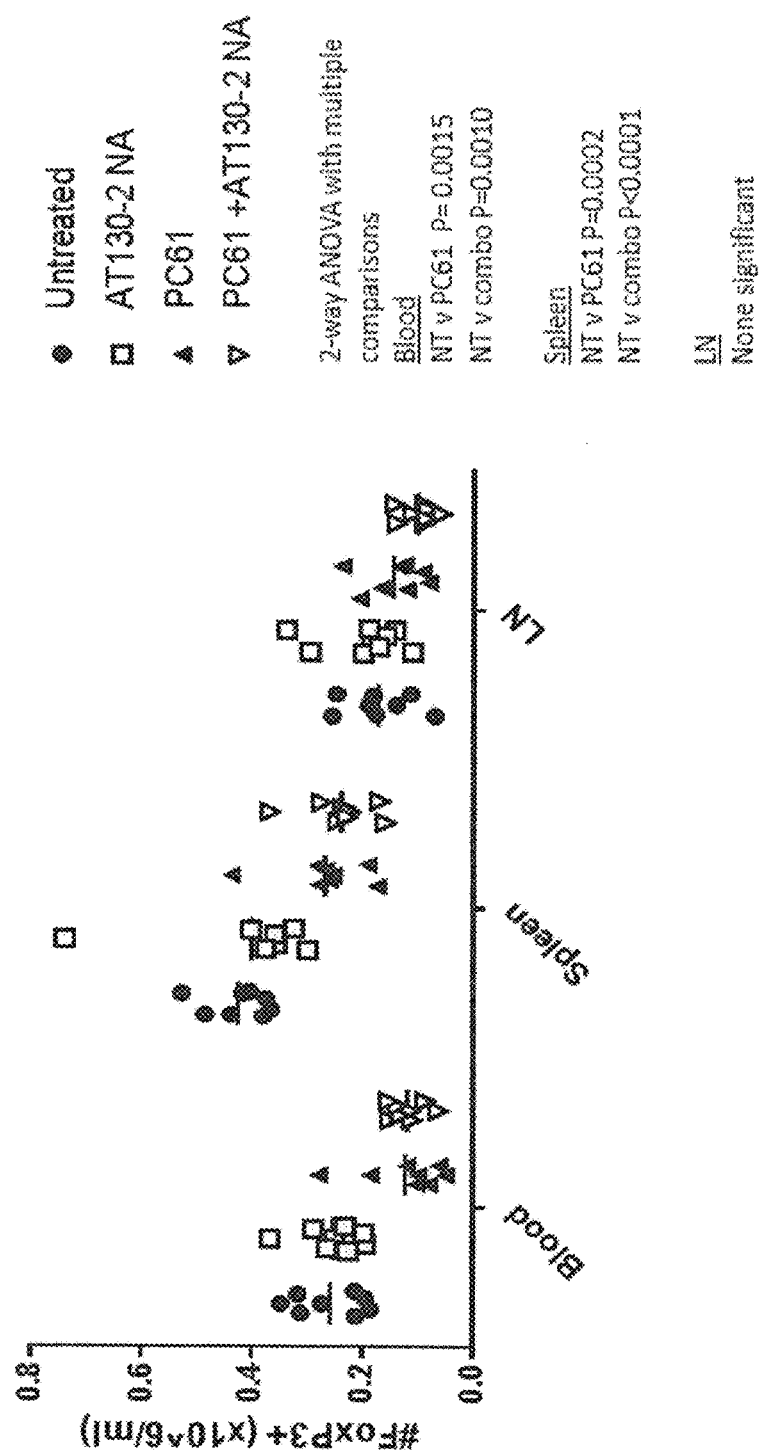

• AT130-2 NA delivers more favourable CD8:Treg ratios in the blood, spleen and LN

SEQUENCE LISTING

<160> NUMBER OF SEQ ID NOS: 197

<210> SEQ ID NO 1

```
<211> LENGTH: 330
<212> TYPE: PRT
<213> ORGANISM: Homo sapiens

<400> SEQUENCE: 1

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 2
<211> LENGTH: 105
<212> TYPE: PRT
<213> ORGANISM: Homo sapiens

<400> SEQUENCE: 2

Gln Pro Lys Ala Ala Pro Ser Val Thr Leu Phe Pro Pro Ser Ser Glu
1               5                   10                  15
```

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
            35                  40                  45

Lys Ala Gly Val Glu Thr Thr Thr Pro Ser Lys Gln Ser Asn Asn Lys
50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105

<210> SEQ ID NO 3
<211> LENGTH: 118
<212> TYPE: PRT
<213> ORGANISM: Homo sapiens

<400> SEQUENCE: 3

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Asn Trp Ile Arg Gln Thr Pro Gly Lys Gly Leu Glu Trp Val
            35                  40                  45

Ser Leu Ile Gly Trp Asp Gly Gly Ser Thr Tyr Tyr Ala Asp Ser Val
50                  55                  60

Lys Gly Arg Phe Thr Ile Ser Arg Asp Asn Ser Glu Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Tyr Ser Gly Tyr Glu Leu Asp Tyr Trp Gly Gln Gly Thr
            100                 105                 110

Leu Val Thr Val Ser Ser
        115

<210> SEQ ID NO 4
<211> LENGTH: 117
<212> TYPE: PRT
<213> ORGANISM: Homo sapiens

<400> SEQUENCE: 4

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Phe Thr Arg Tyr Asp Gly Ser Asn Lys Tyr Tyr Ala Asp Ser Val
        50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Asn Ile Asp Ala Phe Asp Val Trp Gly Gln Gly Thr Leu
            100                 105                 110

```
Val Thr Val Ser Ser
        115
```

<210> SEQ ID NO 5
<211> LENGTH: 122
<212> TYPE: PRT
<213> ORGANISM: Homo sapiens

<400> SEQUENCE: 5

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Ser Asp Ser Gly Ala Gly Arg Tyr Tyr Ala Asp Ser Val
    50                  55                  60

Glu Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr His Asp Ser Gly Glu Leu Leu Asp Ala Phe Asp Ile Trp
            100                 105                 110

Gly Gln Gly Thr Leu Val Thr Val Ser Ser
        115                 120
```

<210> SEQ ID NO 6
<211> LENGTH: 124
<212> TYPE: PRT
<213> ORGANISM: Homo sapiens

<400> SEQUENCE: 6

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Val Pro Gly Lys Gly Leu Glu Trp Val
        35                  40                  45

Ala Val Ile Ser Tyr Asp Gly Ser Asn Lys Asn Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Phe Asp Asn Ser Gly Tyr Ala Ile Pro Asp Ala Phe Asp
            100                 105                 110

Ile Trp Gly Gln Gly Thr Leu Val Thr Val Ser Ser
        115                 120
```

<210> SEQ ID NO 7
<211> LENGTH: 121
<212> TYPE: PRT
<213> ORGANISM: Homo sapiens

<400> SEQUENCE: 7

```
Glu Val Gln Leu Leu Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Ala Tyr Ile Ser Arg Asp Ala Asp Ile Thr His Tyr Pro Ala Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Thr Gly Phe Asp Tyr Ala Gly Asp Asp Ala Phe Asp Ile Trp Gly
            100                 105                 110

Gln Gly Thr Leu Val Thr Val Ser Ser
        115                 120

<210> SEQ ID NO 8
<211> LENGTH: 119
<212> TYPE: PRT
<213> ORGANISM: Homo sapiens

<400> SEQUENCE: 8

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
        35                  40                  45

Ala Leu Ile Gly His Asp Gly Asn Asn Lys Tyr Tyr Leu Asp Ser Leu
    50                  55                  60

Glu Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Thr Asp Ser Gly Tyr Asp Leu Leu Tyr Trp Gly Gln Gly
            100                 105                 110

Thr Leu Val Thr Val Ser Ser
        115

<210> SEQ ID NO 9
<211> LENGTH: 117
<212> TYPE: PRT
<213> ORGANISM: Homo sapiens

<400> SEQUENCE: 9

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Ala Ile Gly Phe Ser Asp Asp Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

Ala Gly Gly Asp Gly Ser Gly Trp Ser Phe Trp Gly Gln Gly Thr Leu
            100                 105                 110

Val Thr Val Ser Ser
        115

<210> SEQ ID NO 10
<211> LENGTH: 117
<212> TYPE: PRT
<213> ORGANISM: Homo sapiens

<400> SEQUENCE: 10

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Trp Arg Asp Ala Phe Asp Ile Trp Gly Gln Gly Thr Leu
            100                 105                 110

Val Thr Val Ser Ser
        115

<210> SEQ ID NO 11
<211> LENGTH: 117
<212> TYPE: PRT
<213> ORGANISM: Homo sapiens

<400> SEQUENCE: 11

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Asn Phe Asp Ala Phe Asp Val Trp Gly Gln Gly Thr Leu
            100                 105                 110

Val Thr Val Ser Ser
        115

<210> SEQ ID NO 12
<211> LENGTH: 117
<212> TYPE: PRT
<213> ORGANISM: Homo sapiens

<400> SEQUENCE: 12

Glu Val Gln Leu Leu Glu Ser Gly Gly Gly Leu Val Gln Pro Gly Gly

```
                1               5                   10                  15
            Ser Leu Arg Leu Ser Cys Ala Ala Ser Gly Phe Thr Phe Ser Thr Tyr
                        20                  25                  30

Gly Met His Trp Val Arg Gln Ala Pro Gly Lys Gly Leu Glu Trp Val
                        35                  40                  45

Ala Val Ile Ala Tyr Asp Gly Ser Lys Lys Asp Tyr Ala Asp Ser Val
                        50                  55                  60

Lys Gly Arg Phe Thr Ile Ser Arg Asp Asn Ser Lys Asn Thr Leu Tyr
             65                  70                  75                  80

Leu Gln Met Asn Ser Leu Arg Ala Glu Asp Thr Ala Val Tyr Tyr Cys
                        85                  90                  95

Ala Arg Glu Tyr Arg Asp Ala Phe Asp Ile Trp Gly Gln Gly Thr Leu
                        100                 105                 110

Val Thr Val Ser Ser
                        115

<210> SEQ ID NO 13
<211> LENGTH: 117
<212> TYPE: PRT
<213> ORGANISM: Homo sapiens

<400> SEQUENCE: 13

Glu Val Gln Leu Leu Glu Ser Gly Gly Gly Leu Val Gln Pro Gly Gly
             1               5                   10                  15

Ser Leu Arg Leu Ser Cys Ala Ala Ser Gly Phe Thr Phe Ser Ser Tyr
                        20                  25                  30

Gly Met His Trp Val Arg Gln Ala Pro Gly Lys Gly Leu Glu Trp Val
                        35                  40                  45

Ala Val Ile Ser Tyr Asp Gly Ile Asn Lys Asp Tyr Ala Asp Ser Met
                        50                  55                  60

Lys Gly Arg Phe Thr Ile Ser Arg Asp Asn Ser Lys Asn Thr Leu Tyr
             65                  70                  75                  80

Leu Gln Met Asn Ser Leu Arg Ala Glu Asp Thr Ala Val Tyr Tyr Cys
                        85                  90                  95

Ala Arg Glu Arg Lys Asp Ala Phe Asp Ile Trp Gly Gln Gly Thr Leu
                        100                 105                 110

Val Thr Val Ser Ser
                        115

<210> SEQ ID NO 14
<211> LENGTH: 117
<212> TYPE: PRT
<213> ORGANISM: Homo sapiens

<400> SEQUENCE: 14

Glu Val Gln Leu Leu Glu Ser Gly Gly Gly Leu Val Gln Pro Gly Gly
             1               5                   10                  15

Ser Leu Arg Leu Ser Cys Ala Ala Ser Gly Phe Thr Phe Asn Asn Tyr
                        20                  25                  30

Gly Met His Trp Val Arg Gln Ala Pro Gly Lys Gly Leu Glu Trp Val
                        35                  40                  45

Ala Val Ile Ser Tyr Asp Gly Ser Asn Arg Tyr Tyr Ala Asp Ser Val
                        50                  55                  60

Lys Gly Arg Phe Thr Met Ser Arg Asp Asn Ser Lys Asn Thr Leu Tyr
             65                  70                  75                  80

Leu Gln Met Asn Ser Leu Arg Ala Glu Asp Thr Ala Val Tyr Tyr Cys
```

```
                    85                  90                  95
Ala Arg Asp Arg Trp Asn Gly Met Asp Val Trp Gly Gln Gly Thr Leu
                100                 105                 110

Val Thr Val Ser Ser
        115

<210> SEQ ID NO 15
<211> LENGTH: 119
<212> TYPE: PRT
<213> ORGANISM: Homo sapiens

<400> SEQUENCE: 15

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asp Thr Ala Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp His Ser Val Ile Gly Ala Phe Asp Ile Trp Gly Gln Gly
                100                 105                 110

Thr Leu Val Thr Val Ser Ser
        115

<210> SEQ ID NO 16
<211> LENGTH: 119
<212> TYPE: PRT
<213> ORGANISM: Homo sapiens

<400> SEQUENCE: 16

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Thr Ser Tyr Asp Gly Asn Thr Lys Tyr Tyr Ala Asn Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Asp Cys Gly Gly Asp Cys Phe Asp Tyr Trp Gly Gln Gly
                100                 105                 110

Thr Leu Val Thr Val Ser Ser
        115

<210> SEQ ID NO 17
<211> LENGTH: 118
<212> TYPE: PRT
<213> ORGANISM: Homo sapiens

<400> SEQUENCE: 17
```

-continued

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gln Leu Gly Glu Ala Phe Asp Ile Trp Gly Gln Gly Thr
            100                 105                 110

Leu Val Thr Val Ser Ser
            115

<210> SEQ ID NO 18
<211> LENGTH: 117
<212> TYPE: PRT
<213> ORGANISM: Homo sapiens

<400> SEQUENCE: 18

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Ala Ile Ser Gly Ser Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Gly Gly Asp Ile Asp Tyr Phe Asp Tyr Trp Gly Gln Gly Thr Leu
            100                 105                 110

Val Thr Val Ser Ser
        115

<210> SEQ ID NO 19
<211> LENGTH: 117
<212> TYPE: PRT
<213> ORGANISM: Homo sapiens

<400> SEQUENCE: 19

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

```
Leu Gln Met Asn Ser Leu Arg Ala Glu Asp Thr Ala Val Tyr Tyr Cys
                85                  90                  95

Ala Arg Glu Arg Arg Asp Ala Phe Asp Ile Trp Gly Gln Gly Thr Leu
            100                 105                 110

Val Thr Val Ser Ser
        115

<210> SEQ ID NO 20
<211> LENGTH: 119
<212> TYPE: PRT
<213> ORGANISM: Homo sapiens

<400> SEQUENCE: 20

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Met Tyr Tyr Cys
                85                  90                  95

Ala Arg Asp His Ser Ala Ala Gly Tyr Phe Asp Tyr Trp Gly Gln Gly
            100                 105                 110

Thr Leu Val Thr Val Ser Ser
        115

<210> SEQ ID NO 21
<211> LENGTH: 119
<212> TYPE: PRT
<213> ORGANISM: Homo sapiens

<400> SEQUENCE: 21

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Ser Tyr
            20                  25                  30

Gly Met His Trp Val Arg Gln Ala Pro Gly Lys Gly Leu Glu Trp Val
        35                  40                  45

Ser Gly Ile Ser Trp Asp Ser Ala Ile Ile Asp Tyr Ala Gly Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Glu Ala Ala Ala Gly Ala Phe Asp Ile Trp Gly Gln Gly
            100                 105                 110

Thr Leu Val Thr Val Ser Ser
        115

<210> SEQ ID NO 22
<211> LENGTH: 121
<212> TYPE: PRT
<213> ORGANISM: Homo sapiens
```

<400> SEQUENCE: 22

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Leu Ser Ser Tyr
            20                  25                  30

Gly Ile Ser Trp Val Arg Gln Ala Pro Gly Lys Gly Leu Glu Trp Val
        35                  40                  45

Ser Gly Ile Ser Gly Ser Gly Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Ser Val Gly Ala Tyr Ala Asn Asp Ala Phe Asp Ile Trp Gly
            100                 105                 110

Gln Gly Thr Leu Val Thr Val Ser Ser
        115                 120

<210> SEQ ID NO 23
<211> LENGTH: 117
<212> TYPE: PRT
<213> ORGANISM: Homo sapiens

<400> SEQUENCE: 23

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Met
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Leu Tyr Asp Ala Phe Asp Ile Trp Gly Gln Gly Thr Leu
            100                 105                 110

Val Thr Val Ser Ser
        115

<210> SEQ ID NO 24
<211> LENGTH: 117
<212> TYPE: PRT
<213> ORGANISM: Homo sapiens

<400> SEQUENCE: 24

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Asn Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

```
Lys Gly Arg Phe Thr Ile Ser Lys Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Tyr Lys Asp Ala Phe Asp Ile Trp Gly Gln Gly Thr Leu
                100                 105                 110

Val Thr Val Ser Ser
            115

<210> SEQ ID NO 25
<211> LENGTH: 118
<212> TYPE: PRT
<213> ORGANISM: Homo sapiens

<400> SEQUENCE: 25

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
             35                  40                  45

Ala Val Ile Ser Tyr Asp Gly Ser Asn Lys Tyr Tyr Ala Asp Ser Val
         50                  55                  60

Lys Gly Arg Phe Thr Ile Ser Arg Asp Asn Ser Gln Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Phe Gly Tyr Ile Ile Leu Asp Tyr Trp Gly Gln Gly Thr
                100                 105                 110

Leu Val Thr Val Ser Ser
            115

<210> SEQ ID NO 26
<211> LENGTH: 117
<212> TYPE: PRT
<213> ORGANISM: Homo sapiens

<400> SEQUENCE: 26

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Asn His
                20                  25                  30

Gly Met His Trp Val Arg Gln Ala Pro Gly Lys Gly Leu Glu Trp Val
             35                  40                  45

Ala Val Ile Ser Tyr Asp Gly Thr Asn Lys Tyr Tyr Ala Asp Ser Val
         50                  55                  60

Arg Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Thr Trp Asp Ala Phe Asp Val Trp Gly Gln Gly Thr Leu
                100                 105                 110

Val Thr Val Ser Ser
            115

<210> SEQ ID NO 27
<211> LENGTH: 111
```

```
<212> TYPE: PRT
<213> ORGANISM: Homo sapiens

<400> SEQUENCE: 27

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Asn Asn
                20                  25                  30

Ala Val Asn Trp Tyr Gln Gln Leu Pro Gly Thr Ala Pro Lys Leu Leu
            35                  40                  45

Ile Tyr Asp Asn Asn Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Asn Ala Ser Ile Phe Gly Gly Gly Thr Lys Leu Thr Val Leu Gly
                100                 105                 110

<210> SEQ ID NO 28
<211> LENGTH: 111
<212> TYPE: PRT
<213> ORGANISM: Homo sapiens

<400> SEQUENCE: 28

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Asn Asn
                20                  25                  30

Ala Val Asn Trp Tyr Gln Gln Leu Pro Gly Thr Ala Pro Lys Leu Leu
            35                  40                  45

Ile Tyr Asp Asn Gln Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Glu Ala Trp Asp Asp Arg Leu
                85                  90                  95

Phe Gly Pro Val Phe Gly Gly Gly Thr Lys Leu Thr Val Leu Gly
                100                 105                 110

<210> SEQ ID NO 29
<211> LENGTH: 111
<212> TYPE: PRT
<213> ORGANISM: Homo sapiens

<400> SEQUENCE: 29

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
                20                  25                  30

His Val Leu Trp Tyr Gln Gln Leu Pro Gly Thr Ala Pro Lys Leu Leu
            35                  40                  45

Ile Tyr Gly Asn Ser Asn Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
```

-continued

```
                        85                  90                  95

Asn Gly Trp Val Phe Gly Gly Gly Thr Lys Leu Thr Val Leu Gly
            100                 105                 110

<210> SEQ ID NO 30
<211> LENGTH: 112
<212> TYPE: PRT
<213> ORGANISM: Homo sapiens

<400> SEQUENCE: 30

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Asp Asn Asn Ser Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Asp Ser
                85                  90                  95

Leu Gly Gly Pro Val Phe Gly Gly Gly Thr Lys Leu Thr Val Leu Gly
            100                 105                 110

<210> SEQ ID NO 31
<211> LENGTH: 112
<212> TYPE: PRT
<213> ORGANISM: Homo sapiens

<400> SEQUENCE: 31

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Ala Val Asn Trp Tyr Gln Gln Leu Pro Gly Thr Ala Pro Lys Leu Leu
        35                  40                  45

Ile Tyr Gly Asn Ser Asp Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Asn Gly Arg Trp Val Phe Gly Gly Gly Thr Lys Leu Thr Val Leu Gly
            100                 105                 110

<210> SEQ ID NO 32
<211> LENGTH: 111
<212> TYPE: PRT
<213> ORGANISM: Homo sapiens

<400> SEQUENCE: 32

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Asn Asn
            20                  25                  30

Ala Val Asn Trp Tyr Gln Gln Leu Pro Gly Thr Ala Pro Lys Leu Leu
        35                  40                  45
```

Ile Tyr Tyr Asp Asp Leu Leu Pro Ser Gly Val Pro Asp Arg Phe Ser
            50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Thr Thr Trp Asp Asp Ser Leu
                 85                  90                  95

Ser Gly Val Val Phe Gly Gly Gly Thr Lys Leu Thr Val Leu Gly
            100                 105                 110

<210> SEQ ID NO 33
<211> LENGTH: 111
<212> TYPE: PRT
<213> ORGANISM: Homo sapiens

<400> SEQUENCE: 33

Gln Ser Val Leu Thr Gln Pro Pro Ser Ala Ser Gly Thr Pro Gly Gln
 1               5                  10                  15

Arg Val Thr Ile Ser Cys Ser Gly Ser Ser Ser Asn Ile Gly Asn Asn
            20                  25                  30

Ala Val Asn Trp Tyr Gln Gln Leu Pro Gly Thr Ala Pro Lys Leu Leu
        35                  40                  45

Ile Tyr Asp Asn Asn Lys Arg Pro Ser Gly Val Pro Asp Arg Phe Ser
    50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Ala Thr Trp Asp Asp Ser Leu
                 85                  90                  95

Arg Gly Trp Val Phe Gly Gly Gly Thr Lys Leu Thr Val Leu Gly
            100                 105                 110

<210> SEQ ID NO 34
<211> LENGTH: 113
<212> TYPE: PRT
<213> ORGANISM: Homo sapiens

<400> SEQUENCE: 34

Gln Ser Val Leu Thr Gln Pro Pro Ser Ala Ser Gly Thr Pro Gly Gln
 1               5                  10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Ser Asp Asn Gln Arg Pro Ser Gly Val Pro Asp Arg Phe
    50                  55                  60

Ser Gly Ser Lys Ser Gly Thr Ser Ala Ser Leu Ala Ile Ser Gly Leu
 65                  70                  75                  80

Arg Ser Glu Asp Glu Ala Asp Tyr Tyr Cys Ala Ala Trp Asp Asp Ser
                 85                  90                  95

Leu Ser Gly Ser Trp Val Phe Gly Gly Gly Thr Lys Leu Thr Val Leu
            100                 105                 110

Gly

<210> SEQ ID NO 35
<211> LENGTH: 113
<212> TYPE: PRT
<213> ORGANISM: Homo sapiens

<400> SEQUENCE: 35

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Ser Asn Ser Gln Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Asp Ser
                85                  90                  95

Leu Asn Gly Gln Val Val Phe Gly Gly Gly Thr Lys Leu Thr Val Leu
            100                 105                 110

Gly

<210> SEQ ID NO 36
<211> LENGTH: 112
<212> TYPE: PRT
<213> ORGANISM: Homo sapiens

<400> SEQUENCE: 36

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Thr Ala Ser Leu Ala Ile Ser Gly Leu
65                  70                  75                  80

Arg Ser Glu Asp Glu Ala Asp Tyr Tyr Cys Ala Ala Trp Asp Asp Ser
                85                  90                  95

Val Ser Gly Trp Met Phe Gly Gly Gly Thr Lys Leu Thr Val Leu Gly
            100                 105                 110

<210> SEQ ID NO 37
<211> LENGTH: 112
<212> TYPE: PRT
<213> ORGANISM: Homo sapiens

<400> SEQUENCE: 37

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Ser Asn Asn Gln Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Thr Trp Asp Asp Ser
                85                  90                  95

```
Leu Asn Gly Leu Val Phe Gly Gly Gly Thr Lys Leu Thr Val Leu Gly
            100                 105                 110
```

<210> SEQ ID NO 38
<211> LENGTH: 113
<212> TYPE: PRT
<213> ORGANISM: Homo sapiens

<400> SEQUENCE: 38

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ala Gly
            20                  25                  30

Tyr Asp Val His Trp Tyr Gln Gln Leu Pro Gly Thr Ala Pro Lys Leu
            35                  40                  45

Leu Ile Tyr Ala Asn Asn Gln Arg Pro Ser Gly Val Pro Asp Arg Phe
        50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Asp Ser
                85                  90                  95

Leu Asn Gly Pro Trp Val Phe Gly Gly Gly Thr Lys Leu Thr Val Leu
            100                 105                 110

Gly
```

<210> SEQ ID NO 39
<211> LENGTH: 110
<212> TYPE: PRT
<213> ORGANISM: Homo sapiens

<400> SEQUENCE: 39

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
            35                  40                  45

Ile Tyr Asp Asn Asn Lys Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ser Ser Tyr Ala Gly Ser Asn
                85                  90                  95

Asn Val Val Phe Gly Gly Gly Thr Lys Leu Thr Val Leu Gly
            100                 105                 110
```

<210> SEQ ID NO 40
<211> LENGTH: 112
<212> TYPE: PRT
<213> ORGANISM: Homo sapiens

<400> SEQUENCE: 40

```
Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
```

```
                    35                  40                  45
Leu Ile Tyr Gly Asn Ser Asn Arg Pro Ser Gly Val Pro Asp Arg Phe
 50                  55                  60

Ser Gly Ser Lys Ser Gly Thr Ser Ala Ser Leu Ala Ile Ser Gly Leu
 65                  70                  75                  80

Arg Ser Glu Asp Glu Ala Asp Tyr Tyr Cys Ala Ala Trp Asp Asp Ser
                 85                  90                  95

Leu Asn Glu Gly Val Phe Gly Gly Gly Thr Lys Leu Thr Val Leu Gly
                100                 105                 110
```

<210> SEQ ID NO 41
<211> LENGTH: 112
<212> TYPE: PRT
<213> ORGANISM: Homo sapiens

<400> SEQUENCE: 41

```
Gln Ser Val Leu Thr Gln Pro Pro Ser Ala Ser Gly Thr Pro Gly Gln
  1               5                  10                  15

Arg Val Thr Ile Ser Cys Thr Gly Ser Ser Ser Asn Ile Gly Ala Gly
                 20                  25                  30

Tyr Asp Val His Trp Tyr Gln Gln Leu Pro Gly Thr Ala Pro Lys Leu
                 35                  40                  45

Leu Ile Tyr Asp Asn Asn Lys Arg Pro Ser Gly Val Pro Asp Arg Phe
 50                  55                  60

Ser Gly Ser Lys Ser Gly Thr Ser Ala Ser Leu Ala Ile Ser Gly Leu
 65                  70                  75                  80

Arg Ser Glu Asp Glu Ala Asp Tyr Tyr Cys Ala Thr Trp Asp Asp Ser
                 85                  90                  95

Leu Ser Gly Pro Val Phe Gly Gly Gly Thr Lys Leu Thr Val Leu Gly
                100                 105                 110
```

<210> SEQ ID NO 42
<211> LENGTH: 112
<212> TYPE: PRT
<213> ORGANISM: Homo sapiens

<400> SEQUENCE: 42

```
Gln Ser Val Leu Thr Gln Pro Pro Ser Ala Ser Gly Thr Pro Gly Gln
  1               5                  10                  15

Arg Val Thr Ile Ser Cys Thr Gly Ser Ser Ser Asn Phe Gly Ala Gly
                 20                  25                  30

Tyr Asp Val His Trp Tyr Gln Gln Leu Pro Gly Thr Ala Pro Lys Leu
                 35                  40                  45

Leu Ile Tyr Glu Asn Asn Lys Arg Pro Ser Gly Val Pro Asp Arg Phe
 50                  55                  60

Ser Gly Ser Lys Ser Gly Thr Ser Ala Ser Leu Ala Ile Ser Gly Leu
 65                  70                  75                  80

Arg Ser Glu Asp Glu Ala Asp Tyr Tyr Cys Ala Ala Trp Asp Asp Ser
                 85                  90                  95

Leu Asn Gly Pro Val Phe Gly Gly Gly Thr Lys Leu Thr Val Leu Gly
                100                 105                 110
```

<210> SEQ ID NO 43
<211> LENGTH: 110
<212> TYPE: PRT
<213> ORGANISM: Homo sapiens

<400> SEQUENCE: 43

Gln Ser Val Leu Thr Gln Pro Pro Ser Ala Ser Gly Thr Pro Gly Gln
1               5                   10                  15

Arg Val Thr Ile Ser Cys Thr Gly Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Ser Asp Asn Gln Arg Pro Ser Gly Val Pro Asp Arg Phe
50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Thr Trp Asp Ser Asp
                85                  90                  95

Thr Pro Val Phe Gly Gly Gly Thr Lys Leu Thr Val Leu Gly
            100                 105                 110

<210> SEQ ID NO 44
<211> LENGTH: 111
<212> TYPE: PRT
<213> ORGANISM: Homo sapiens

<400> SEQUENCE: 44

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Gly Asn Ser Ile Arg Pro Ser Gly Gly Pro Asp Arg Phe Ser
50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ser Trp Asp Asp Ser Leu
                85                  90                  95

Ser Ser Pro Val Phe Gly Gly Gly Thr Lys Leu Thr Val Leu Gly
            100                 105                 110

<210> SEQ ID NO 45
<211> LENGTH: 113
<212> TYPE: PRT
<213> ORGANISM: Homo sapiens

<400> SEQUENCE: 45

Gln Ser Val Leu Thr Gln Pro Pro Ser Ala Ser Gly Thr Pro Gly Gln
1               5                   10                  15

Arg Val Thr Ile Ser Cys Thr Gly Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Thr Asp Arg Pro Ser Gly Val Pro Asp Arg Phe
50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Asp Ser
                85                  90                  95

Leu Ser Gly Pro Val Val Phe Gly Gly Gly Thr Lys Leu Thr Val Leu
            100                 105                 110

Gly

<210> SEQ ID NO 46
<211> LENGTH: 112
<212> TYPE: PRT
<213> ORGANISM: Homo sapiens

<400> SEQUENCE: 46

Gln Ser Val Leu Thr Gln Pro Pro Ser Ala Ser Gly Thr Pro Gly Gln
1               5                   10                  15

Arg Val Thr Ile Ser Cys Thr Gly Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asp Thr Asn Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Ser
                85                  90                  95

Leu Asn Gly Pro Val Phe Gly Gly Gly Thr Lys Leu Thr Val Leu Gly
            100                 105                 110

<210> SEQ ID NO 47
<211> LENGTH: 112
<212> TYPE: PRT
<213> ORGANISM: Homo sapiens

<400> SEQUENCE: 47

Gln Ser Val Leu Thr Gln Pro Pro Ser Ala Ser Gly Thr Pro Gly Gln
1               5                   10                  15

Arg Val Thr Ile Ser Cys Thr Gly Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Ala Asp Asp His Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ser Trp Asp Ser
                85                  90                  95

Gln Arg Ala Val Ile Phe Gly Gly Gly Thr Lys Leu Thr Val Leu Gly
            100                 105                 110

<210> SEQ ID NO 48
<211> LENGTH: 109
<212> TYPE: PRT
<213> ORGANISM: Homo sapiens

<400> SEQUENCE: 48

Gln Ser Val Leu Thr Gln Pro Pro Ser Ala Ser Gly Thr Pro Gly Gln
1               5                   10                  15

Arg Val Thr Ile Ser Cys Thr Gly Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Asp Asn Asn Lys Arg Pro Ser Gly Val Pro Asp Arg Phe Ser

```
                50                  55                  60
Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Gln Ala Trp Gly Thr Gly Ile
                 85                  90                  95

Arg Val Phe Gly Gly Gly Thr Lys Leu Thr Val Leu Gly
            100                 105
```

<210> SEQ ID NO 49
<211> LENGTH: 111
<212> TYPE: PRT
<213> ORGANISM: Homo sapiens

<400> SEQUENCE: 49

```
Gln Ser Val Leu Thr Gln Pro Pro Ser Ala Ser Gly Thr Pro Gly Gln
  1               5                  10                  15

Arg Val Thr Ile Ser Cys Ser Gly Ser Ser Asn Ile Gly Ser Asn
                 20                  25                  30

Thr Val Asn Trp Tyr Gln Gln Leu Pro Gly Thr Ala Pro Lys Leu Leu
             35                  40                  45

Ile Tyr Arg Asp Tyr Glu Arg Pro Ser Gly Val Pro Asp Arg Phe Ser
 50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Met Ala Trp Asp Asp Ser Leu
                 85                  90                  95

Ser Gly Val Val Phe Gly Gly Gly Thr Lys Leu Thr Val Leu Gly
            100                 105                 110
```

<210> SEQ ID NO 50
<211> LENGTH: 109
<212> TYPE: PRT
<213> ORGANISM: Homo sapiens

<400> SEQUENCE: 50

```
Gln Ser Val Leu Thr Gln Pro Pro Ser Ala Ser Gly Thr Pro Gly Gln
  1               5                  10                  15

Arg Val Thr Ile Ser Cys Ser Gly Ser Ser Asn Ile Gly Ser Asn
                 20                  25                  30

Asn Ala Asn Trp Tyr Gln Gln Leu Pro Gly Thr Ala Pro Lys Leu Leu
             35                  40                  45

Ile Tyr Asp Asn Asn Lys Arg Pro Ser Gly Val Pro Asp Arg Phe Ser
 50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Gln Ala Trp Asp Ser Thr
                 85                  90                  95

Val Val Phe Gly Gly Gly Thr Lys Leu Thr Val Leu Gly
            100                 105
```

<210> SEQ ID NO 51
<211> LENGTH: 5
<212> TYPE: PRT
<213> ORGANISM: Homo sapiens

<400> SEQUENCE: 51

```
Asp Tyr Tyr Met Asn
 1               5
```

<210> SEQ ID NO 52
<211> LENGTH: 17
<212> TYPE: PRT
<213> ORGANISM: Homo sapiens

<400> SEQUENCE: 52

Leu Ile Gly Trp Asp Gly Gly Ser Thr Tyr Tyr Ala Asp Ser Val Lys
1               5                   10                  15
Gly

<210> SEQ ID NO 53
<211> LENGTH: 9
<212> TYPE: PRT
<213> ORGANISM: Homo sapiens

<400> SEQUENCE: 53

Ala Tyr Ser Gly Tyr Glu Leu Asp Tyr
1               5

<210> SEQ ID NO 54
<211> LENGTH: 13
<212> TYPE: PRT
<213> ORGANISM: Homo sapiens

<400> SEQUENCE: 54

Ser Gly Ser Ser Ser Asn Ile Gly Asn Asn Ala Val Asn
1               5                   10

<210> SEQ ID NO 55
<211> LENGTH: 7
<212> TYPE: PRT
<213> ORGANISM: Homo sapiens

<400> SEQUENCE: 55

Asp Asn Asn Asn Arg Pro Ser
1               5

<210> SEQ ID NO 56
<211> LENGTH: 11
<212> TYPE: PRT
<213> ORGANISM: Homo sapiens

<400> SEQUENCE: 56

Ala Ala Trp Asp Asp Ser Leu Asn Ala Ser Ile
1               5                   10

<210> SEQ ID NO 57
<211> LENGTH: 5
<212> TYPE: PRT
<213> ORGANISM: Homo sapiens

<400> SEQUENCE: 57

Ser Tyr Gly Met His
1               5

<210> SEQ ID NO 58
<211> LENGTH: 17
<212> TYPE: PRT
<213> ORGANISM: Homo sapiens

<400> SEQUENCE: 58

Phe Thr Arg Tyr Asp Gly Ser Asn Lys Tyr Tyr Ala Asp Ser Val Arg
1               5                   10                  15

Gly

<210> SEQ ID NO 59
<211> LENGTH: 8
<212> TYPE: PRT
<213> ORGANISM: Homo sapiens

<400> SEQUENCE: 59

Glu Asn Ile Asp Ala Phe Asp Val
1               5

<210> SEQ ID NO 60
<211> LENGTH: 13
<212> TYPE: PRT
<213> ORGANISM: Homo sapiens

<400> SEQUENCE: 60

Ser Gly Ser Ser Ser Asn Ile Gly Asn Asn Ala Val Asn
1               5                   10

<210> SEQ ID NO 61
<211> LENGTH: 7
<212> TYPE: PRT
<213> ORGANISM: Homo sapiens

<400> SEQUENCE: 61

Asp Asn Gln Gln Arg Pro Ser
1               5

<210> SEQ ID NO 62
<211> LENGTH: 9
<212> TYPE: PRT
<213> ORGANISM: Homo sapiens

<400> SEQUENCE: 62

Trp Asp Asp Arg Leu Phe Gly Pro Val
1               5

<210> SEQ ID NO 63
<211> LENGTH: 5
<212> TYPE: PRT
<213> ORGANISM: Homo sapiens

<400> SEQUENCE: 63

Ser Tyr Ala Met Ser
1               5

<210> SEQ ID NO 64
<211> LENGTH: 17
<212> TYPE: PRT
<213> ORGANISM: Homo sapiens

<400> SEQUENCE: 64

Ser Ile Ser Asp Ser Gly Ala Gly Arg Tyr Tyr Ala Asp Ser Val Glu
1               5                   10                  15

Gly

<210> SEQ ID NO 65
<211> LENGTH: 13
<212> TYPE: PRT
<213> ORGANISM: Homo sapiens

<400> SEQUENCE: 65

Thr His Asp Ser Gly Glu Leu Leu Asp Ala Phe Asp Ile
1               5                   10

<210> SEQ ID NO 66
<211> LENGTH: 13
<212> TYPE: PRT
<213> ORGANISM: Homo sapiens

<400> SEQUENCE: 66

Ser Gly Ser Ser Ser Asn Ile Gly Ser Asn His Val Leu
1               5                   10

<210> SEQ ID NO 67
<211> LENGTH: 7
<212> TYPE: PRT
<213> ORGANISM: Homo sapiens

<400> SEQUENCE: 67

Gly Asn Ser Asn Arg Pro Ser
1               5

<210> SEQ ID NO 68
<211> LENGTH: 11
<212> TYPE: PRT
<213> ORGANISM: Homo sapiens

<400> SEQUENCE: 68

Ala Ala Trp Asp Asp Ser Leu Asn Gly Trp Val
1               5                   10

<210> SEQ ID NO 69
<211> LENGTH: 5
<212> TYPE: PRT
<213> ORGANISM: Homo sapiens

<400> SEQUENCE: 69

Thr Tyr Ala Met Asn
1               5

<210> SEQ ID NO 70
<211> LENGTH: 17
<212> TYPE: PRT
<213> ORGANISM: Homo sapiens

<400> SEQUENCE: 70

Val Ile Ser Tyr Asp Gly Ser Asn Lys Asn Tyr Val Asp Ser Val Lys
1               5                   10                  15

Gly

<210> SEQ ID NO 71
<211> LENGTH: 15
<212> TYPE: PRT
<213> ORGANISM: Homo sapiens

<400> SEQUENCE: 71

Asn Phe Asp Asn Ser Gly Tyr Ala Ile Pro Asp Ala Phe Asp Ile
1               5                   10                  15

<210> SEQ ID NO 72
<211> LENGTH: 14
<212> TYPE: PRT
<213> ORGANISM: Homo sapiens

<400> SEQUENCE: 72

```
Thr Gly Ser Ser Ser Asn Ile Gly Ala Gly Tyr Asp Val His
1               5                   10

<210> SEQ ID NO 73
<211> LENGTH: 7
<212> TYPE: PRT
<213> ORGANISM: Homo sapiens

<400> SEQUENCE: 73

Asp Asn Asn Ser Arg Pro Ser
1               5

<210> SEQ ID NO 74
<211> LENGTH: 11
<212> TYPE: PRT
<213> ORGANISM: Homo sapiens

<400> SEQUENCE: 74

Ala Ala Trp Asp Asp Ser Leu Gly Gly Pro Val
1               5                   10

<210> SEQ ID NO 75
<211> LENGTH: 5
<212> TYPE: PRT
<213> ORGANISM: Homo sapiens

<400> SEQUENCE: 75

Asn Ala Trp Met Ser
1               5

<210> SEQ ID NO 76
<211> LENGTH: 17
<212> TYPE: PRT
<213> ORGANISM: Homo sapiens

<400> SEQUENCE: 76

Tyr Ile Ser Arg Asp Ala Asp Ile Thr His Tyr Pro Ala Ser Val Lys
1               5                   10                  15
Gly

<210> SEQ ID NO 77
<211> LENGTH: 12
<212> TYPE: PRT
<213> ORGANISM: Homo sapiens

<400> SEQUENCE: 77

Gly Phe Asp Tyr Ala Gly Asp Asp Ala Phe Asp Ile
1               5                   10

<210> SEQ ID NO 78
<211> LENGTH: 13
<212> TYPE: PRT
<213> ORGANISM: Homo sapiens

<400> SEQUENCE: 78

Ser Gly Ser Ser Ser Asn Ile Gly Ser Asn Ala Val Asn
1               5                   10

<210> SEQ ID NO 79
<211> LENGTH: 7
<212> TYPE: PRT
<213> ORGANISM: Homo sapiens

<400> SEQUENCE: 79
```

Gly Asn Ser Asp Arg Pro Ser
1               5

<210> SEQ ID NO 80
<211> LENGTH: 12
<212> TYPE: PRT
<213> ORGANISM: Homo sapiens

<400> SEQUENCE: 80

Ala Ala Trp Asp Asp Ser Leu Asn Gly Arg Trp Val
1               5                   10

<210> SEQ ID NO 81
<211> LENGTH: 5
<212> TYPE: PRT
<213> ORGANISM: Homo sapiens

<400> SEQUENCE: 81

Asp Tyr Tyr Met Ser
1               5

<210> SEQ ID NO 82
<211> LENGTH: 17
<212> TYPE: PRT
<213> ORGANISM: Homo sapiens

<400> SEQUENCE: 82

Leu Ile Gly His Asp Gly Asn Asn Lys Tyr Tyr Leu Asp Ser Leu Glu
1               5                   10                  15

Gly

<210> SEQ ID NO 83
<211> LENGTH: 10
<212> TYPE: PRT
<213> ORGANISM: Homo sapiens

<400> SEQUENCE: 83

Ala Thr Asp Ser Gly Tyr Asp Leu Leu Tyr
1               5                   10

<210> SEQ ID NO 84
<211> LENGTH: 13
<212> TYPE: PRT
<213> ORGANISM: Homo sapiens

<400> SEQUENCE: 84

Ser Gly Ser Ser Ser Asn Ile Gly Asn Asn Ala Val Asn
1               5                   10

<210> SEQ ID NO 85
<211> LENGTH: 7
<212> TYPE: PRT
<213> ORGANISM: Homo sapiens

<400> SEQUENCE: 85

Tyr Asp Asp Leu Leu Pro Ser
1               5

<210> SEQ ID NO 86
<211> LENGTH: 11
<212> TYPE: PRT
<213> ORGANISM: Homo sapiens

<400> SEQUENCE: 86

```
Thr Thr Trp Asp Asp Ser Leu Ser Gly Val Val
1               5                   10
```

<210> SEQ ID NO 87
<211> LENGTH: 5
<212> TYPE: PRT
<213> ORGANISM: Homo sapiens

<400> SEQUENCE: 87

```
Asp Tyr Tyr Met Ser
1               5
```

<210> SEQ ID NO 88
<211> LENGTH: 17
<212> TYPE: PRT
<213> ORGANISM: Homo sapiens

<400> SEQUENCE: 88

```
Ala Ile Gly Phe Ser Asp Asp Asn Thr Tyr Tyr Ala Asp Ser Val Lys
1               5                   10                  15

Gly
```

<210> SEQ ID NO 89
<211> LENGTH: 8
<212> TYPE: PRT
<213> ORGANISM: Homo sapiens

<400> SEQUENCE: 89

```
Gly Asp Gly Ser Gly Trp Ser Phe
1               5
```

<210> SEQ ID NO 90
<211> LENGTH: 13
<212> TYPE: PRT
<213> ORGANISM: Homo sapiens

<400> SEQUENCE: 90

```
Ser Gly Ser Ser Ser Asn Ile Gly Asn Asn Ala Val Asn
1               5                   10
```

<210> SEQ ID NO 91
<211> LENGTH: 7
<212> TYPE: PRT
<213> ORGANISM: Homo sapiens

<400> SEQUENCE: 91

```
Asp Asn Asn Lys Arg Pro Ser
1               5
```

<210> SEQ ID NO 92
<211> LENGTH: 11
<212> TYPE: PRT
<213> ORGANISM: Homo sapiens

<400> SEQUENCE: 92

```
Ala Thr Trp Asp Asp Ser Leu Arg Gly Trp Val
1               5                   10
```

<210> SEQ ID NO 93
<211> LENGTH: 5
<212> TYPE: PRT
<213> ORGANISM: Homo sapiens

<400> SEQUENCE: 93

Asn Tyr Gly Met His
1               5

<210> SEQ ID NO 94
<211> LENGTH: 17
<212> TYPE: PRT
<213> ORGANISM: Homo sapiens

<400> SEQUENCE: 94

Val Ile Ser Tyr Asp Gly Ser Asn Lys Tyr Tyr Ala Asp Ser Val Lys
1               5                   10                  15

Gly

<210> SEQ ID NO 95
<211> LENGTH: 7
<212> TYPE: PRT
<213> ORGANISM: Homo sapiens

<400> SEQUENCE: 95

Trp Arg Asp Ala Phe Asp Ile
1               5

<210> SEQ ID NO 96
<211> LENGTH: 14
<212> TYPE: PRT
<213> ORGANISM: Homo sapiens

<400> SEQUENCE: 96

Thr Gly Ser Ser Ser Asn Ile Gly Ala Gly Tyr Asp Val His
1               5                   10

<210> SEQ ID NO 97
<211> LENGTH: 7
<212> TYPE: PRT
<213> ORGANISM: Homo sapiens

<400> SEQUENCE: 97

Ser Asp Asn Gln Arg Pro Ser
1               5

<210> SEQ ID NO 98
<211> LENGTH: 12
<212> TYPE: PRT
<213> ORGANISM: Homo sapiens

<400> SEQUENCE: 98

Ala Ala Trp Asp Asp Ser Leu Ser Gly Ser Trp Val
1               5                   10

<210> SEQ ID NO 99
<211> LENGTH: 5
<212> TYPE: PRT
<213> ORGANISM: Homo sapiens

<400> SEQUENCE: 99

Thr Tyr Gly Met His
1               5

<210> SEQ ID NO 100
<211> LENGTH: 17
<212> TYPE: PRT
<213> ORGANISM: Homo sapiens

<400> SEQUENCE: 100

```
Val Ile Ser Tyr Asp Gly Ser Asn Lys Tyr Tyr Ala Asp Ser Val Lys
1               5                   10                  15
Gly
```

<210> SEQ ID NO 101
<211> LENGTH: 8
<212> TYPE: PRT
<213> ORGANISM: Homo sapiens

<400> SEQUENCE: 101

```
Glu Asn Phe Asp Ala Phe Asp Val
1               5
```

<210> SEQ ID NO 102
<211> LENGTH: 14
<212> TYPE: PRT
<213> ORGANISM: Homo sapiens

<400> SEQUENCE: 102

```
Thr Gly Ser Ser Ser Asn Ile Gly Ala Gly Tyr Asp Val His
1               5                   10
```

<210> SEQ ID NO 103
<211> LENGTH: 7
<212> TYPE: PRT
<213> ORGANISM: Homo sapiens

<400> SEQUENCE: 103

```
Ser Asn Ser Gln Arg Pro Ser
1               5
```

<210> SEQ ID NO 104
<211> LENGTH: 12
<212> TYPE: PRT
<213> ORGANISM: Homo sapiens

<400> SEQUENCE: 104

```
Ala Ala Trp Asp Asp Ser Leu Asn Gly Gln Val Val
1               5                   10
```

<210> SEQ ID NO 105
<211> LENGTH: 5
<212> TYPE: PRT
<213> ORGANISM: Homo sapiens

<400> SEQUENCE: 105

```
Thr Tyr Gly Met His
1               5
```

<210> SEQ ID NO 106
<211> LENGTH: 17
<212> TYPE: PRT
<213> ORGANISM: Homo sapiens

<400> SEQUENCE: 106

```
Val Ile Ala Tyr Asp Gly Ser Lys Lys Asp Tyr Ala Asp Ser Val Lys
1               5                   10                  15
Gly
```

<210> SEQ ID NO 107
<211> LENGTH: 8
<212> TYPE: PRT
<213> ORGANISM: Homo sapiens

```
<400> SEQUENCE: 107

Glu Tyr Arg Asp Ala Phe Asp Ile
1               5

<210> SEQ ID NO 108
<211> LENGTH: 14
<212> TYPE: PRT
<213> ORGANISM: Homo sapiens

<400> SEQUENCE: 108

Thr Gly Ser Ser Ser Asn Ile Gly Ala Gly Tyr Asp Val His
1               5                   10

<210> SEQ ID NO 109
<211> LENGTH: 7
<212> TYPE: PRT
<213> ORGANISM: Homo sapiens

<400> SEQUENCE: 109

Gly Asn Ser Asn Arg Pro Ser
1               5

<210> SEQ ID NO 110
<211> LENGTH: 11
<212> TYPE: PRT
<213> ORGANISM: Homo sapiens

<400> SEQUENCE: 110

Ala Ala Trp Asp Asp Ser Val Ser Gly Trp Met
1               5                   10

<210> SEQ ID NO 111
<211> LENGTH: 5
<212> TYPE: PRT
<213> ORGANISM: Homo sapiens

<400> SEQUENCE: 111

Ser Tyr Gly Met His
1               5

<210> SEQ ID NO 112
<211> LENGTH: 17
<212> TYPE: PRT
<213> ORGANISM: Homo sapiens

<400> SEQUENCE: 112

Val Ile Ser Tyr Asp Gly Ile Asn Lys Asp Tyr Ala Asp Ser Met Lys
1               5                   10                  15

Gly

<210> SEQ ID NO 113
<211> LENGTH: 8
<212> TYPE: PRT
<213> ORGANISM: Homo sapiens

<400> SEQUENCE: 113

Glu Arg Lys Asp Ala Phe Asp Ile
1               5

<210> SEQ ID NO 114
<211> LENGTH: 14
<212> TYPE: PRT
<213> ORGANISM: Homo sapiens
```

<210> SEQ ID NO 114
<211> LENGTH: 12
<212> TYPE: PRT
<213> ORGANISM: Homo sapiens

<400> SEQUENCE: 114

Thr Gly Ser Ser Ser Asn Ile Gly Ala Gly Tyr Asp Val His
1               5                   10

<210> SEQ ID NO 115
<211> LENGTH: 7
<212> TYPE: PRT
<213> ORGANISM: Homo sapiens

<400> SEQUENCE: 115

Ser Asn Asn Gln Arg Pro Ser
1               5

<210> SEQ ID NO 116
<211> LENGTH: 11
<212> TYPE: PRT
<213> ORGANISM: Homo sapiens

<400> SEQUENCE: 116

Ala Thr Trp Asp Asp Ser Leu Asn Gly Leu Val
1               5                   10

<210> SEQ ID NO 117
<211> LENGTH: 5
<212> TYPE: PRT
<213> ORGANISM: Homo sapiens

<400> SEQUENCE: 117

Asn Tyr Gly Met His
1               5

<210> SEQ ID NO 118
<211> LENGTH: 17
<212> TYPE: PRT
<213> ORGANISM: Homo sapiens

<400> SEQUENCE: 118

Val Ile Ser Tyr Asp Gly Ser Asn Arg Tyr Tyr Ala Asp Ser Val Lys
1               5                   10                  15

Gly

<210> SEQ ID NO 119
<211> LENGTH: 8
<212> TYPE: PRT
<213> ORGANISM: Homo sapiens

<400> SEQUENCE: 119

Asp Arg Trp Asn Gly Met Asp Val
1               5

<210> SEQ ID NO 120
<211> LENGTH: 14
<212> TYPE: PRT
<213> ORGANISM: Homo sapiens

<400> SEQUENCE: 120

Ser Gly Ser Ser Ser Asn Ile Gly Ala Gly Tyr Asp Val His
1               5                   10

<210> SEQ ID NO 121
<211> LENGTH: 7
<212> TYPE: PRT
<213> ORGANISM: Homo sapiens

```
<400> SEQUENCE: 121

Ala Asn Asn Gln Arg Pro Ser
1               5

<210> SEQ ID NO 122
<211> LENGTH: 12
<212> TYPE: PRT
<213> ORGANISM: Homo sapiens

<400> SEQUENCE: 122

Ala Ala Trp Asp Asp Ser Leu Asn Gly Pro Trp Val
1               5                   10

<210> SEQ ID NO 123
<211> LENGTH: 5
<212> TYPE: PRT
<213> ORGANISM: Homo sapiens

<400> SEQUENCE: 123

Ser Tyr Gly Met His
1               5

<210> SEQ ID NO 124
<211> LENGTH: 17
<212> TYPE: PRT
<213> ORGANISM: Homo sapiens

<400> SEQUENCE: 124

Val Ile Ser Tyr Asp Gly Ser Asp Thr Ala Tyr Ala Asp Ser Val Lys
1               5                   10                  15

Gly

<210> SEQ ID NO 125
<211> LENGTH: 10
<212> TYPE: PRT
<213> ORGANISM: Homo sapiens

<400> SEQUENCE: 125

Asp His Ser Val Ile Gly Ala Phe Asp Ile
1               5                   10

<210> SEQ ID NO 126
<211> LENGTH: 13
<212> TYPE: PRT
<213> ORGANISM: Homo sapiens

<400> SEQUENCE: 126

Ser Gly Ser Ser Ser Asn Ile Gly Ser Asn Thr Val Asn
1               5                   10

<210> SEQ ID NO 127
<211> LENGTH: 7
<212> TYPE: PRT
<213> ORGANISM: Homo sapiens

<400> SEQUENCE: 127

Asp Asn Asn Lys Arg Pro Ser
1               5

<210> SEQ ID NO 128
<211> LENGTH: 10
<212> TYPE: PRT
<213> ORGANISM: Homo sapiens
```

<400> SEQUENCE: 128

Ser Ser Tyr Ala Gly Ser Asn Asn Val Val
1               5                   10

<210> SEQ ID NO 129
<211> LENGTH: 5
<212> TYPE: PRT
<213> ORGANISM: Homo sapiens

<400> SEQUENCE: 129

Ser Tyr Gly Met His
1               5

<210> SEQ ID NO 130
<211> LENGTH: 17
<212> TYPE: PRT
<213> ORGANISM: Homo sapiens

<400> SEQUENCE: 130

Val Thr Ser Tyr Asp Gly Asn Thr Lys Tyr Tyr Ala Asn Ser Val Lys
1               5                   10                  15

Gly

<210> SEQ ID NO 131
<211> LENGTH: 10
<212> TYPE: PRT
<213> ORGANISM: Homo sapiens

<400> SEQUENCE: 131

Glu Asp Cys Gly Gly Asp Cys Phe Asp Tyr
1               5                   10

<210> SEQ ID NO 132
<211> LENGTH: 14
<212> TYPE: PRT
<213> ORGANISM: Homo sapiens

<400> SEQUENCE: 132

Thr Gly Ser Ser Ser Asn Ile Gly Ala Gly Tyr Asp Val His
1               5                   10

<210> SEQ ID NO 133
<211> LENGTH: 7
<212> TYPE: PRT
<213> ORGANISM: Homo sapiens

<400> SEQUENCE: 133

Gly Asn Ser Asn Arg Pro Ser
1               5

<210> SEQ ID NO 134
<211> LENGTH: 11
<212> TYPE: PRT
<213> ORGANISM: Homo sapiens

<400> SEQUENCE: 134

Ala Ala Trp Asp Asp Ser Leu Asn Glu Gly Val
1               5                   10

<210> SEQ ID NO 135
<211> LENGTH: 5
<212> TYPE: PRT
<213> ORGANISM: Homo sapiens

<400> SEQUENCE: 135

Asn Tyr Gly Met His
1               5

<210> SEQ ID NO 136
<211> LENGTH: 17
<212> TYPE: PRT
<213> ORGANISM: Homo sapiens

<400> SEQUENCE: 136

Val Ile Ser Tyr Asp Gly Ser Asn Lys Tyr Tyr Ala Asp Ser Val Lys
1               5                   10                  15

Gly

<210> SEQ ID NO 137
<211> LENGTH: 9
<212> TYPE: PRT
<213> ORGANISM: Homo sapiens

<400> SEQUENCE: 137

Asp Gln Leu Gly Glu Ala Phe Asp Ile
1               5

<210> SEQ ID NO 138
<211> LENGTH: 14
<212> TYPE: PRT
<213> ORGANISM: Homo sapiens

<400> SEQUENCE: 138

Thr Gly Ser Ser Ser Asn Ile Gly Ala Gly Tyr Asp Val His
1               5                   10

<210> SEQ ID NO 139
<211> LENGTH: 7
<212> TYPE: PRT
<213> ORGANISM: Homo sapiens

<400> SEQUENCE: 139

Asp Asn Asn Lys Arg Pro Ser
1               5

<210> SEQ ID NO 140
<211> LENGTH: 11
<212> TYPE: PRT
<213> ORGANISM: Homo sapiens

<400> SEQUENCE: 140

Ala Thr Trp Asp Asp Ser Leu Ser Gly Pro Val
1               5                   10

<210> SEQ ID NO 141
<211> LENGTH: 5
<212> TYPE: PRT
<213> ORGANISM: Homo sapiens

<400> SEQUENCE: 141

Asp Tyr Gly Met Ser
1               5

<210> SEQ ID NO 142
<211> LENGTH: 17
<212> TYPE: PRT
<213> ORGANISM: Homo sapiens

```
<400> SEQUENCE: 142

Ala Ile Ser Gly Ser Gly Ser Ser Thr Tyr Tyr Ala Asp Ser Val Lys
1               5                   10                  15

Gly

<210> SEQ ID NO 143
<211> LENGTH: 8
<212> TYPE: PRT
<213> ORGANISM: Homo sapiens

<400> SEQUENCE: 143

Gly Asp Ile Asp Tyr Phe Asp Tyr
1               5

<210> SEQ ID NO 144
<211> LENGTH: 14
<212> TYPE: PRT
<213> ORGANISM: Homo sapiens

<400> SEQUENCE: 144

Thr Gly Ser Ser Ser Asn Phe Gly Ala Gly Tyr Asp Val His
1               5                   10

<210> SEQ ID NO 145
<211> LENGTH: 7
<212> TYPE: PRT
<213> ORGANISM: Homo sapiens

<400> SEQUENCE: 145

Glu Asn Asn Lys Arg Pro Ser
1               5

<210> SEQ ID NO 146
<211> LENGTH: 11
<212> TYPE: PRT
<213> ORGANISM: Homo sapiens

<400> SEQUENCE: 146

Ala Ala Trp Asp Asp Ser Leu Asn Gly Pro Val
1               5                   10

<210> SEQ ID NO 147
<211> LENGTH: 5
<212> TYPE: PRT
<213> ORGANISM: Homo sapiens

<400> SEQUENCE: 147

Ser Tyr Gly Met His
1               5

<210> SEQ ID NO 148
<211> LENGTH: 17
<212> TYPE: PRT
<213> ORGANISM: Homo sapiens

<400> SEQUENCE: 148

Val Ile Ser Tyr Asp Gly Ser Asn Lys Tyr Tyr Ala Asp Ser Val Lys
1               5                   10                  15

Gly

<210> SEQ ID NO 149
<211> LENGTH: 8
<212> TYPE: PRT
```

<213> ORGANISM: Homo sapiens

<400> SEQUENCE: 149

Glu Arg Arg Asp Ala Phe Asp Ile
1               5

<210> SEQ ID NO 150
<211> LENGTH: 14
<212> TYPE: PRT
<213> ORGANISM: Homo sapiens

<400> SEQUENCE: 150

Thr Gly Ser Ser Ser Asn Ile Gly Ala Gly Tyr Asp Val His
1               5                   10

<210> SEQ ID NO 151
<211> LENGTH: 7
<212> TYPE: PRT
<213> ORGANISM: Homo sapiens

<400> SEQUENCE: 151

Ser Asp Asn Gln Arg Pro Ser
1               5

<210> SEQ ID NO 152
<211> LENGTH: 9
<212> TYPE: PRT
<213> ORGANISM: Homo sapiens

<400> SEQUENCE: 152

Ala Thr Trp Asp Ser Asp Thr Pro Val
1               5

<210> SEQ ID NO 153
<211> LENGTH: 5
<212> TYPE: PRT
<213> ORGANISM: Homo sapiens

<400> SEQUENCE: 153

Ser Tyr Gly Met His
1               5

<210> SEQ ID NO 154
<211> LENGTH: 17
<212> TYPE: PRT
<213> ORGANISM: Homo sapiens

<400> SEQUENCE: 154

Val Ile Ser Tyr Asp Gly Ser Asn Lys Tyr Tyr Ala Asp Ser Val Lys
1               5                   10                  15

Gly

<210> SEQ ID NO 155
<211> LENGTH: 10
<212> TYPE: PRT
<213> ORGANISM: Homo sapiens

<400> SEQUENCE: 155

Asp His Ser Ala Ala Gly Tyr Phe Asp Tyr
1               5                   10

<210> SEQ ID NO 156
<211> LENGTH: 13
<212> TYPE: PRT

<213> ORGANISM: Homo sapiens

<400> SEQUENCE: 156

Ser Gly Ser Ser Ser Asn Ile Gly Ser Asn Thr Val Asn
1               5                   10

<210> SEQ ID NO 157
<211> LENGTH: 7
<212> TYPE: PRT
<213> ORGANISM: Homo sapiens

<400> SEQUENCE: 157

Gly Asn Ser Ile Arg Pro Ser
1               5

<210> SEQ ID NO 158
<211> LENGTH: 11
<212> TYPE: PRT
<213> ORGANISM: Homo sapiens

<400> SEQUENCE: 158

Ala Ser Trp Asp Asp Ser Leu Ser Ser Pro Val
1               5                   10

<210> SEQ ID NO 159
<211> LENGTH: 5
<212> TYPE: PRT
<213> ORGANISM: Homo sapiens

<400> SEQUENCE: 159

Ser Tyr Gly Met His
1               5

<210> SEQ ID NO 160
<211> LENGTH: 17
<212> TYPE: PRT
<213> ORGANISM: Homo sapiens

<400> SEQUENCE: 160

Gly Ile Ser Trp Asp Ser Ala Ile Ile Asp Tyr Ala Gly Ser Val Lys
1               5                   10                  15

Gly

<210> SEQ ID NO 161
<211> LENGTH: 10
<212> TYPE: PRT
<213> ORGANISM: Homo sapiens

<400> SEQUENCE: 161

Asp Glu Ala Ala Ala Gly Ala Phe Asp Ile
1               5                   10

<210> SEQ ID NO 162
<211> LENGTH: 14
<212> TYPE: PRT
<213> ORGANISM: Homo sapiens

<400> SEQUENCE: 162

Thr Gly Ser Ser Ser Asn Ile Gly Ala Gly Tyr Asp Val His
1               5                   10

<210> SEQ ID NO 163
<211> LENGTH: 7
<212> TYPE: PRT

<213> ORGANISM: Homo sapiens

<400> SEQUENCE: 163

Gly Asn Thr Asp Arg Pro Ser
1               5

<210> SEQ ID NO 164
<211> LENGTH: 12
<212> TYPE: PRT
<213> ORGANISM: Homo sapiens

<400> SEQUENCE: 164

Ala Ala Trp Asp Asp Ser Leu Ser Gly Pro Val Val
1               5                   10

<210> SEQ ID NO 165
<211> LENGTH: 5
<212> TYPE: PRT
<213> ORGANISM: Homo sapiens

<400> SEQUENCE: 165

Ser Tyr Gly Ile Ser
1               5

<210> SEQ ID NO 166
<211> LENGTH: 17
<212> TYPE: PRT
<213> ORGANISM: Homo sapiens

<400> SEQUENCE: 166

Gly Ile Ser Gly Ser Gly Gly Asn Thr Tyr Tyr Ala Asp Ser Val Lys
1               5                   10                  15

Gly

<210> SEQ ID NO 167
<211> LENGTH: 12
<212> TYPE: PRT
<213> ORGANISM: Homo sapiens

<400> SEQUENCE: 167

Ser Val Gly Ala Tyr Ala Asn Asp Ala Phe Asp Ile
1               5                   10

<210> SEQ ID NO 168
<211> LENGTH: 14
<212> TYPE: PRT
<213> ORGANISM: Homo sapiens

<400> SEQUENCE: 168

Thr Gly Ser Ser Ser Asn Ile Gly Ala Gly Tyr Asp Val His
1               5                   10

<210> SEQ ID NO 169
<211> LENGTH: 7
<212> TYPE: PRT
<213> ORGANISM: Homo sapiens

<400> SEQUENCE: 169

Gly Asp Thr Asn Arg Pro Ser
1               5

<210> SEQ ID NO 170
<211> LENGTH: 11
<212> TYPE: PRT

<213> ORGANISM: Homo sapiens

<400> SEQUENCE: 170

Ala Ala Trp Asp Asp Ser Leu Asn Gly Pro Val
1               5                   10

<210> SEQ ID NO 171
<211> LENGTH: 5
<212> TYPE: PRT
<213> ORGANISM: Homo sapiens

<400> SEQUENCE: 171

Ser Tyr Gly Met His
1               5

<210> SEQ ID NO 172
<211> LENGTH: 17
<212> TYPE: PRT
<213> ORGANISM: Homo sapiens

<400> SEQUENCE: 172

Val Ile Ser Tyr Asp Gly Ser Asn Lys Tyr Tyr Ala Asp Ser Val Lys
1               5                   10                  15

Gly

<210> SEQ ID NO 173
<211> LENGTH: 8
<212> TYPE: PRT
<213> ORGANISM: Homo sapiens

<400> SEQUENCE: 173

Glu Leu Tyr Asp Ala Phe Asp Ile
1               5

<210> SEQ ID NO 174
<211> LENGTH: 14
<212> TYPE: PRT
<213> ORGANISM: Homo sapiens

<400> SEQUENCE: 174

Thr Gly Ser Ser Ser Asn Ile Gly Ala Gly Tyr Asp Val His
1               5                   10

<210> SEQ ID NO 175
<211> LENGTH: 7
<212> TYPE: PRT
<213> ORGANISM: Homo sapiens

<400> SEQUENCE: 175

Ala Asp Asp His Arg Pro Ser
1               5

<210> SEQ ID NO 176
<211> LENGTH: 11
<212> TYPE: PRT
<213> ORGANISM: Homo sapiens

<400> SEQUENCE: 176

Ala Ser Trp Asp Asp Ser Gln Arg Ala Val Ile
1               5                   10

<210> SEQ ID NO 177
<211> LENGTH: 5
<212> TYPE: PRT

<213> ORGANISM: Homo sapiens

<400> SEQUENCE: 177

Asn Tyr Gly Met His
1               5

<210> SEQ ID NO 178
<211> LENGTH: 13
<212> TYPE: PRT
<213> ORGANISM: Homo sapiens

<400> SEQUENCE: 178

Val Ile Ser Tyr Asp Gly Ser Asn Lys Tyr Tyr Ala Asp
1               5                   10

<210> SEQ ID NO 179
<211> LENGTH: 8
<212> TYPE: PRT
<213> ORGANISM: Homo sapiens

<400> SEQUENCE: 179

Glu Tyr Lys Asp Ala Phe Asp Ile
1               5

<210> SEQ ID NO 180
<211> LENGTH: 13
<212> TYPE: PRT
<213> ORGANISM: Homo sapiens

<400> SEQUENCE: 180

Thr Gly Ser Ser Ser Asn Ile Gly Ser Asn Thr Val Asn
1               5                   10

<210> SEQ ID NO 181
<211> LENGTH: 7
<212> TYPE: PRT
<213> ORGANISM: Homo sapiens

<400> SEQUENCE: 181

Asp Asn Asn Lys Arg Pro Ser
1               5

<210> SEQ ID NO 182
<211> LENGTH: 9
<212> TYPE: PRT
<213> ORGANISM: Homo sapiens

<400> SEQUENCE: 182

Gln Ala Trp Gly Thr Gly Ile Arg Val
1               5

<210> SEQ ID NO 183
<211> LENGTH: 5
<212> TYPE: PRT
<213> ORGANISM: Homo sapiens

<400> SEQUENCE: 183

Ser Tyr Gly Met His
1               5

<210> SEQ ID NO 184
<211> LENGTH: 17
<212> TYPE: PRT
<213> ORGANISM: Homo sapiens

<400> SEQUENCE: 184

Val Ile Ser Tyr Asp Gly Ser Asn Lys Tyr Tyr Ala Asp Ser Val Lys
1               5                   10                  15

Gly

<210> SEQ ID NO 185
<211> LENGTH: 9
<212> TYPE: PRT
<213> ORGANISM: Homo sapiens

<400> SEQUENCE: 185

Glu Phe Gly Tyr Ile Ile Leu Asp Tyr
1               5

<210> SEQ ID NO 186
<211> LENGTH: 13
<212> TYPE: PRT
<213> ORGANISM: Homo sapiens

<400> SEQUENCE: 186

Ser Gly Ser Ser Ser Asn Ile Gly Ser Asn Thr Val Asn
1               5                   10

<210> SEQ ID NO 187
<211> LENGTH: 7
<212> TYPE: PRT
<213> ORGANISM: Homo sapiens

<400> SEQUENCE: 187

Arg Asp Tyr Glu Arg Pro Ser
1               5

<210> SEQ ID NO 188
<211> LENGTH: 11
<212> TYPE: PRT
<213> ORGANISM: Homo sapiens

<400> SEQUENCE: 188

Met Ala Trp Asp Asp Ser Leu Ser Gly Val Val
1               5                   10

<210> SEQ ID NO 189
<211> LENGTH: 5
<212> TYPE: PRT
<213> ORGANISM: Homo sapiens

<400> SEQUENCE: 189

Asn His Gly Met His
1               5

<210> SEQ ID NO 190
<211> LENGTH: 17
<212> TYPE: PRT
<213> ORGANISM: Homo sapiens

<400> SEQUENCE: 190

Val Ile Ser Tyr Asp Gly Thr Asn Lys Tyr Tyr Ala Asp Ser Val Arg
1               5                   10                  15

Gly

<210> SEQ ID NO 191
<211> LENGTH: 8
<212> TYPE: PRT

```
<213> ORGANISM: Homo sapiens

<400> SEQUENCE: 191

Glu Thr Trp Asp Ala Phe Asp Val
1               5

<210> SEQ ID NO 192
<211> LENGTH: 13
<212> TYPE: PRT
<213> ORGANISM: Homo sapiens

<400> SEQUENCE: 192

Ser Gly Ser Ser Ser Asn Ile Gly Ser Asn Asn Ala Asn
1               5                   10

<210> SEQ ID NO 193
<211> LENGTH: 7
<212> TYPE: PRT
<213> ORGANISM: Homo sapiens

<400> SEQUENCE: 193

Asp Asn Asn Lys Arg Pro Ser
1               5

<210> SEQ ID NO 194
<211> LENGTH: 9
<212> TYPE: PRT
<213> ORGANISM: Homo sapiens

<400> SEQUENCE: 194

Gln Ala Trp Asp Ser Ser Thr Val Val
1               5

<210> SEQ ID NO 195
<211> LENGTH: 330
<212> TYPE: PRT
<213> ORGANISM: Homo sapiens

<400> SEQUENCE: 195

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
```

```
                165                 170                 175
Glu Gln Tyr Gln Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 196
<211> LENGTH: 330
<212> TYPE: PRT
<213> ORGANISM: Mus musculus

<400> SEQUENCE: 196

Ala Lys Thr Thr Ala Pro Ser Val Tyr Pro Leu Ala Pro Val Cys Gly
1               5                   10                  15

Asp Thr Thr Gly Ser Ser Val Thr Leu Gly Cys Leu Val Lys Gly Tyr
            20                  25                  30

Phe Pro Glu Pro Val Thr Leu Thr Trp Asn Ser Gly Ser Leu Ser Ser
            35                  40                  45

Gly Val His Thr Phe Pro Ala Val Leu Gln Ser Asp Leu Tyr Thr Leu
        50                  55                  60

Ser Ser Ser Val Thr Val Thr Ser Ser Thr Trp Pro Ser Gln Ser Ile
65                  70                  75                  80

Thr Cys Asn Val Ala His Pro Ala Ser Ser Thr Lys Val Asp Lys Lys
                85                  90                  95

Ile Glu Pro Arg Gly Pro Thr Ile Lys Pro Cys Pro Pro Cys Lys Cys
            100                 105                 110

Pro Ala Pro Asn Leu Leu Gly Gly Pro Ser Val Phe Ile Phe Pro Pro
            115                 120                 125

Lys Ile Lys Asp Val Leu Met Ile Ser Leu Ser Pro Ile Val Thr Cys
130                 135                 140

Val Val Val Asp Val Ser Glu Asp Asp Pro Asp Val Gln Ile Ser Trp
145                 150                 155                 160

Phe Val Asn Asn Val Glu Val His Thr Ala Gln Thr Gln Thr His Arg
            165                 170                 175

Glu Asp Tyr Ala Ser Thr Leu Arg Val Val Ser Ala Leu Pro Ile Gln
            180                 185                 190

His Gln Asp Trp Met Ser Gly Lys Glu Phe Lys Cys Lys Val Asn Asn
            195                 200                 205
```

```
                                  -continued

Lys Asp Leu Pro Ala Pro Ile Glu Arg Thr Ile Ser Lys Pro Lys Gly
    210                 215                 220

Ser Val Arg Ala Pro Gln Val Tyr Val Leu Pro Pro Pro Glu Glu Glu
225                 230                 235                 240

Met Thr Lys Lys Gln Val Thr Leu Thr Cys Met Val Thr Asp Phe Met
                245                 250                 255

Pro Glu Asp Ile Tyr Val Glu Trp Thr Asn Asn Gly Lys Thr Glu Leu
                260                 265                 270

Asn Tyr Lys Asn Thr Glu Pro Val Leu Asp Ser Asp Gly Ser Tyr Phe
            275                 280                 285

Met Tyr Ser Lys Leu Arg Val Glu Lys Lys Asn Trp Val Glu Arg Asn
    290                 295                 300

Ser Tyr Ser Cys Ser Val Val His Glu Gly Leu His Asn His His Thr
305                 310                 315                 320

Thr Lys Ser Phe Ser Arg Thr Pro Gly Lys
                325                 330

<210> SEQ ID NO 197
<211> LENGTH: 105
<212> TYPE: PRT
<213> ORGANISM: Mus musculus

<400> SEQUENCE: 197

Gln Pro Lys Ser Ser Pro Ser Val Thr Leu Phe Pro Pro Ser Ser Glu
1               5                   10                  15

Glu Leu Glu Thr Asn Lys Ala Thr Leu Val Cys Thr Ile Thr Asp Phe
            20                  25                  30

Tyr Pro Gly Val Val Thr Val Asp Trp Lys Val Asp Gly Thr Pro Val
        35                  40                  45

Thr Gln Gly Met Glu Thr Thr Gln Pro Ser Lys Gln Ser Asn Asn Lys
    50                  55                  60

Tyr Met Ala Ser Ser Tyr Leu Thr Leu Thr Ala Arg Ala Trp Glu Arg
65                  70                  75                  80

His Ser Ser Tyr Ser Cys Gln Val Thr His Glu Gly His Thr Val Glu
                85                  90                  95

Lys Ser Leu Ser Arg Ala Asp Cys Ser
                100                 105
```

COMBINATION AND USE OF ANTIBODIES

CROSS-REFERENCE TO RELATED APPLICATIONS

This application is the U.S. National Stage of International Application No. PCT/EP2019/050566, filed Jan. 10, 2019, which claims the benefit of and priority to Great Britain Patent Application Nos. 1800395.4, filed Jan. 10, 2018, and 1800461.4, filed Jan. 11, 2018, the contents of each of which are incorporated by reference in their entireties for all purposes.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 84,878 byte ASCII (text) file named "Seq_List" created on Jan. 10, 2019.

FIELD OF THE INVENTION

The present invention relates to the combined use of 1) an antibody molecule that specifically binds FcγRIIb via its Fab region, but lacks Fc region or has reduced binding via its Fc region to at least one Fcγ receptor, and 2) an immune cell depleting or deactivating antibody molecule that specifically binds to a receptor present on an immune cell that suppresses anti-cancer immunity and which immune cell depleting or deactivating antibody molecule has an Fc region that binds to at least one activating Fcγ receptor, in treatment of FcγRIIb-negative cancers.

BACKGROUND OF THE INVENTION

It has long been appreciated that the inhibitory Fc gamma receptor (FcγR) IIB, expressed by numerous cells of the immune system, negatively regulates both innate and adaptive immunity through engagement of immune complexes (IC). Similarly, the knowledge that FcγRIIB negatively regulates monoclonal antibody mediated immunotherapy has been known for over a decade. As such, FcγRIIB-deficient mice are able to clear tumours more effectively than wild type (WT) mice when treated with therapeutic mAbs, indicating that FcγRIIB expression on effector cells (i.e., macrophages and monocytes) leads to suppression of their phagocytic and cytotoxic potential in vivo. Moreover, FcγRIIB regulates the antigen-presenting potential of dendritic cells (DC) and FcγRIIB—ve (van Montfoor et al., J Immunol. 2012 Jul 1; 189(1):92-101). DCs have an improved capacity to activate naive T cells. Recently, antagonist antibodies that block FcγRIIB-signalling and internalization in B cells were developed. Such antibodies showed efficient deletion of FcγRIIB-expressing B cells, and efficiently boosted rituximab-mediated deletion of normal and malignant B cells, demonstrating a utility in hematologic cancer. It was, however, not examined or demonstrated whether such antibodies would have utility also in treatment of FcγRIIB negative cancers, such as solid cancers.

SUMMARY OF THE INVENTION

We here show, unexpectedly, that only anti-FcγRIIB antibodies lacking Fc region, or whose Fc-region shows reduced or impaired binding to FcγRs e.g. F(ab)'₂ antibodies or aglycosylated antibodies, are able to enhance the therapeutic activity of antibodies used for treatment of FcγRIIB-negative cancers, including solid cancers. This finding was unexpected, since previous studies had indicated that wild-type IgG1 anti-FcγRIIB anti-bodies were equally capable of blocking FcγRIIB receptors, and equally capable of preventing rituximab internalization and rituximab-induced FcγRIIB phosphorylation in vitro.

According to the present invention it is possible to enhance the therapeutic activity of immunomodulatory anti-cancer antibodies, whose therapeutic activity is dependent on engagement of FcγRs. Such antibodies include, but are not limited to, antibodies to so called checkpoint inhibitor targets, e.g. CTLA-4, immune agonist targets, e.g. OX40, 4-1BB, and GITR, and the interleukin-2 receptor (IL-2R).

Disclosed herein is a first antibody molecule that specifically binds FcγRIIb via (or through) its Fab region and that lacks Fc region or has reduced binding to Fcγ receptors via (or through) its Fc region, for use in combination with a second antibody molecule that specifically binds to a receptor present on an immune cell, wherein the immune cell is an immune cell that suppresses anti-cancer immunity, which second antibody molecule has an Fc region that binds to at least one activating Fcγ receptor, and wherein the binding of the second antibody molecule to the receptor on the immune cell causes depletion and/or deactivation of the immune cell;

in the treatment of an FcγRIIb-negative cancer in a patient.

Disclosed herein is also a pharmaceutical composition comprising:

(i) a first antibody molecule that specifically binds FcγRIIb via its Fab region and that lacks Fc region or has reduced binding to Fcγ receptors via its Fc region, and (ii) a second antibody molecule that specifically binds to a receptor present on an immune cell, wherein the immune cell is an immune cell that suppresses anti-cancer immunity, which second antibody molecule has an Fc region that binds to at least one activating Fcγ receptor, and wherein binding of the second antibody to the receptor on the immune cell causes depletion and/or deactivation of the immune cell;

for use in the treatment of an FcγRIIb-negative cancer in a patient.

Disclosed herein is further a kit for use in the treatment of an FcγRIIb-negative cancer comprising:

(i) a first antibody molecule that specifically binds FcγRIIb via its Fab region and that lacks Fc region or has a reduced binding to Fcγ receptors via its Fc region, and (ii) a second antibody molecule that specifically binds to a receptor present on an immune cell, wherein the immune cell is an immune cell that suppresses anti-cancer immunity, which second antibody molecule has an Fc region that binds to at least one activating Fcγ receptor, and wherein binding of the second antibody molecule to the receptor on the immune cell causes depletion or deactivation of the immune cell.

Further disclosed herein is the use of:

(i) a first antibody molecule that specifically binds FcγRIIb via its Fab region and that lacks Fc region or has reduced binding to Fcγ receptors via its Fc region, and (ii) a second antibody molecule that specifically binds to a receptor present on an immune cell, wherein the immune cell is an immune cell that suppresses anti-cancer immunity, which second antibody molecule has an Fc region that binds to at least one activating Fcγ receptor, and wherein the binding of the second antibody to the receptor on the immune cell causes depletion or deactivation of the immune cell;

in the manufacture of a medicament for use in the treatment of an FcγRIIb-negative cancer in a patient.

Disclosed herein is also a method for treatment of an FcγRIIb-negative cancer in a patient, comprising administering:
(i) a first antibody molecule that specifically binds FcγRIIb via its Fab region and that lacks Fc region or has reduced binding to Fcγ receptors via its Fc region, and
(ii) a second antibody molecule that specifically binds to a receptor present on an immune cell, wherein the immune cell is an immune cell that suppresses anti-cancer immunity, which second antibody molecule has an Fc region that is capable of activating at least one activating Fcy receptor, and wherein the binding of the second antibody to the receptor on the immune cell causes depletion or deactivation of the immune cell.

DETAILD DESCRIPTION OF THE INVENTION

Thus, the present invention concerns the combined use of:
(i) an antibody molecule that specifically binds FcγRIIb via its Fab region and that lacks Fc region or has reduced binding to Fcy receptors via its Fc region (below often denoted a first antibody molecule or the first antibody molecule), and
(ii) an antibody molecule that specifically binds to a receptor present on an immune cell (below often denoted a second antibody or the second antibody), wherein the immune cell is an immune cell that suppresses anti-cancer immunity, which antibody molecule has an Fc region that binds to at least one activating Fcy receptor, and wherein the binding of this antibody molecule to the receptor on the immune cell causes depletion or deactivation of the immune cell. This second antibody molecule is thus an immune cell depleting or deactivating antibody molecule.

This combination is intended to be used in the treatment of an FcγRIIb-negative cancer in a patient, with the aim to improve therapeutic efficacy of the second antibody molecule through enhanced binding of its Fc part to activatory FcγRs, with reduced binding/activation of inhibitory FcγR.

Fc receptors are membrane proteins which are found on the cell surface of immune effector cells, such as macrophages. The name is derived from their binding specificity for the Fc region of antibodies, which is the usual way an antibody binds to the receptor. However, certain antibodies can also bind the Fc receptors via the antibodies' CDR sequences in the case of antibodies specifically binding to one or more Fc receptors.

A subgroup of the Fc receptors are Fcγ receptors (Fc-gamma receptors, FcgammaR), which are specific for IgG antibodies. There are two types of Fcγ receptors: activating Fcγ receptors (also denoted activatory Fcγ receptors) and inhibitory Fcγ receptors. The activating and the inhibitory receptors transmit their signals via immunoreceptor tyrosine-based activation motifs (ITAM) or immunoreceptor tyrosine-based inhibitory motifs (ITIM), respectively. In humans, FcγRIIb (CD32b) is an inhibitory Fcγ receptor, while FcγRI (CD64), FcγRIIa (CD32a), FcγRIIc (CD32c), FcγRIIIa (CD16a) and FcγRIV are activating Fcγ receptors.

FcγgRIIIb is a GPI-linked receptor expressed on neutrophils that lacks an ITAM motif but through its ability to cross-link lipid rafts and engage with other receptors is also considered activatory. In mice, the activating receptors are FcγRI, FcγRIII and FcγRIV.

It is well-known that antibodies modulate immune cell activity through interaction with Fcγ receptors. Specifically, how antibody immune complexes modulates immune cell activation is determined by their relative engagement of activating and inhibitory γ receptors. Different antibody isotypes bind with different affinity to activating and inhibitory Fcγ receptors, resulting in different A:I ratios (activation:inhibition ratios) (Nimmerjahn et al; Science. 2005 Dec. 2; 310(5753):1510-2).

By binding to an inhibitory Fcγ receptor, an antibody can inhibit, block and/or downmodulate effector cell functions.

By binding to an activating Fcγ receptor, an antibody can activate effector cell functions and thereby trigger mechanisms such as antibody-dependent cellular cytotoxicity (ADCC), antibody dependent cellular phagocytosis (ADCP), cytokine release, and/or antibody dependent endocytosis, as well as NETosis (i.e. activation and release of NETs, Neutrophil extracellular traps) in the case of neutrophils. Antibody binding to an activating Fcγ receptor can also lead to an increase in certain activation markers, such as CD40, MHCII, CD38, CD80 and/or CD86.

The antibody molecule according to the invention that specifically binds FcγRIIb, i.e. the first antibody, binds to or interacts with this Fcγ receptor via the Fab region of the antibody, i.e. via the antigen-binding region on an antibody that binds to antigens which is composed of one constant and one variable domain of each of the heavy and the light chain. In particular, it binds to FcγRIIb present on an immune effector cell, and in particular to FcγRIIb present on the surface of an immune effector cell. If this antibody would have had a usual or ordinary Fc region, the antibody could also have bound to an activating Fcγ receptor through normal interaction between the Fc region and Fc receptor. However, according to the invention, the antibody molecule that specifically binds FcγRIIb completely lacks Fc region or has reduced binding to Fcγ receptors, which means that the antibody molecule that specifically binds or interacts with FcγRIIb binds poorly to or cannot at all bind to or interact with Fcγ receptors. This appears to have at least two therapeutically important consequences:

1) lack of Fc-mediated binding to activatory FcγRs leaves a greater number of activatory Fc gamma receptors available for binding to Fc's of (other) therapeutic anticancer antibodies. This is important since clustering of an increasing number of activatory FcγRs (vs inhibitory FcγRs; Nimmerjahn et al; Science. 2005 Dec. 2;310(5753):1510-2) is known to increase effector cell mediated target cell deletion, a mechanism underlying activity of both checkpoint inhibitor, immune agonist, and other immunomodulatory antibodies, such as anti-IL-2R.

2) lack of, or reduced, Fc-mediated binding to inhibitory FcγR was shown to reduce inhibitory signalling in FcγR-expressing immune effector cells. Thus, lack of or reduced Fc-mediated binding to FcγR of the FcγRIIB targeting antibody likely improves therapeutic efficacy by at least two mechanisms, involving both improved activatory FcγR and reduced inhibitory Fcγ signalling in immune effector cells in response to a second immunomodulatory anti-cancer antibody.

"Reduced binding" or "binding with reduced affinity" means in this context that antibody molecule has reduced Fc mediated binding to Fcγ receptors, or in other words that the Fc region of the antibody molecule that specifically binds FcγRIIb binds to an activating Fcγ receptor with lower affinity than the Fc region of a normal human IgG1. The reduction in binding can be assessed using techniques such as surface plasmon resonance. In this context "normal IgG1" means a conventionally produced IgG1 with a non-mutated Fc region that has not been produced so as to alter its glycosylation. As a reference for this "normal IgG1" it is possible to use rituximab produced in CHO cells without any modifications (Tipton et al, Blood 2015 125:1901-1909; rituximab is described i.a. in EP 0 605 442).

"Reduced binding" means that binding of the Fc region of the antibody molecule that specifically binds FcγRIIb binds to an activating Fcγ receptor is at least 10 fold reduced for all Fc receptors compared to the binding of the Fc region of a normal human IgG1 to the same receptors. In some embodiments it is at least 20 fold reduced. In some embodiments it is at least 30 fold reduced. In some embodiments it is at least 40 fold reduced. In some embodiments it is at least 50 fold reduced. In some embodiments it is at least 60 fold reduced. In some embodiments it is at least 70 fold reduced.

In some embodiments of the present invention, the antibody molecule that specifically binds FcγRIIb does not bind at all with its Fc region, and in some such cases the antibody does not have an Fc region; it may then be a Fab, Fab'2, scFv or PEGYLATED versions thereof.

In some embodiments, the antibody molecule that specifically binds FcγRIIb may be a lama antibody, and in particular a lama hcIgG. Like all mammals, camelids produce conventional antibodies made of two heavy chains and two light chains bound together with disulphide bonds in a Y shape (IgGi). However, they also produce two unique sub-classes of immunoglobulin G, $IgG_2$ and $IgG_3$, also known as heavy chain IgG (hcIgG). These antibodies are made of only two heavy chains that lack the CH1 region but still bear an antigen binding domain at their N-terminus called $V_HH$. Conventional Ig requires the association of variable regions from both heavy and light chains to allow a high diversity of antigen-antibody interactions. Although isolated heavy and light chains still show this capacity, they exhibit very low affinity[4] when compared to paired heavy and light chains. The unique feature of hcIgG is the capacity of their monomeric antigen binding regions to bind antigens with specificity, affinity and especially diversity that are comparable to conventional antibodies without the need of pairing with another region.

In some embodiments reduced binding means that the antibody has a 20 fold reduced affinity with regards to binding to FcγRI.

In order to obtain reduced binding of an IgG1 antibody, such as an IgG1 antibody, to an Fc receptor, it is possible to modify the Fc region of the IgG antibody by aglycosylation. Such aglycosylation, for example of an IgG1 antibody, may for example be achieved by an amino acid substitution of the asparagine in position 297 (N297X) in the antibody chain. The substation may be with a glutamine (N297Q), or with an alanine (N297A), or with a glycine (N297G), or with an asparagine (N297D), or by a serine (N297S).

The Fc region may be modified by further substitutions, for example as described by Jacobsen FW et al., JBC 2017, 292, 1865-1875, (see e.g. Table 1). Such additional substitutions include L242C, V259C, A287C, R292C, V302C, L306C, V323C, I332C, and/or K334C. Such modifications also include the following combinations of substitutions in an IgG1:

L242C, N297G, K334C,
A287C, N297G, L306C,
R292C, N297G, V302C,
N297G, V323C, I332C, and
V259C, N297G, L306C.

Alternatively, the carbohydrate in the Fc region can be cleaved enzymatically and/or the cells used for producing the antibody can be grown in media that impairs carbohydrate addition and/or cells engineered to lack the ability to add the sugars can be used for the antibody production, or by production of antibodies in host cells that do not glycosylate or do not functionally glycosylate antibodies e.g. prokaryotes including E.coli, as explained above.

Reduced affinity for Fc gamma receptors can further be achieved through engineering of amino acids in the antibody Fc region (such modifications have previously been described by e.g. Xencor, Macrogenics, and Genentech), or by production of antibodies in host cells that do not glycosylate or does not functionally glycosylate antibodies e.g. prokaryotes including E. coli.

In addition to having reduced binding to Fcγ receptors through the Fc region, it is in some embodiments preferred that the antibody molecule that specifically binds FcγRIIb does not give rise to phosphorylation of FcγRIIb when binding the target. Phosphorylation of the ITIM of FcγRIIb is an inhibitory event that blocks the activity in the immune cell.

Fc gamma receptor expressing immune effector cell refers herein to principally innate effector cells, and includes specifically macrophages, neutrophils, monocytes, natural killer (NK) cells, basophils, eiosinophils, mast cells, and platelets. Cytotoxic T cells and memory T cells do not typically express FcγRs, but may do so in specific circumstances. In some embodiments the immune effector cell is an innate immune effector cell. In some embodiments, the immune effector cell is a macrophage.

Contrary to the antibody molecule that specifically binds FcγRIIb, the antibody molecule that specifically binds to or interacts with a receptor present on a target immune cell, i.e. the second antibody molecule or the immune cell depleting or deactivating antibody molecule, has an Fc region that binds to or interacts with an activating Fcγ receptor in an extent that is not reduced or at least not substantially reduced. The immune cell to which the second antibody molecule, i.e. the immune cell depleting or deactivating antibody molecule, binds is an immune cell that supresses anti-cancer immunity and the binding of the second antibody to that cell causes depletion or deactivation of that immune cell, which could belong to innate (e.g. TAM, TAN or MDSC) or adaptive arms (e.g. T cell) of the immune system.

By depletion of a cell, we refer herein to depletion, deletion or elimination of immune cells through physical clearance of cells. In particular, we refer to depletion of intratumoural immune cells, or depletion of tumour-associated immune cells e.g. those present in tumour draining lymph nodes.

By deactivation of an immune cell, were refer herein to blocked or reduced activity e.g. reduced cytokine, growth factor, arginase or nitric oxide production, In this context, deactivation of an immune cell also encompasses skewing of the immune cells so that its pro-tumour phenotype is altered into an anti-tumour phenotype e.g. by decreased anti-inflammatory cytokine release, decreased release of proangiogenic growth factors, and increased pro-inflammatory cytokine release and increased reactive oxygen species (ROS), phagocytosis or ADCC activity.

How to determine whether or not an antibody is an immune cell depleting or deactivating antibody is explained further below.

The immune cell to which the second antibody molecule specifically binds is an immune cell that supresses anti-cancer immunity. In this context, anti-cancer immunity includes, but is not limited to, induction of adaptive T cell mediated anti-cancer immunity, including generation of memory recall response.

The immune cell to which the second antibody molecule specifically binds can be a regulatory T cell. Regulatory T cells, Treg cells, Tregs or $T_{regs}$, (formerly known as suppressor T cells, sometimes also called suppressive regulatory T cells), are a subpopulation of T cells which are capable of suppressing other immune cells in normal and pathological immune settings. The immune cell to which the second antibody molecule specifically binds can alternatively be a myeloid cell, in particular a tumour-associated myeloid cell. In some embodiments, the tumour-associated myeloid cell is a tumour-associated macrophage, which is sometimes denoted TAM. In some embodiments it is a tumour-associated neutrophil, which is sometimes denoted TAN. In some embodiments it is a dendritic cell. In some embodiments it is a myeloid-derived suppressor cell, which may be of monocytic or granulocytic type.

In addition to binding specifically to a target on the immune cell, the second antibody molecule binds via its Fc region to an activating Fcγ receptor present on the same immune effector cell as the FcγRIIb to which the first antibody molecule binds and/or to an activating Fcγ receptor present on another immune effector cell. In order to be able to bind to an activating Fcγ receptor, the Fc region of the second antibody should at least in some embodiments be glycosylated at position 297. The carbohydrate residue in this position helps binding to Fcγ receptors. In some embodiments it is preferred that these residues are biantennary carbohydrates which contain GlnNAc, mannose, with terminal galactose residues and sialic acid. It should contain the $CH_2$ part of the Fc molecule.

The cancer to be treated or treatable in accordance with the present invention is an FcγRIIb-negative cancer, which means that it is a cancer that does not present any FcγRIIb receptors. This can be tested using anti-FcγRIIB specific antibodies in a variety of methods including immunohistochemistry and flow cytometry such as indicated in Tutt et al J Immunol 2015, 195 (11) 5503-5516.

Antibodies are well known to those skilled in the art of immunology and molecular biology. Typically, an antibody comprises two heavy (H) chains and two light (L) chains. Herein, we sometimes refer to this complete antibody molecule as a full-size or full-length antibody. The antibody's heavy chain comprises one variable domain (VH) and three constant domains (CH1, CH2 and CH3), and the antibody's molecule light chain comprises one variable domain (VL) and one constant domain (CL). The variable domains (sometimes collectively referred to as the Fv region) bind to the antibody's target, or antigen. Each variable domain comprises three loops, referred to as complementary determining regions (CDRs), which are responsible for target binding. The constant domains are not involved directly in binding an antibody to an antigen, but exhibit various effector functions. Depending on the amino acid sequence of the constant region of their heavy chains, antibodies or immunoglobulins can be assigned to different classes. There are five major classes of immunoglobulins: IgA, IgD, IgE, IgG and IgM, and in humans several of these are further divided into subclasses (isotypes), e.g., IgG1, IgG2, IgG3, and IgG4; IgA1 and IgA2.

Another part of an antibody is the Fc region (otherwise known as the fragment crystallisable domain), which comprises two of the constant domains of each of the anti-body's heavy chains. As mentioned above, the Fc region is responsible for interactions between the antibody and Fc receptor.

The term antibody molecule, as used herein, encompasses full-length or full-size antibodies as well as functional fragments of full length antibodies and derivatives of such antibody molecules.

Functional fragments of a full-size antibody have the same antigen binding characteristics as the corresponding full-size antibody and include either the same variable domains (i.e. the VH and VL sequences) and/or the same CDR sequences as the corresponding full-size antibody. That the functional fragment has the same antigen binding characteristics as the corresponding full-size antibody means that it binds to the same epitope on the target as the full-size antibody. Such a functional fragment may correspond to the Fv part of a full-size antibody. Alternatively, such a fragment may be a Fab, also denoted F(ab), which is a monovalent antigen-binding fragment that does not contain a Fc part, or a $F(ab')_2$, which is an divalent antigen-binding fragment that contains two antigen-binding Fab parts linked together by disulfide bonds, or a F(ab'), i.e. a monovalent-variant of a $F(ab')_2$. Such a fragment may also be single chain variable fragment (scFv).

A functional fragment does not always contain all six CDRs of a corresponding full-size antibody. It is appreciated that molecules containing three or fewer CDR regions (in some cases, even just a single CDR or a part thereof) are capable of retaining the antigen-binding activity of the antibody from which the CDR(s) are derived. For example, in Gao et aL, 1994, J. Biol. Chem., 269: 32389-93 it is described that a whole VL chain (including all three CDRs) has a high affinity for its substrate.

Molecules containing two CDR regions are described, for example, by Vaughan & Sollazzo 2001, Combinatorial Chemistry & High Throughput Screening, 4: 417-430. On page 418 (right column—3 Our Strategy for Design) a minibody including only the H1 and H2 CDR hypervariable regions interspersed within framework regions is described.

The minibody is described as being capable of binding to a target. Pessi et al., 1993, Nature, 362: 367-9 and Bianchi et al., 1994, J. Mol. Biol., 236: 649-59 are referenced by Vaughan & Sollazzo and describe the H1 and H2 minibody and its properties in more detail. In Qiu et aL, 2007, Nature Biotechnology, 25:921-9 it is demonstrated that a molecule consisting of two linked CDRs are capable of binding antigen. Quiocho 1993, Nature, 362: 293-4 provides a summary of "minibody" technology. Ladner 2007, Nature Biotechnology, 25:875-7 comments that molecules containing two CDRs are capable of retaining antigen-binding activity.

Antibody molecules containing a single CDR region are described, for example, in Laune et al., 1997, JBC, 272: 30937-44, in which it is demonstrated that a range of hexapeptides derived from a CDR display antigen-binding activity and it is noted that synthetic peptides of a complete, single, CDR display strong binding activity. In Monnet et al., 1999, JBC, 274: 3789-96 it is shown that a range of 12-mer peptides and associated framework regions have antigen-binding activity and it is commented on that a CDR3-like peptide alone is capable of binding antigen. In Heap et al., 2005, J. Gen. Virol., 86: 1791-1800 it is reported that a "micro-antibody" (a molecule containing a single CDR) is capable of binding antigen and it is shown that a cyclic peptide from an anti-HIV antibody has antigen-binding activity and function. In Nicaise et al., 2004, Protein Science, 13:1882-91 it is shown that a single CDR can confer antigen-binding activity and affinity for its lysozyme antigen.

Thus, antibody molecules having five, four, three or fewer CDRs are capable of retaining the antigen binding properties of the full-length antibodies from which they are derived.

The antibody molecule may also be a derivative of a full-length antibody or a fragment of such an antibody. When a derivative is used it should have the same antigen binding characteristics as the corresponding full-length antibody in the sense that it binds to the same epitope on the target as the full-length antibody.

Thus, by the term "antibody molecule", as used herein, we include all types of antibody molecules and functional fragments thereof and derivatives thereof, including: monoclonal antibodies, polyclonal antibodies, synthetic antibodies, recombinantly produced antibodies, multi-specific antibodies, bi-specific antibodies, human antibodies, antibodies of human origin, humanized antibodies, chimeric antibodies, single chain antibodies, single-chain Fvs (scFv), Fab fragments, F(ab')₂ fragments, F(ab') fragments, disulfide-linked Fvs (sdFv), antibody heavy chains, antibody light chains, homo-dimers of antibody heavy chains, homo-dimers of antibody light chains, heterodimers of antibody heavy chains, heterodimers of antibody light chains, antigen binding functional fragments of such homo- and heterodimers.

Further, the term "antibody molecule", as used herein, includes all classes of antibody molecules and functional fragments, including: IgG, IgG1, IgG2, IgG3, IgG4, IgA, IgM, IgD, and IgE, unless otherwise specified.

In some embodiments, the antibody is a human IgG1. The skilled person will appreciate that the mouse IgG2a and human IgG1 engage with activatory Fc gamma receptors, and share the ability to activate deletion of target cells through activation of activatory Fc gamma receptor bearing immune cells by e.g. ADCP and ADCC. As such, in embodiments where the mouse IgG2a is the preferred isotype for deletion in the mouse, human IgG1 is a preferred isotype for deletion in human in such embodiments.

As outlined above, different types and forms of antibody molecules are encompassed by the invention, and would be known to the person skilled in immunology. It is well known that antibodies used for therapeutic purposes are often modified with additional components which modify the properties of the antibody molecule.

Accordingly, we include that an antibody molecule of the invention or an antibody molecule used in accordance with the invention (for example, a monoclonal antibody molecule, and/or polyclonal antibody molecule, and/or bi-specific antibody molecule) comprises a detectable moiety and/or a cytotoxic moiety.

By "detectable moiety", we include one or more from the group comprising of: an enzyme; a radioactive atom; a fluorescent moiety; a chemiluminescent moiety; a bioluminescent moiety. The detectable moiety allows the antibody molecule to be visualised in vitro, and/or in vivo, and/or ex vivo.

By "cytotoxic moiety", we include a radioactive moiety, and/or enzyme, wherein the enzyme is a caspase, and/or toxin, wherein the toxin is a bacterial toxin or a venom; wherein the cytotoxic moiety is capable of inducing cell lysis.

We further include that the antibody molecule may be in an isolated form and/or purified form, and/or may be PEGylated. PEGylation is a method by which polyethylene glycol polymers are added to a molecule such as an antibody molecule or derivative to modify its behaviour, for example to extend its half-life by increasing its hydrodynamic size, preventing renal clearance.

As discussed above, the CDRs of an antibody bind to the antibody target. The assignment of amino acids to each CDR described herein is in accordance with the definitions according to Kabat EA et al. 1991, In "Sequences of Proteins of Immunological Interest" Fifth Edition, NIH Publication No. 91-3242, pp xv-xvii.

As the skilled person would be aware, other methods also exist for assigning amino acids to each CDR. For example, the International ImMunoGeneTics information system (IMGT(R)) (http://www.imgt.org/ and Lefranc and Lefranc "The Immunoglobulin FactsBook" published by Academic Press, 2001).

In a further embodiment, the antibody molecule of the present invention or used according to the invention is an antibody molecule that is capable of competing with the specific antibodies provided herein, for example antibody molecules comprising any of the amino acid sequences set out in for example SEQ ID NOs: 1-194 for binding to the specific target.

By "capable of competing for" we mean that the competing antibody is capable of inhibiting or otherwise interfering, at least in part, with the binding of an antibody molecule as defined herein to the specific target.

For example, such a competing antibody molecule may be capable of inhibiting the binding of an antibody molecule described herein by at least about 10%; for example at least about 20%, or at least about 30%, at least about 40%, at least about 50%, at least about 60%, at least about 70%, at least about 80%, at least about 90%, at least about 95%, about 100% and/or inhibiting the ability of the antibody described herein to prevent or reduce binding to the specific target by at least about 10%; for example at least about 20%, at least about 30%, at least about 40%, at least about 50%, at least about 60%, at least about 70%, at least about 80%, at least about 90%, at least about 95%, or about 100%.

Competitive binding may be determined by methods well known to those skilled in the art, such as Enzyme-linked immunosorbent assay (ELISA).

ELISA assays can be used to evaluate epitope-modifying or blocking antibodies. Additional methods suitable for identifying competing antibodies are disclosed in Antibodies: A Laboratory Manual, Harlow & Lane, which is incorporated herein by reference (for example, see pages 567 to 569, 574 to 576, 583 and 590 to 612, 1988, CSHL, NY, ISBN 0-87969-314-2).

It is well known that an antibody specifically binds to or interacts with a defined target molecule or antigen. That is to say, the antibody preferentially and selectively binds its target and not a molecule which is not a target.

The targets of the antibodies according to the present invention, or of the antibodies used in accordance with the invention, are expressed on the surface of cells, i.e. they are cell surface antigen, which would include an epitope (otherwise known in this context as a cell surface epitope) for the antibody. Cell surface antigen and epitope are terms that would be readily understood by one skilled in immunology or cell biology.

By "cell surface antigen", we include that the cell surface antigen is exposed on the extracellular side of the cell membrane, but may only be transiently exposed on the extracellular side of the cell membrane. By "transiently exposed", we include that the cell surface antigen may be internalized into the cell, or released from the extracellular side of the cell membrane into the extracellular space. The cell surface antigen may be released from the extracellular side of the cell membrane by cleavage, which may be mediated by a protease.

We also include that the cell surface antigen may be connected to the cell membrane, but may only be transiently associated with the cell membrane. By "transiently associated", we include that the cell surface antigen may be released from the extracellular side of the cell membrane into the extracellular space. The cell surface antigen may be released from the extracellular side of the cell membrane by cleavage, which may be mediated by a protease.

We further include that the cell surface antigen may be a peptide, or a polypeptide, or a carbohydrate, or an oligosaccharide chain, or a lipid; and/or an epitope that is present on a protein, or a glycoprotein, or a lipoprotein.

Methods of assessing protein binding are known to the person skilled in biochemistry and immunology. It would be appreciated by the skilled person that those methods could be used to assess binding of an antibody to a target and/or binding of the Fc region of an antibody to an Fc receptor; as well as the relative strength, or the specificity, or the inhibition, or prevention, or reduction in those interactions. Examples of methods that may be used to assess protein binding are, for example, immunoassays, BIAcore, western blots, radioimmunoassay (RIA) and enzyme-linked immunosorbent assays (ELISAs) (See Fundamental Immunology Second Edition, Raven Press, New York at pages 332-336 (1989) for a discussion regarding antibody specificity).

Accordingly, by "antibody molecule the specifically binds" or "target specific antibody molecule" we include that the antibody molecule specifically binds a target but does not bind to non-target, or binds to a non-target more weakly (such as with a lower affinity) than the target.

We also include the meaning that the antibody specifically binds to the target at least two-fold more strongly, or at least five-fold more strongly, or at least 10-fold more strongly, or at least 20-fold more strongly, or at least 50-fold more strongly, or at least 100-fold more strongly, or at least 200-fold more strongly, or at least 500-fold more strongly, or at least than about 1000-fold more strongly than to a non-target.

Additionally, we include the meaning that the antibody specifically binds to the target if it binds to the target with a $K_d$ of at least about $10^{-1}$ $K_d$, or at least about $10^{-2}$ $K_d$, or at least about $10^{-3}$ $K_d$, or at least about $10^{-4}$ $K_d$, or at least about $10^{-6}$ $K_d$, or at least about $10^{-6}$ $K_d$, or at least about $10^{-7}$ $K_d$, or at least about $10^{-8}$ $K_d$, or at least about $10^{-6}$ $K_d$, or at least about $10^{-10}$ $K_d$, or at least about $10^{-11}$ $K_d$, or at least about $10^{12}$ $K_d$, or at least about $10^{-13}$ $K_d$, or at least about $10^{14}$ $K_d$, or at least about $10^{-15}$ $K_d$.

As used herein, the term immune cell depleting antibody molecule or immune cell deactivating antibody molecule refers to an antibody molecule that upon administration to a patient specifically binds to a target expressed on the surface of an immune cell, wherein this binding results in depletion or deactivation of the immune cell. In some embodiments, the target is a target that is preferentially expressed on a tumour or in the tumour microenvironment.

To decide whether an antibody molecule is an immune cell depleting antibody molecule in the meaning of the present invention or not, it is possible to use an in vitro antibody-dependent cellular cytotoxicity (ADCC) or antibody-dependent cellular phagocytosis (ADCP) assay. To decide whether an antibody molecule is an immune cell depleting antibody molecule the same assay would be performed in the presence of and without the depleting antibody, which would show whether or not the depleting antibody to be tested is in fact depleting.

An ADCC assay may be done by labelling target cells with calcein AM (acetyl methyl ester), followed by the addition of diluting concentrations of antibody. Target cells is then cocultured with human peripheral blood mononuclear cells (PBMCs) at a 50:1 effector: target (E:T) ratio for 4 h at 37° C. The plate is centrifuged at 400×g for 5 min to pellet the cells, and the supernatant is transferred to a white 96-well plate. Calcein release is measured using a Varioskan (Thermo Scientific) using an excitation wavelength of 485 nm and emission wavelength, 530 nm. The percentage of maximal release is calculated as follows: % max release= (sample/triton treated)*100.

An ADCP assay may be done by labelling target cells with 5 mM carboxyfluorescein succinimidyl ester (CFSE) for 10 min at room temperature before washing in media containing foetal calf serum. CFSE-labelled targets is then opsonized with diluting concentrations of antibody before coculturing at a 1:5 E:T ratio with bone marrow derived macrophages (BMDMs) in 96-well plates for 1 h at 37° C. BMDMs are then labelled with anti-F4/80—allophycocyanin for 15 min at room temperature and washed with PBS twice. Plates are kept on ice, wells are scraped to collect BMDMs, and phagocytosis is assessed by flow cytometry using a FACSCalibur (BD) to determine the percentage of F4/80+CFSE+ cells within the F4/80+ cell population.

It is also possible to use a method as described by Cleary et al in J Immunol, Apr. 12, 2017, 1601473.

In some embodiments the antibody molecule that specifically binds FcγRIIb is a human antibody.

In some embodiments, the antibody molecule that specifically binds FcγRIIb is an antibody of human origin, i.e. an originally human antibody that has been modified as described herein.

In some embodiments, the antibody molecule that specifically binds FcγRIIb is a humanized antibody, i.e. an originally non-human antibody that has been modified to increase its similarity to a human antibody. The humanized antibodies may, for example, be of murine antibodies or lama antibodies.

In some embodiments, the antibody molecule that specifically binds FcγRIIb comprises the following constant regions (CH and CL):

IgG1-CH

[SEQ ID NO: 1]
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLIC

LVKGFYPSDIAVEWESNGQPENNYKTTPPVLDSDGSFFLYSKLTVDKSRW

QQGNVFSCSVMHEALHNHYTQKSLSLSPGK

```
IgG1-CL
                                          [SEQ ID NO: 2]
QPKAAPSVTLFPPSSEELQANKATLVCLISDFYPGAVTVAWKADSSPVKA

GVETTTPSKQSNNKYAASSYLSLTPEQWKSHRSYSCQVTHEGSTVEKTVA

PTECS
```

These constant regions (SEQ ID NO: 1 and SEQ ID NO: 2) are of human origin. The Fc region is further modified for reduced binding to Fcγ receptors via its Fc region. As mentioned herein, it is in some embodiments preferred that SEQ ID NO: 1 has been aglycosylated through an N297Q substitution, and the IgG1-CH has then the following CH sequence [SEQ ID NO: 195], with the 297 Q residue is marked in bold:

```
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVS

HEDPEVKFNWYVDGVEVHNAKTKPREEQYQSTYRVVSVLTVLHQDWLNGK

EYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSRW

QQGNVFSCSVMHEALHNHYTQKSLSLSPGK
```

In some embodiments and/or examples, murine antibody molecules are used. These may also be used for surrogate antibodies. These may then comprise the following constant regions (CH and CL):

```
CH
                                        [SEQ ID NO: 196]
AKTTAPSVYPLAPVCGDTTGSSVTLGCLVKGYFPEPVTLTWNSGSLSSGV

HTFPAVLQSDLYTLSSSVTVTSSTWPSQSITCNVAHPASSTKVDKKIEPR

GPTIKPCPPCKCPAPNLLGGPSVFIFPPKIKDVLMISLSPIVTCVVVDVS

EDDPDVQISWFVNNVEVHTAQTQTHREDYASTLRVVSALPIQHQDWMSGK

EFKCKVNNKDLPAPIERTISKPKGSVRAPQVYVLPPPEEEMTKKQVTLTC

MVTDFMPEDIYVEWTNNGKTELNYKNTEPVLDSDGSYFMYSKLRVEKKNW

VERNSYSCSVVHEGLHNHHTTKSFSRTPGK

CL
                                        [SEQ ID NO: 197]
QPKSSPSVTLFPPSSEELETNKATLVCTITDFYPGVVTVDWKVDGTPVTQ

GMETTQPSKQSNNKYMASSYLTLTARAWERHSSYSCQVTHEGHTVEKSLS

RADCS
```

These constant regions (SEQ ID NO: 196 and SEQ ID NO: 197) are thus of murine origin. SEQ ID NO: 196 comprises the N297A mutation (the 297 A residue is marked in bold in the sequence above). This N297A mutation in the murine sequence corresponds to the N297Q mutation in the human sequence.

In some embodiments, the antibody molecule that specifically binds FcγRIIb comprises one or more sequences of the following clones:

```
Antibody clone: 1A01
1A01-VH
                                          [SEQ ID NO: 3]
EVQLLESGGGLVQPGGSLRLSCAASGFTFSDYYMNWIRQTPGKGLEWVSL

IGWDGGSTYYADSVKGRFTISRDNSENTLYLQMNSLRAEDTAVYYCARAY

SGYELDYWGQGTLVTVSS

1A01-VL
                                         [SEQ ID NO: 27]
QSVLTQPPSASGTPGQRVTISCSGSSSNIGNNAVNWYQQLPGTAPKLLIY

DNNNRPSGVPDRFSGSKSGTSASLAISGLRSEDEADYYCAAWDDSLNASI

FGGGTKLTVLG

CDR regions
CDRH1:
                                         [SEQ ID NO: 51]
DYYMN CDRH2:
                                         [SEQ ID NO: 52]
LIGWDGGSTYYADSVKG

CDRH3:
                                         [SEQ ID NO: 53]
AYSGYELDY

CDRL1:
                                         [SEQ ID NO: 54]
SGSSSNIGNNAVN

CDRL2:
                                         [SEQ ID NO: 55]
DNNNRPS

CDRL3:
                                         [SEQ ID NO: 56]
AAWDDSLNASI

Antibody clone: 1B07
1B07-VH
                                          [SEQ ID NO: 4]
EVQLLESGGGLVQPGGSLRLSCAASGFTFSSYGMHWVRQAPGKGLEWVAF

TRYDGSNKYYADSVRGRFTISRDNSKNTLYLQMNSLRAEDTAVYYCAREN

IDAFDVWGQGTLVTVSS

1B07-VL
                                         [SEQ ID NO: 28]
QSVLTQPPSASGTPGQRVTISCSGSSSNIGNNAVNWYQQLPGTAPKLLIY

DNQQRPSGVPDRFSGSKSGTSASLAISGLRSEDEADYYCEAWDDRLFGPV

FGGGTKLTVLG

CDR regions
CDRH1:
                                         [SEQ ID NO: 57]
SYGMH CDRH2:
                                         [SEQ ID NO: 58]
FTRYDGSNKYYADSVRG

CDRH3:
                                         [SEQ ID NO: 59]
ENIDAFDV

CDRL1:
                                         [SEQ ID NO: 60]
SGSSSNIGNNAVN
```

CDRL2:
DNQQRPS [SEQ ID NO: 61]

CDRL3:
WDDRLFGPV [SEQ ID NO: 62]

Antibody clone: 1C04
1C04-VH [SEQ ID NO: 5]
EVQLLESGGGLVQPGGSLRLSCAASGFTFSSYAMSWVRQAPGKGLEWVSS
ISDSGAGRYYADSVEGRFTISRDNSKNTLYLQMNSLRAEDTAVYYCARTH
DSGELLDAFDIWGQGTLVTVSS 1C04-VL [SEQ ID NO: 29]
QSVLTQPPSASGTPGQRVTISCSGSSSNIGSNHVLWYQQLPGTAPKLLIY
GNSNRPSGVPDRFSGSKSGTSASLAISGLRSEDEADYYCAAWDDSLNGWV
FGGGTKLTVLG CDR regions
CDRH1:
SYAMS [SEQ ID NO: 63]

CDRH2:
SISDSGAGRYYADSVEG [SEQ ID NO: 64]

CDRH3:
THDSGELLDAFDI [SEQ ID NO: 65]

CDRL1:
SGSSSNIGSNHVL [SEQ ID NO: 66]

CDRL2:
GNSNRPS [SEQ ID NO: 67]

CDRL3:
AAWDDSLNGWV [SEQ ID NO: 68]

Antibody clone: 1E05
1E05-VH [SEQ ID NO: 6]
EVQLLESGGGLVQPGGSLRLSCAASGFTFSTYAMNWVRQVPGKGLEWVAV
ISYDGSNKNYVDSVKGRFTISRDNSKNTLYLQMNSLRAEDTAVYYCARNF
DNSGYAIPDAFDIWGQGTLVTVSS 1E05-VL [SEQ ID NO: 30]
QSVLTQPPSASGTPGQRVTISCTGSSSNIGAGYDVHWYQQLPGTAPKLLI
YDNNSRPSGVPDRFSGSKSGTSASLAISGLRSEDEADYYCAAWIDDSLGG
PVFGGGTKLTVLG CDR regions
CDRH1:
TYAMN [SEQ ID NO: 69]

CDRH2:
VISYDGSNKNYVDSVKG [SEQ ID NO: 70]

CDRH3:
NFDNSGYAIPDAFDI [SEQ ID NO: 71]

CDRL1:
TGSSSNIGAGYDVH [SEQ ID NO: 72]

CDRL2:
DNNSRPS [SEQ ID NO: 73]

CDRL3:
AAWDDSLGGPV [SEQ ID NO: 74]

Antibody clone: 2A09
2A09-VH [SEQ ID NO: 7]
EVQLLESGGGLVQPGGSLRLSCAASGFTFSNAWMSWVRQAPGKGLEWVAY
ISRDADITHYPASVKGRFTISRDNSKNTLYLQMNSLRAEDTAVYYCTTGF
DYAGDDAFDIWGQGTLVTVSS 2A09-VL [SEQ ID NO: 31]
QSVLTQPPSASGTPGQRVTISCSGSSSNIGSNAVNWYQQLPGTAPKLLIY
GNSDRPSGVPDRFSGSKSGTSASLAISGLRSEDEADYYCAAWDDSLNGRW
VFGGGTKLTVLG CDR regions
CDRH1:
NAWMS [SEQ ID NO: 75]

CDRH2:
YISRDADITHYPASVKG [SEQ ID NO: 76]

CDRH3:
GFDYAGDDAFDI [SEQ ID NO: 77]

CDRL1:
SGSSSNIGSNAVN [SEQ ID NO: 78]

CDRL2:
GNSDRPS [SEQ ID NO: 79]

CDRL3:
AAWDDSLNGRWV [SEQ ID NO: 80]

Antibody clone: 2B08
2B08-VH [SEQ ID NO: 8]
EVQLLESGGGLVQPGGSLRLSCAASGFTFSDYYMSWVRQAPGKGLEWVAL
IGHDGNNKYYLDSLEGRFTISRDNSKNTLYLQMNSLRAEDTAVYYCARAT
DSGYDLLYWGQGTLVTVSS 2B08-VL [SEQ ID NO: 32]
QSVLTQPPSASGTPGQRVTISCSGSSSNIGNNAVNWYQQLPGTAPKLLIY
YDDLLPSGVPDRFSGSKSGTSASLAISGLRSEDEADYYCTTWDDSLSGVV
FGGGTKLTVLG CDR regions
CDRH1:
DYYMS [SEQ ID NO: 81]

CDRH2:
LIGHDGNNKYYLDSLEG [SEQ ID NO: 82]

-continued

CDRH3:
ATDSGYDLLY [SEQ ID NO: 83]

CDRL1:
SGSSSNIGNNAVN [SEQ ID NO: 84]

CDRL2:
YDDLLPS [SEQ ID NO: 85]

CDRL3:
TTWDDSLSGVV [SEQ ID NO: 86]

Antibody clone: 2E8-VH
2E8-VH [SEQ ID NO: 9]
EVQLLESGGGLVQPGGSLRLSCAASGFTFSDYYMSWIRQAPGKGLEWVSA
IGFSDDNTYYADSVKGRFTISRDNSKNTLYLQMNSLRAEDTAVYYCAGGD
GSGWSFWGQGTLVTVSS 2E8-VL [SEQ ID NO: 33]
QSVLTQPPSASGTPGQRVTISCSGSSSNIGNNAVNWYQQLPGTAPKLLIY
DNNKRPSGVPDRFSGSKSGTSASLAISGLRSEDEADYYCATWDDSLRGWV
FGGGTKLTVLG CDR regions
CDRH1:
DYYMS [SEQ ID NO: 87]

CDRH2:
AIGFSDDNTYYADSVKG [SEQ ID NO: 88]

CDRH3:
GDGSGWSF [SEQ ID NO: 89]

CDRL1:
SGSSSNIGNNAVN [SEQ ID NO: 90]

CDRL2:
DNNKRPS [SEQ ID NO: 91]

CDRL3:
ATWDDSLRGWV [SEQ ID NO: 92]

Antibody clone: 5C04
5C04-VH [SEQ ID NO: 10]
EVQLLESGGGLVQPGGSLRLSCAASGFTFSNYGMHWVRQAPGKGLEWVAV
ISYDGSNKYYADSVKGRFTISRDNSKNTLYLQMNSLRAEDTAVYYCAREW
RDAFDIWGQGTLVTVSS 5C04-VL [SEQ ID NO: 34]
QSVLTQPPSASGTPGQRVTISCTGSSSNIGAGYDVHWYQQLPGTAPKLLI
YSDNQRPSGVPDRFSGSKSGTSASLAISGLRSEDEADYYCAAWDDSLSGS
WVFGGGTKLTVLG CDR regions
CDRH1:
NYGMH [SEQ ID NO: 93]

CDRH2:
VISYDGSNKYYADSVKG [SEQ ID NO: 94]

CDRH3:
WRDAFDI [SEQ ID NO: 95]

CDRL1:
TGSSSNIGAGYDVH [SEQ ID NO: 96]

CDRL2:
SDNQRPS [SEQ ID NO: 97]

CDRL3:
AAWDDSLSGSWV [SEQ ID NO: 98]

Antibody clone: 5C05
5C05-VH [SEQ ID NO: 11]
EVQLLESGGGLVQPGGSLRLSCAASGFTFSTYGMHWVRQAPGKGLEWVAV
ISYDGSNKYYADSVKGRFTISRDNSKNTLYLQMNSLRAEDTAVYYCAREN
FDAFDVWGQGTLVTVSS 5C05-VL [SEQ ID NO: 35]
QSVLTQPPSASGTPGQRVTISCTGSSSNIGAGYDVHWYQQLPGTAPKLLI
YSNSQRPSGVPDRFSGSKSGTSASLAISGLRSEDEADYYCAAWDDSLNGQ
VVFGGGTKLTVLG CDR regions
CDRH1:
TYGMH [SEQ ID NO: 99]

CDRH2:
VISYDGSNKYYADSVKG [SEQ ID NO: 100]

CDRH3:
ENFDAFDV [SEQ ID NO: 101]

CDRL1:
TGSSSNIGAGYDVH [SEQ ID NO: 102]

CDRL2:
SNSQRPS [SEQ ID NO: 103]

CDRL3:
AAWDDSLNGQVV [SEQ ID NO: 104]

Antibody clone: 5D07
5D07-VH [SEQ ID NO: 12]
EVQLLESGGGLVQPGGSLRLSCAASGFTFSTYGMHWVRQAPGKGLEWVAV
IAYDGSKKDYADSVKGRFTISRDNSKNTLYLQMNSLRAEDTAVYYCAREY
RDAFDIWGQGTLVTVSS 5D07-VL [SEQ ID NO: 36]
QSVLTQPPSASGTPGQRVTISCTGSSSNIGAGYDVHWYQQLPGTAPKLLI
YGNSNRPSGVPDRFSGSKSGTTASLAISGLRSEDEADYYCAAWDDSVSGW
MFGGGTKLTVLG CDR regions
CDRH1:
[SEQ ID NO: 105]
TYGMH

CDRH2:
[SEQ ID NO: 106]
VIAYDGSKKDYADSVKG

CDRH3:
[SEQ ID NO: 107]
EYRDAFDI

CDRL1:
[SEQ ID NO: 108]
TGSSSNIGAGYDVH

CDRL2:
[SEQ ID NO: 109]
GNSNRPS

CDRL3:
[SEQ ID NO: 110]
AAWDDSVSGWM

Antibody clone: 5E12
5E12-VH
[SEQ ID NO: 13]
EVQLLESGGGLVQPGGSLRLSCAASGFTFSSYGMHWVRQAPGKGLEWVAVISYDGINKDYADSMKGRFTISRDNSKNTLYLQMNSLRAEDTAVYYCARERKDAFDIWGQGTLVTVSS 5E12-VL
[SEQ ID NO: 37]
QSVLTQPPSASGTPGQRVTISCTGSSSNIGAGYDVHWYQQLPGTAPKLLIYSNNQRPSGVPDRFSGSKSGTSASLAISGLRSEDEADYYCATWDDSLNGLVFGGGTKLTVLG CDR regions
CDRH1:
[SEQ ID NO: 111]
SYGMH

CDRH2:
[SEQ ID NO: 112]
VISYDGINKDYADSMKG

CDRH3:
[SEQ ID NO: 113]
ERKDAFDI

CDRL1:
[SEQ ID NO: 114]
TGSSSNIGAGYDVH

CDRL2:
[SEQ ID NO: 115]
SNNQRPS

CDRL3:
[SEQ ID NO: 116]
ATWDDSLNGLV

Antibody clone: 5G08
5G08-VH
[SEQ ID NO: 14]
EVQLLESGGGLVQPGGSLRLSCAASGFTFNNYGMHWVRQAPGKGLEWVAVISYDGSNRYYADSVKGRFTMSRDNSKNTLYLQMNSLRAEDTAVYYCARDRWNGMDVWGQGTLVTVSS 5G08-VL
[SEQ ID NO: 38]
QSVLTQPPSASGTPGQRVTISCSGSSSNIGAGYDVHWYQQLPGTAPKLLIYANNQRPSGVPDRFSGSKSGTSASLAISGLRSEDEADYYCAAWDDSLNGPWVFGGGTKLTVLG CDR regions
CDRH1:
[SEQ ID NO: 117]
NYGMH

CDRH2:
[SEQ ID NO: 118]
VISYDGSNRYYADSVKG

CDRH3:
[SEQ ID NO: 119]
DRWNGMDV

CDRL1:
[SEQ ID NO: 120]
SGSSSNIGAGYDVH

CDRL2:
[SEQ ID NO: 121]
ANNQRPS

CDRL3:
[SEQ ID NO: 122]
AAWDDSLNGPWV

Antibody clone: 5H06
5H06-VH
[SEQ ID NO: 15]
EVQLLESGGGLVQPGGSLRLSCAASGFTFSSYGMHWVRQAPGKGLEWVAVISYDGSDTAYADSVKGRFTISRDNSKNTLYLQMNSLRAEDTAVYYCARDHSVIGAFDIWGQGTLVTVSS 5H06-VL
[SEQ ID NO: 39]
QSVLTQPPSASGTPGQRVTISCSGSSSNIGSNTVNWYQQLPGTAPKLLIYDNNKRPSGVPDRFSGSKSGTSASLAISGLRSEDEEADYYCSSYAGSNNVVFGGGTKLTVLG CDR regions
CDRH1:
[SEQ ID NO: 123]
SYGMH

CDRH2:
[SEQ ID NO: 124]
VISYDGSDTAYADSVKG

CDRH3:
[SEQ ID NO: 125]
DHSVIGAFDI

CDRL1:
[SEQ ID NO: 126]
SGSSSNIGSNTVN

CDRL2:
[SEQ ID NO: 127]
DNNKRPS

CDRL3:
[SEQ ID NO: 128]
SSYAGSNNVV

-continued

Antibody clone: 6A09
6A09-VH
[SEQ ID NO: 16]
EVQLLESGGGLVQPGGSLRLSCAASGFTFSSYGMHWVRQAPGKGLEWVAV
TSYDIGNTKYYANSVKGRFTISRDNSKNTLYLQMNSLRAEDTAVYYCARE
DCGGDCFDYWGQGTLVTVSS 6A09-VL
[SEQ ID NO: 40]
QSVLTQPPSASGTPGQRVTISCTGSSSNIGAGYDVHWYQQLPGTAPKLLI
YGNSNRPSGVPDRFSGSKSGTSASLAISGLRSEDEADYYCAAWDDSLNEG
VFGGGTKLTVLG CDR regions
CDRH1:
[SEQ ID NO: 129]
SYGMH

CDRH2:
[SEQ ID NO: 130]
VTSYDGNTKYYANSVKG

CDRH3:
[SEQ ID NO: 131]
EDCGGDCFDY

CDRL1:
[SEQ ID NO: 132]
TGSSSNIGAGYDVH

CDRL2:
[SEQ ID NO: 133]
GNSNRPS

CDRL3:
[SEQ ID NO: 134]
AAWDDSLNEGV

Antibody clone: 6B01
6B01-VH
[SEQ ID NO: 17]
EVQLLESGGGLVQPGGSLRLSCAASGFTFSNYGMHWVRQAPGKGLEWVAV
ISYDGSNKYYADSVKGRFTISRDNSKNTLYLQMNSLRAEDTAVYYCARDQ
LGEAFDIWGQGTLVTVSS 6B01-VL
[SEQ ID NO: 41]
QSVLTQPPSASGTPGQRVTISCTGSSSNIGAGYDVHWYQQLPGTAPKLLI
YDNNKRPSGVPDRFSGSKSGTSASLAISGLRSEDEADYYCATWDDSLSGP
VFGGGTKLTVLG CDR regions
CDRH1:
[SEQ ID NO: 135]
NYGMH

CDRH2:
[SEQ ID NO: 136]
VISYDGSNKYYADSVKG

CDRH3:
[SEQ ID NO: 137]
DQLGEAFDI

CDRL1:
[SEQ ID NO: 138]
TGSSSNIGAGYDVH

CDRL2:
[SEQ ID NO: 139]
DNNKRPS

-continued

CDRL3:
[SEQ ID NO: 140]
ATWDDSLSGPV

Antibody clone: 6C11
6C11-VH
[SEQ ID NO: 18]
EVQLLESGGGLVQPGGSLRLSCAASGFTFDDYGMSWVRQAPGKGLEWVSA
ISGSGSSTYYADSVKGRFTISRDNSKNTLYLQMNSLRAEDTAVYYCAGGD
IDYFDYWGQGTLVTVSS 6C11-VL
[SEQ ID NO: 42]
QSVLTQPPSASGTPGQRVTISCTGSSSNFGAGYDVHWYQQLPGTAPKLLI
YENNKRPSGVPDRFSGSKSGTSASLAISGLRSEDEADYYCAAWDDSLNGP
VFGGGTKLTVLG CDR regions
CDRH1:
[SEQ ID NO: 141]
DYGMS

CDRH2:
[SEQ ID NO: 142]
AISGSGSSTYYADSVKG

CDRH3:
[SEQ ID NO: 143]
GDIDYFDY

CDRL1:
[SEQ ID NO: 144]
TGSSSNFGAGYDVH

CDRL2:
[SEQ ID NO: 145]
ENNKRPS

CDRL3:
[SEQ ID NO: 146]
AAWDDSLNGPV

Antibody clone: 6C12
6C12-VH
[SEQ ID NO: 19]
EVQLLESGGGLVQPGGSLRLSCAASGFTFSSYGMHWVRQAPGKGLEWVAV
ISYDGSNKYYADSVKGRFTISRDNSKNTLYLQMNSLRAEDTAVYYCARER
RDAFDIWGQGTLVTVSS 6C12-VL
[SEQ ID NO: 43]
QSVLTQPPSASGTPGQRVTISCIGSSSNIGAGYDVHWYQQLPGTAPKLLI
YSDNQRPSGVPDRFSGSKSGTSASLAISGLRSEDEADYYCATWDSDTPVF
GGGTKLTVLG CDR regions
CDRH1:
[SEQ ID NO: 147]
SYGMH

CDRH2:
[SEQ ID NO: 148]
VISYDGSNKYYADSVKG

CDRH3:
[SEQ ID NO: 149]
ERRDAFDI

CDRL1:
[SEQ ID NO: 150]
TGSSSNIGAGYDVH

CDRL2:
[SEQ ID NO: 151]
SDNQRPS

CDRL3:
[SEQ ID NO: 152]
ATWDSDTPV

Antibody clone: 6D01
6D01-VH
[SEQ ID NO: 20]
EVQLLESGGGLVQPGGSLRLSCAASGFTFSSYGMHWVRQAPGKGLEWVAVISYDGSNKYYADSVKGRFTISRDNSKNTLYLQMNSLRAEDTAMYYCARDHSAAGYFDYWGQGTLVTVSS 6D01-VL
[SEQ ID NO: 44]
QSVLTQPPSASGTPGQRVTISCSGSSSNIGSNTVNWYQQLPGTAPKLLIYGNSIRPSGGPDRFSGSKSGTSASLAISGLRSEDEADYYCASWDDSLSSPVFGGGTKLTVLG CDR regions
CDRH1:
[SEQ ID NO: 153]
SYGMH

CDRH2:
[SEQ ID NO: 154]
VISYDGSNKYYADSVKG

CDRH3:
[SEQ ID NO: 155]
DHSAAGYFDY

CDRL1:
[SEQ ID NO: 156]
SGSSSNIGSNTVN

CDRL2:
[SEQ ID NO: 157]
GNSIRPS

CDRL3:
[SEQ ID NO: 158]
ASWDDSLSSPV

Antibody clone: 6G03
6G03-VH
[SEQ ID NO: 21]
EVQLLESGGGLVQPGGSLRLSCAASGFTFGSYGMHWVRQAPGKGLEWVSGISWDSAIIDYAGSVKGRFTISRDNSKNTLYLQMNSLRAEDTAVYYCAKDEAAAGAFDIWGQGTLVTVSS 6G03-VL
[SEQ ID NO: 45]
QSVLTQPPSASGTPGQRVTISCTGSSSNIGAYDVHWYQQLPGTAPKLLIYGNTDRPSGVPDRFSGSKSGTSASLAISGLRSEDEADYYCAAWDDSLSGPVVFGGGTKLTVLG CDR regions
CDRH1:
[SEQ ID NO: 159]
SYGMH

CDRH2:
[SEQ ID NO: 160]
GISWDSAIIDYAGSVKG

CDRH3:
[SEQ ID NO: 161]
DEAAAGAFDI

CDRL1:
[SEQ ID NO: 162]
TGSSSNIGAYDVH

CDRL2:
[SEQ ID NO: 163]
GNTDRPS

CDRL3:
[SEQ ID NO: 164]
AAWDDSLSGPVV

Antibody clone: 6G08
6G08-VH
[SEQ ID NO: 22]
EVQLLESGGGLVQPGGSLRLSCAASGFTLSSYGISWVRQAPGKGLEWVSGISGSGGNTYYADSVKGRFTISRDNSKNTLYLQMNSLRAEDTAVYYCASSVGAYANDAFDIWGQGTLVTVSS 6G08-VL
[SEQ ID NO: 46]
QSVLTQPPSASGTPGQRVTISCTGSSSNIGAYDVHWYQQLPGTAPKLLIYGDTNRPSGVPDRFSGSKSGTSASLAISGLRSEDEADYYCAAWDDSLNGPVFGGGTKLTVLG CDR regions
CDRH1:
[SEQ ID NO: 165]
SYGIS

CDRH2:
[SEQ ID NO: 166]
GISGSGGNTYYADSVKG

CDRH3:
[SEQ ID NO: 167]
SVGAYANDAFDI

CDRL1:
[SEQ ID NO: 168]
TGSSSNIGAYDVH

CDRL2:
[SEQ ID NO: 169]
GDTNRPS

CDRL3:
[SEQ ID NO: 170]
AAWDDSLNGPV

Antibody clone: 6G11
6G11-VH
[SEQ ID NO: 23]
EVQLLESGGGLVQPGGSLRLSCAASGFTFSSYGMHWVRQAPGKGLEWMAVISYDGSNKYYADSVKGRFTISRDNSKNTLYLQMNSLRAEDTAVYYCARELYDAFDIWGQGTLVTVSS 6G11-VL
[SEQ ID NO: 47]
QSVLTQPPSASGTPGQRVTISCTGSSSNIGAYDVHWYQQLPGTAPKLLIYADDHRPSGVPDRFSGSKSGTSASLAISGLRSEDEADYYCASWDDSQRAVIFGGGTKLTVLG CDR regions
CDRH1:
[SEQ ID NO: 171]
SYGMH

CDRH2:
[SEQ ID NO: 172]
VISYDGSNKYYADSVKG

```
CDRH3:
                                         [SEQ ID NO: 173]
ELYDAFDI

CDRL1:
                                         [SEQ ID NO: 174]
TGSSSNIGAGYDVH

CDRL2:
                                         [SEQ ID NO: 175]
ADDHRPS

CDRL3:
                                         [SEQ ID NO: 176]
ASWDDSQRAVI

Antibody clone: 6H08
6H08-VH
                                         [SEQ ID NO: 24]
EVQLLESGGGLVQPGGSLRLSCAASGFTFNNYGMHWVRQAPGKGLEWVAV
ISYDGSNKYYADSVKGRFTISKDNSKNTLYLQMNSLRAEDTAVYYCAREY
KDAFDIWGQGTLVTVSS 6H08-VL
                                         [SEQ ID NO: 48]
QSVLTQPPSASGTPGQRVTISCTGSSSNIGSNTVNWYQQLPGTAPKLLIY
DNNKRPSGVPDRFSGSKSGTSASLAISGLRSEDEADYYCQAWGTGIRVFG
GGTKLTVLG CDR regions
CDRH1:
                                         [SEQ ID NO: 177]
NYGMH CDRH2:
                                         [SEQ ID NO: 178]
VISYDGSNKYYAD SVKG

CDRH3:
                                         [SEQ ID NO: 179]
EYKDAFDI

CDRL1:
                                         [SEQ ID NO: 180]
TGSSSNIGSNTVN

CDRL2:
                                         [SEQ ID NO: 181]
DNNKRPS

CDRL3:
                                         [SEQ ID NO: 182]
QAWGTGIRV

Antibody clone: 7C07
7C07-VH
                                         [SEQ ID NO: 25]
EVQLLESGGGLVQPGGSLRLSCAASGFTFSSYGMHWVRQAPGKGLEWVAV
ISYDGSNKYYADSVKGRFTISRDNSQNTLYLQMNSLRAEDTAVYYCAREF
GYIILDYWGQGTLVTVSS 7C07-VL
                                         [SEQ ID NO: 49]
QSVLTQPPSASGTPGQRVTISCSGSSSNIGSNTVNWYQQLPGTAPKLLI
YRDYERPSGVPDRFSGSKSGTSASLAISGLRSEDEADYYCMAWDDSLSG
VVFGGGTKLTVLG CDR regions
CDRH1:
                                         [SEQ ID NO: 183]
SYGMH CDRH2:
                                         [SEQ ID NO: 184]
VISYDGSNKYYADSVKG

CDRH3:
                                         [SEQ ID NO: 185]
EFGYIILDY

CDRL1:
                                         [SEQ ID NO: 186]
SGSSSNIGSNTVN

CDRL2:
                                         [SEQ ID NO: 187]
RDYERPS

CDRL3:
                                         [SEQ ID NO: 188]
MAWDDSLSGVV

Antibody clone: 4B02
4B02-VH
                                         [SEQ ID NO: 26]
EVQLLESGGGLVQPGGSLRLSCAASGFTFSNHGMHWVRQAPGKGLEWVAV
ISYDGTNKYYADSVRGRFTISRDNSKNTLYLQMNSLRAEDTAVYYCARET
WDAFDVWGQGTLVTVSS 4B02-VL
                                         [SEQ ID NO: 50]
QSVLTQPPSASGTPGQRVTISCSGSSSNIGSNNANWYQQLPGTAPKLLIY
DNNKRPSGVPDRFSGSKSGTSASLAISGLRSEDEADYYCQAWDSSTVVFG
GGTKLTVLG CDR regions
CDRH1:
                                         [SEQ ID NO: 189]
NHGMH CDRH2:
                                         [SEQ ID NO: 190]
VISYDGTNKYYADSVRG

CDRH3:
                                         [SEQ ID NO: 191]
ETWDAFDV

CDRL1:
                                         [SEQ ID NO: 192]
SGSSSNIGSNNAN

CDRL2
                                         [SEQ ID NO: 193]
DNNKRPS

CDRL3:
                                         [SEQ ID NO: 194]
QAWDSSTVV
```

In some embodiments, which are sometimes preferred embodiments, the antibody molecule that specifically binds FcγRIIb comprises the following CDR regions: SEQ ID NO: 171 (CDRH1), SEQ ID NO: 172 (CDRH2), SEQ ID NO: 173 (CDRH3), SEQ ID NO: 174 (CDRL1), SEQ ID NO: 175 (CDRL2) and SEQ ID NO: 176 (CDRL3), i.e. the CDR regions of clone 6G11.

In some embodiments, which are sometimes preferred embodiments, the antibody molecule that specifically binds FcγRIIb comprises the following constant regions: SEQ ID NO: 1 (CH) and SEQ ID NO: 2 (CL) and the following variable regions: SEQ ID NO: 23 (VL) and SEQ ID NO: 47 (VH) i.e. the constant and variable regions of clone 6G11, which antibody molecule has further been modified to have reduced binding to Fcγ receptors via its Fc region. In some embodiments, which are sometimes preferred embodiments, the antibody molecule that specifically binds FcγRIIb comprises the following constant regions: SEQ ID NO: 195 (CH) and SEQ ID NO: 2 (CL) and the following variable regions: SEQ ID NO: 23 (VL) and SEQ ID NO: 47 (VH) i.e. the constant and variable regions of clone 6G11 including the N297Q mutation.

In some embodiments, the immune cell depleting or deactivating antibody molecule is a human antibody molecule or an antibody molecule of human origin. In some such embodiments, the human antibody molecule or antibody molecule of human origin is an IgG antibody. In some such embodiments the human antibody molecule or antibody molecule of human origin is an IgG1 or an IgG2 antibody.

In some embodiments, the immune cell depleting or deactivating antibody molecule is a humanized antibody molecule.

In some embodiments the immune cell depleting or deactivating antibody molecule is a chimeric antibody.

As mentioned above, the immune cell depleting or deactivating antibody must have the ability to engage FcγRs.

The target that immune cell depleting or deactivating antibody molecule in accordance with the present invention binds to may be selected from the group consisting CTLA-4, 4-1BB, OX40, TNFR2, PD-L1, IL-2R, and GITR.

In some embodiments of the present invention, the target that immune cell depleting or deactivating antibody molecule in accordance with the present invention binds to is CTLA-4. CTLA-4, or CTLA4, which stands for cytotoxic T-lymphocyte-associate protein 4, is also known as CD152. It is a protein receptor, that functioning as an immune checkpoint, downregulates immune responsive. CTLA4 is constitutively expressed in regulatory T cells but only upregulated in conventional T cells after activation—a phenomenon which is particularly notable in cancers. In some such embodiments the immune cell depleting antibody molecule is ipilimumab (such as Yervoy® from Bristol-Myers Squibb). In some such embodiments the immune cell depleting antibody molecule is tremelimumab (formerly denoted ticilimumab and, CP-675,206), which is a fully human monoclonal antibody against CTLA-4.previously in development by Pfizer and now in clinical development by MedImmune.

In some embodiments of the present invention, at least one target is 4-1BB, which is also denoted CD137 and tumour necrosis factor receptor superfamily member 9 (TNFRSF9). 4-1BB is expressed on Tregs following activation of CD4+ and CD8+ T cells and its ligation is required for optimal protective CD8 T cell responses against viruses and B cell lymphoma in mice. Anti-4-1BB specific antibodies enhance the proliferation and survival of antigen-stimulated T cells in vitro and, similar to anti-CD40, anti-4-1BB mAb promote anti-tumour immunity in pre-clinical cancer models dependent largely on CD8 T cells. In some such embodiments the immune cell depleting antibody molecule is urelumab, a humanized agonistic IgG4 monoclonal antibody developed by Bristol-Myers Squibb. In some such embodiments the immune cell depleting antibody molecule is utomilumab.(also denoted (PF-05082566, PF-2566, and PF-5082566), a human HuCAL mAb agonist of 4-1BB developed by Pfizer.

In some embodiments of the present invention, at least one target is OX40. OX40, also known as tumour necrosis factor receptor superfamily, member 4 (TNFRSF4), and CD134, is a secondary co-stimulatory immune checkpoint molecule. In some such embodiments the immune cell depleting antibody molecule is MEDI6469 (9B12), MEDI0562, PF-04518600, INCAGN01949, BMS-986178, MOXR0916, GSK3174998, MEDI6383 (see e.g. Table 1 of Buchan et al., Blood 2018 131:39-48).

In some embodiments of the present invention, at least one target is TNFR-2. Tumour necrosis factor receptor 2 (TNFR-2 or TNFR2), also known as tumour necrosis factor receptor superfamily member 1B (TNFRSF1B) and CD120b, which is a membrane receptor that binds tumour necrosis factor-alpha (TNFα).

In some embodiments of the present invention, the target that immune cell depleting or deactivating antibody molecule in accordance with the present invention binds to is programmed death-ligand 1 (PD-L1), also known as CD274 or B7 homolog 1 (B7-H1).

In some embodiments of the present invention, at least one target is IL-2R. IL-2R is also known as CD25 and is highly expressed primarily on regulatory T cells.

In some embodiments of the present invention, at least one target is GITR. GITR is a member of the TNFSFR and is also primarily expressed on regulatory T cells.

In some embodiments the antibody molecule that specifically binds FcγRIIb and the immune cell depleting or deactivating antibody molecule are administered simultaneously to the patient, meaning that they are either administered together at one or separately very close in time to each other.

In some embodiments the antibody molecule that specifically binds FcγRIIb is administered to the patient prior to administration of the immune cell depleting or deactivating antibody molecule. Such sequential administration may be achieved by temporal separation of the two antibodies. Alternatively, or in combination with the first option, the sequential administration may also be achieved by spatial separation of the two antibody molecules, by administration of the antibody molecule that specifically binds FcγRIIb in a way, such as intratumoural, so that it reaches the cancer prior to the immune cell depleting antibody molecule, which is then administered in a way, such as systemically, so that it reaches the cancer after the antibody molecule that specifically binds FcγRIIb.

In some embodiments the immune cell depleting antibody is administered to the patient prior to administration of the antibody molecule that specifically binds FcγRIIb. Such sequential administration may be achieved as described above.

It would be known to the person skilled in medicine, that medicines can be modified with different additives, for example to change the rate in which the medicine is absorbed by the body; and can be modified in different forms, for example to allow for a particular administration route to the body.

Accordingly, we include that the composition, and/or antibody, and/or medicament of the invention may be combined with an excipient and/or a pharmaceutically acceptable carrier and/or a pharmaceutically acceptable diluent and/or an adjuvant.

We also include that the composition, and/or antibody, and/or medicament of the invention may be suitable for parenteral administration including aqueous and/or non-aqueous sterile injection solutions which may contain antioxidants, and/or buffers, and/or bacteriostats, and/or solutes which render the formulation isotonic with the blood of the intended recipient; and/or aqueous and/or non-aqueous sterile suspensions which may include suspending agents and/or thickening agents. The composition, and/or antibody, and/or agent, and/or medicament of the invention may be presented in unit-dose or multi-dose containers, for example sealed ampoules and vials, and may be stored in a freeze-dried (i.e. lyophilised) condition requiring only the addition of the sterile liquid carrier, for example water for injections, immediately prior to use.

Extemporaneous injection solutions and suspensions may be prepared from sterile powders, and/or granules, and/or tablets of the kind previously described.

For parenteral administration to human patients, the daily dosage level of the antibody molecule that specifically binds FcγRIIb and/or the immune cell depleting or deactivating antibody molecule will usually be from 1 mg/kg bodyweight of the patient to 20 mg/kg, or in some cases even up to 100 mg/kg administered in single or divided doses. Lower doses may be used in special circumstances, for example in combination with prolonged administration. The physician in any event will determine the actual dosage which will be most suitable for any individual patient and it will vary with the age, weight and response of the particular patient. The above dosages are exemplary of the average case. There can, of course, be individual instances where higher or lower dosage ranges are merited and such are within the scope of this invention.

Typically, the composition and/or medicament of the invention will contain the antibody molecule that specifically binds FcγRIIb and/or the immune cell depleting or deactivating antibody at a concentration of between approximately 2 mg/ml and 150 mg/ml or between approximately 2 mg/mI and 200 mg/ml. In a preferred embodiment, the medicaments and/or compositions of the invention will contain the antibody molecule that specifically binds FcγRIIb and/or the immune cell depleting or deactivating antibody molecule at a concentration of 10 mg/ml.

Generally, in humans, oral or parenteral administration of the composition, and/or antibody, and/or agent, and/or medicament of the invention is the preferred route, being the most convenient. For veterinary use, the composition, and/or antibody, and/or agent and/or medicament of the invention are administered as a suitably acceptable formulation in accordance with normal veterinary practice and the veterinary surgeon will determine the dosing regimen and route of administration which will be most appropriate for a particular animal. Thus, the present invention provides a pharmaceutical formulation comprising an amount of an antibody and/or agent of the invention effective to treat various conditions (as described above and further below). Preferably, the composition, and/or antibody, and/or agent, and/or medicament is adapted for delivery by a route selected from the group comprising: intravenous (IV); subcutaneous (SC), intramuscular (IM), or intratumoural.

In some embodiments, either the first antibody molecule or the second antibody or both may be administered through the use of plasmids or viruses. Such plasmids then comprise nucleotide sequences encoding either the first antibody molecule or the second antibody or both. In some embodiments, nucleotide sequences encoding parts of or the full sequences of either the first antibody molecule or the second antibody or both integrated in a cell or viral genome or in a viriome in a virus; such a cell or virus then act as a delivery vehicle for either the first antibody molecule or the second antibody or both (or a delivery vehicle for a nucleotide sequence encoding either the first antibody molecule or the second antibody or both). For example, in some embodiments, such a virus may be in the form of a therapeutic oncolytic virus comprising nucleotide sequences encoding at least one of the antibody molecules described herein. In some embodiments, such an oncolytic virus comprises nucleotide sequences encoding a full-length human IgG antibody. Oncolytic viruses are known to those skilled in the arts of medicine and virology.

The present invention also includes composition, and/or antibody, and/or agent, and/or medicament comprising pharmaceutically acceptable acid or base addition salts of the polypeptide binding moieties of the present invention. The acids which are used to prepare the pharmaceutically acceptable acid addition salts of the aforementioned base compounds useful in this invention are those which form non-toxic acid addition salts, i.e. salts containing pharmacologically acceptable anions, such as the hydrochloride, hydrobromide, hydroiodide, nitrate, sulphate, bisulphate, phosphate, acid phosphate, acetate, lactate, citrate, acid citrate, tartrate, bitartrate, succinate, maleate, fumarate, gluconate, saccharate, benzoate, methanesulphonate, ethanesulphonate, benzenesulphonate, p-toluenesulphonate and pamoate [i.e. 1,1'-methylene-bis-(2-hydroxy-3 naphthoate)] salts, among others. Pharmaceutically acceptable base addition salts may also be used to produce pharmaceutically acceptable salt forms of the agents according to the present invention. The chemical bases that may be used as reagents to prepare pharmaceutically acceptable base salts of the present agents that are acidic in nature are those that form non-toxic base salts with such compounds. Such non-toxic base salts include, but are not limited to those derived from such pharmacologically acceptable cations such as alkali metal cations (e.g. potassium and sodium) and alkaline earth metal cations (e.g. calcium and magnesium), ammonium or water-soluble amine addition salts such as N-methylglucamine-(meglumine), and the lower alkanolammonium and other base salts of pharmaceutically acceptable organic amines, among others. The agents and/or polypeptide binding moieties of the invention may be lyophilised for storage and reconstituted in a suitable carrier prior to use. Any suitable lyophilisation method (e.g. spray drying, cake drying) and/or reconstitution techniques can be employed. It will be appreciated by those skilled in the art that lyophilisation and reconstitution can lead to varying degrees of antibody activity loss (e.g. with conventional immunoglobulins, IgM antibodies tend to have greater activity loss than IgG antibodies) and that use levels may have to be adjusted upward to compensate. In one embodiment, the lyophilised (freeze dried) polypeptide binding moiety loses no more than about 20%, or no more than about 25%, or no more than about 30%, or no more than about 35%, or no more than about 40%, or no more than about 45%, or no more than about 50% of its activity (prior to lyophilisation) when re-hydrated.

The combination of an antibody molecule that specifically binds FcγRIIb and an immune cell depleting or deactivating antibody molecule can be used use in the treatment of cancer.

"Patient" as the term is used herein refers to an animal, including human, that has been diagnosed as having an FcγRIIb negative cancer or as having a cancer that is considered as likely to be FcγRIIb negative cancer and/or that exhibits symptoms of such a cancer.

We include that the patient could be mammalian or non-mammalian. Preferably, the patient is a human or is a mammalian, such as a horse, or a cow, or a sheep, or a pig, or a camel, or a dog, or a cat. Most preferably, the mammalian patient is a human.

By "exhibit", we include that the subject displays a cancer symptom and/or a cancer diagnostic marker, and/or the cancer symptom and/or a cancer diagnostic marker can be measured, and/or assessed, and/or quantified.

It would be readily apparent to the person skilled in medicine what the cancer symptoms and cancer diagnostic markers would be and how to measure and/or assess and/or quantify whether there is a reduction or increase in the severity of the cancer symptoms, or a reduction or increase in the cancer diagnostic markers; as well as how those cancer symptoms and/or cancer diagnostic markers could be used to form a prognosis for the cancer.

Cancer treatments are often administered as a course of treatment, which is to say that the therapeutic agent is administered over a period of time. The length of time of the course of treatment will depend on a number of factors, which could include the type of therapeutic agent being administered, the type of cancer being treated, the severity of the cancer being treated, and the age and health of the patient, amongst others reasons.

By "during the treatment", we include that the patient is currently receiving a course of treatment, and/or receiving a therapeutic agent, and/or receiving a course of a therapeutic agent.

In some embodiments the FcγRIIb negative cancer to be treated in accordance with the present invention is a solid cancer.

In some embodiments, the cancer is selected from the group consisting of carcinomas, sarcomas, and lymphomas.

In some embodiments, the cancer is a carcinoma selected from the group consisting of adenocarcinoma, squamous cell carcinoma, adenosquamous carcinoma, anaplastic or undifferentiated carcinoma, large cell carcinoma and small cell carcinoma.

In some embodiments, the cancer is a sarcoma selected from the group consisting of osteosarcoma, chondrosarcoma, liposarcoma, and leiomyosarcoma. FcγRIIb negative cancer is selected from the group consisting of melanoma, breast cancer, ovarian cancer, prostate cancer, metastatic hormone-refractory prostate cancer, colonrectal cancer, lung cancer, small cell lung carcinoma (NSCLC), small cell lung cancer (SCLC), non-small cell lung cancer, urothelial carcinoma, bladder cancer, kidney cancer, mesothelioma, Merkel cell carcinoma, and head and neck cancer.

Each one of the above described cancers is well-known, and the symptoms and cancer diagnostic markers are well described, as are the therapeutic agents used to treat those cancers. Accordingly, the symptoms, cancer diagnostic markers, and therapeutic agents used to treat the above mentioned cancer types would be known to those skilled in medicine.

Clinical definitions of the diagnosis, prognosis and progression of a large number of cancers rely on certain classifications known as staging. Those staging systems act to collate a number of different cancer diagnostic markers and cancer symptoms to provide a summary of the diagnosis, and/or prognosis, and/or progression of the cancer. It would be known to the person skilled in oncology how to assess the diagnosis, and/or prognosis, and/or progression of the cancer using a staging system, and which cancer diagnostic markers and cancer symptoms should be used to do so.

By "cancer staging", we include the Rai staging, which includes stage 0, stage I, stage II, stage III and stage IV, and/or the Binet staging, which includes stage A, stage B and stage C, and/or the Ann Arbour staging, which includes stage I, stage II, stage III and stage IV.

It is known that cancer can cause abnormalities in the morphology of cells. These abnormalities often reproducibly occur in certain cancers, which means that examining these changes in morphology (otherwise known as histological examination) can be used in the diagnosis or prognosis of cancer. Techniques for visualizing samples to examine the morphology of cells, and preparing samples for visualization, are well known in the art; for example, light microscopy or confocal microscopy.

By "histological examination", we include the presence of small, mature lymphocyte, and/or the presence of small, mature lymphocytes with a narrow border of cytoplasm, the presence of small, mature lymphocytes with a dense nucleus lacking discernible nucleoli, and/or the presence of small, mature lymphocytes with a narrow border of cytoplasm, and with a dense nucleus lacking discernible nucleoli, and/or the presence of atypical cells, and/or cleaved cells, and/or prolymphocytes.

It is well known that cancer is a result of mutations in the DNA of the cell, which can lead to the cell avoiding cell death or uncontrollably proliferating. Therefore, examining these mutations (also known as cytogenetic examination) can be a useful tool for assessing the diagnosis and/or prognosis of a cancer. An example of this is the deletion of the chromosomal location 13q14.1 which is characteristic of chronic lymphocytic leukaemia. Techniques for examining mutations in cells are well known in the art; for example, fluorescence in situ hybridization (FISH).

By "cytogenetic examination", we include the examination of the DNA in a cell, and, in particular the chromosomes. Cytogenetic examination can be used to identify changes in DNA which may be associated with the presence of a refractory cancer and/or relapsed cancer. Such may include: deletions in the long arm of chromosome 13, and/or the deletion of chromosomal location 13q14.1, and/or trisomy of chromosome 12, and/or deletions in the long arm of chromosome 12, and/or deletions in the long arm of chromosome 11, and/or the deletion of 11q, and/or deletions in the long arm of chromosome 6, and/or the deletion of 6q, and/or deletions in the short arm of chromosome 17, and/or the deletion of 17p, and/or the t(11:14) translocation, and/or the (q13:q32) translocation, and/or antigen gene receptor rearrangements, and/or BCL2 rearrangements, and/or BCL6 rearrangements, and/or t(14:18) translocations, and/or t(11:14) translocations, and/or (q13:q32) translocations, and/or (3:v) translocations, and/or (8:14) translocations, and/or (8:v) translocations, and/or t(11:14) and (q13:q32) translocations.

It is known that patients with cancer exhibit certain physical symptoms, which are often as a result of the burden of the cancer on the body. Those symptoms often reoccur in the same cancer, and so can be characteristic of the diagnosis, and/or prognosis, and/or progression of the disease. A person skilled in medicine would understand which physical symptoms are associated with which cancers, and how assessing those physical systems can correlate to the diagnosis, and/or prognosis, and/or progression of the disease. By "physical symptoms", we include hepatomegaly, and/or splenomegaly.

BRIEF DESCRIPTION OF THE DRAWINGS

In the examples below, reference is made to the following figures:

FIG. 1A shows the use of only an anti-CTLA-4 antibody. The anti-CTLA-4 antibody binds to, and thus activates, both activating and inhibitory Fcγ receptors, thus resulting in a weak activation, and thus a reduced effect compared to what the situation had been had the anti-CTLA-4 antibody bound to only activating Fcγ receptors.

FIG. 1B shows that the combination of an anti-CTLA-4 antibody and WT (wild type) FcγRIIb antibody leads to reduced activation. In this case, the FcγRIIb antibody both blocks activating Fcγ receptors and activates inhibitory Fcγ receptors, which is the opposite of the effect desired in accordance with the present invention.

FIG. 1C shows that the combination of an anti-CTLA-4 antibody and an aglycosylated FcγRIIb antibody according to the invention leads to maximum activation. There is no blocking of activating Fcγ receptors and there is no activation of inhibitory Fcγ receptors, leading to maximal deletion of the target. Here aglycoslyated FcγRIIb antibody could be one lacing the Fc domain or with otherwise reduced binding to the FcRs.

(FIG. 2A-B) CFSE$^+$ hCD20$^{+/-}$x mFcγRII$^{-/-}$ (target) and mFcγRII$^{-/-}$ (non-target) splenocytes were injected into hFcγRIIB$^{+/-}$x mFcγRII$^{-/-}$ recipient mice. Mice received WT or N297Q FcγRIIB mAb (6G11) (2×20 mg/kg) followed by Rit (0.2-2 mg/kg) and the ratio of blood (A) and splenic (B) CFSE$^+$ CD19$^+$ cells determined, as before. Data combined from at least 2 independent experiments. (FIG. 2C) CFSE$^+$ hCD20$^{+/-}$x mFcγRII$^{-/-}$ (target) and mFcγRII$^{-/-}$ (non-target) splenocytes were injected into hFcγRIIB$^{+/-}$x mFcγRII$^{-/-}$ recipient mice. Mice received WT or N297Q FcγRIIB mAb (6G11) (20 mg/kg) followed by Rit (2 mg/kg) and the expression of activatory mFcγRs was quantified on splenic F4/80+effector cells using indicated mAb. (FIG. 2D-E) Ability of WT and N297Q (NQ) hFcγRIIB specific mAb (6G11; 10 μg/ml for 15 min) to elicit hFcγRIIB ITIM phosphorylation (pFcγRIIB) on (FIG. 2D) mouse BMDMs, and (FIG. 2E) isolated primary peripheral blood monocytes following high density culture, respectively. α-Tubulin, GAPDH and hFcγRIIB were used as loading controls, as indicated; representative blots shown.

FIG. 4A) 100 μg AT130-2 NA given by intraperitoneal injection (i.p.) to female Balb/c mice. 100 μg PC61 given i.p 6 hours later. Tregs (FoxP3+) in blood, spleen and lymph nodes determined by FACs 4 days later. Mice were culled and single cell suspensions obtained from the spleen, LN and blood which were stained with antibodies against CD4, CD8 and B220 prior to intracellular FoxP3 staining before being analysed on a FACs canto. The white cell count for each tissue was determined. Tregs were defined as being CD8-CD4+ FoxP3+ and the number of Tregs calculated using the white cell count. FIG. 4B) as above but with C57BU6 mice.

FIG. 6A) represents the treatment schedule. Group 1: No Ab; Group 2: anti-mCD32 (AT130-2 NA; 100 μg); Group 3: anti-CTLA-4 (9H10; 200 μg); Group 4: combination (PC61) 6 hours after AT130-2. Tumours were allowed to establish and were treated at 100 mm$^2$. An extra dose was given on day 12. FIG. 6B) shows growth of the individual tumours. FIG. 6C) represents the mean tumour area +/− SD or SEM. FIG. 6E) Composite from 2 separate experiments (n=10/group) displaying survival and demonstrated that the combination of 9H10 and AT130-2NA (NA combo) is significantly more potent at extending survival than the 9H10 alone (p=0.0179).

FIG. 8B shows the survival curves for the mice.

EXAMPLES

Figure 1:
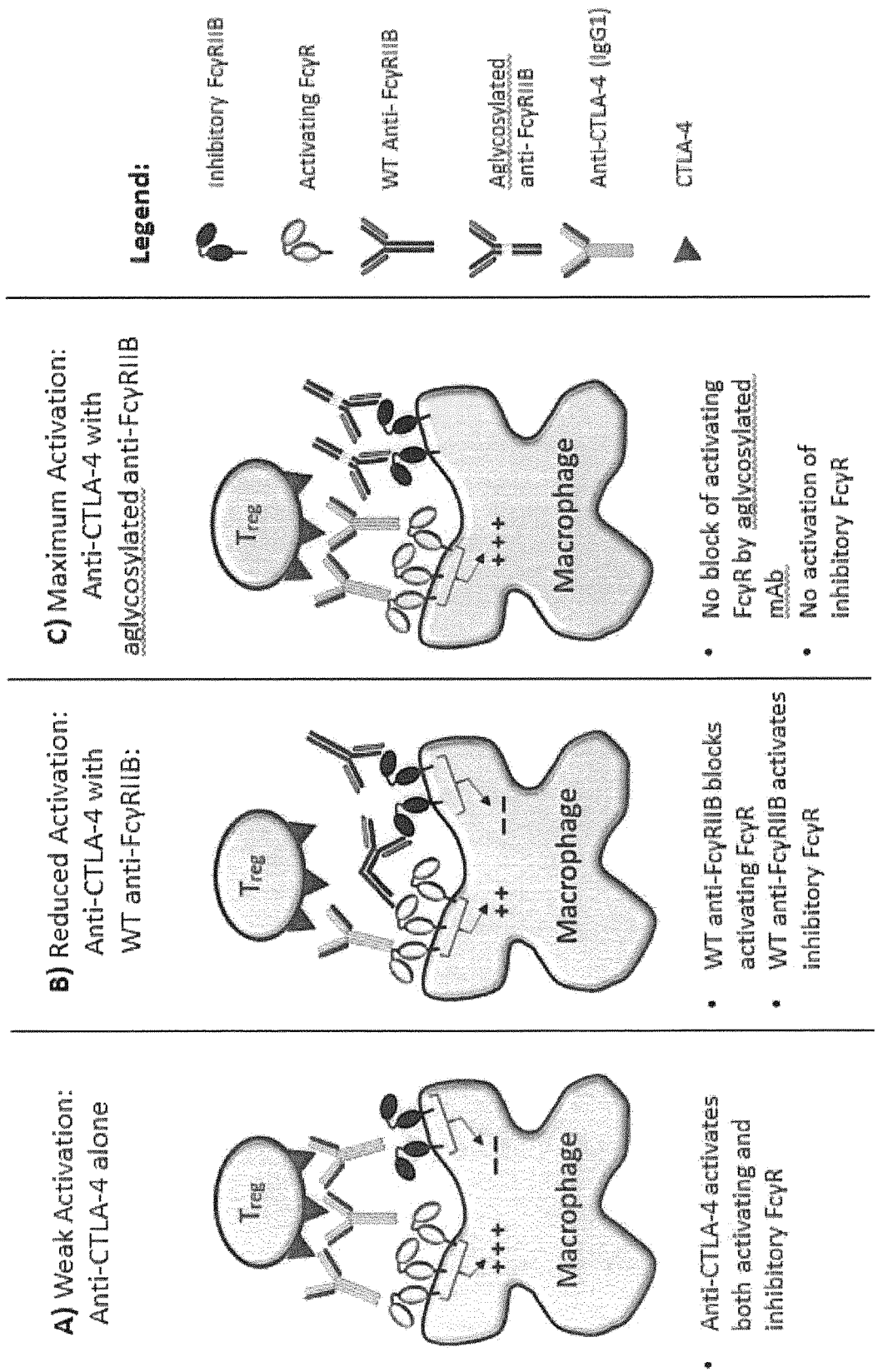
FIG. 1 illustrates a potential mechanism explaining why the invention works. The immune cell depleting or deactivating antibody molecule, in this case an anti-CTLA-4 antibody, binds to a receptor present on the immune cell that supresses anti-cancer immunity, in this case a Treg. The Fc region of the anti-CTLA-4 antibody binds to an activating Fcγ receptor, which in this case in present on the surface of a macrophage. In addition, an antibody molecule that specifically binds FcγRIIb, binds to FcγRIIb present on the surface of the macrophage. Since this specific antibody has an Fc region with reduced binding to activating Fcγ receptors, it does not bind to any of the activating Fcγ receptors present on the macrophage, which instead are free for binding to the Fc region of the anti-CTLA-4 antibody.

Specific, non-limiting examples which embody certain aspects of the invention will now be described. To allow for examining the effect of blockade of FcγRIIB in complex in vivo systems, two sets of surrogate antibodies has to be used. The murine equivalent of 6G11 is called AT130-2. To Fc mute a human antibody (hence to render the binding to FcγR's severely impaired or negligable), we have replaced the amino acid position 297 from a N to a Q. To Fc mute a murine antibody, the same position is replaced from and N to an Q. Hence, in a murine system we will refer to AT-130, while this patent application concenrns the human counterpart 6G11 In short, the human 6G11 corresponds to the murine surrogate AT1302-2, while the 6G11-N297A corresponds to the AT130-3-N297A.

A different way to Fc mute an antibody (and well known to those skilled in the art) would be to take away the Fc part and form a Fab or Fab2 fragment, Experimental Procedures Animals hCD20 Tg (transgenic), hFcγRIIB$^{+/-}$ and mFcγRIIB$^{-/-}$ mice have been described previously (Beers et al., Blood 2008 Nov. 15; 112(10):4170-7; Roghanian et al, Cancer Cell 27, 473-488, Apr. 13, 2015) with genotypes confirmed by PCR and/or flow cytometry. Mice were bred and maintained in local facilities in accordance with the UK Home Office guidelines or local Swedish Ethical committee.

Cell Culture

Cell culture was performed in supplemented RPMI (RPMI 1640 containing 2 mM glutamine, 1 mM pyruvate, 100 IU/ml penicillin and streptomycin and 10% FCS [Myoclone]) (GIBCO BRL, Paisley, Scotland). Mouse splenic B cells were purified by negative selection using MACS B cell isolation kits (Miltenyi Biotec, UK) and cultured in the same media. Cell-lines were obtained from ECACC and maintained in antibiotic-free supplemented RPMI medium.

Generation of Human Monocyte-Derived Macrophages (MDM) and Mouse Bone Marrow Derived Macrophages (BMDM)

Human MDMs were differentiated from peripheral blood obtained either from the National Blood Service, Southampton General Hospital (Southampton, UK) or from the blood centers in the hospital of Halmstad or Skåne University Hospital (Sweden). Briefly adherent CD14$^+$ monocytes were cultured in supplemented RPMI containing 25-100 ng/mL endotoxin-low recombinant human macrophage-colony stimulating factor (M-CSF; R&D Systems, US or produced in-house), as previously described (Roghanian et al., Cell Immunol. 2010; 265(2):120-6.). Half of the medium was replaced with fresh M-CSF every 2 days until harvest. On day 7-10 of culture, MDMs were harvested following a short incubation with cold PBS.

Mouse BMDMs were generated from cells isolated from the bone marrow of the femur and tibia of mice, as previously reported (Williams et al., J Immunol. 2013 Oct. 15; 191(8):4130-40.). Briefly, bone marrow cells were cultured in supplemented RPMI containing 20% L929 cell—conditioned medium (containing M-CSF). Cells were cultured at 37° C., 5% CO2 for 10-12 days prior to use. Macrophage differentiation was routinely confirmed by morphological examination and/or flow cytometry for CD11b and F4/80 expression.

Antibodies and Reagents mAb were typically produced from the culture supernatant of hybridoma or stably transfected CHO-k1 cells (obtained from ECACC). F(ab')$_2$ fragments were produced as described previously (Glennie et al., 1987). The hFcγRII mAb AT10 was previously described (Greenman et al., 1991). Anti-CTLA4 (9H10; Bio X Cell, US), anti-IL2R (PC-61.5.3; Bio X Cell/in-house), anti-PDL-1 (10F.9G2 Bio X Cell, US). The hFcγRII mAb 6G11 hIgG1 and N297Q were produced by Biolnvent (see Roghanian et al, Cancer Cell 27, 473-488, April 13, 2015). The mFcγRII mAb AT130-2 mIgG1, mIgG2a and mIgG1 N297A were produced in-house. AT130-5 (Williams et al, Eur J Immunol. 2012; 42(8):2109-20, and Tutt et al J Immunol 2015, 195 (11) 5503-5516) is a murine anti-mouse FcγRII antibody similar to the human antibody clone 6G11.). Antibodies against hFcγRIIB (clone EP888Y; Abcam, UK), phosphorylated hFcγRIIB (clone EP926Y; Ori-gene, US), GAPDH (Abcam, UK) and a-tubulin (Cell Signaling, US) were used for immunoblotting. For PBMC immunophenotyping, FcγRIIB mAb labelled with PE using zenon labelling kit (Molecular Probes) was used in conjunction with anti-CD3-FITC, anti-CD19-PerCP-Cy5.5 and anti-CD56-APC (antibodies obtained from Biolegend).

Flow Cytometry

Fluorescently conjugated mAb were purchased from BD Biosciences, eBiosciences, Biolegend, AbD Serotec (all UK) or made in-house. Flow cytometry was performed as described previously (Tutt et al., 1998) with samples assessed on a FACScan, FACSCalibur or FACSCanto II with data analyzed with CellQuest Pro, FACSDiva (all BD Biosciences, UK) or FCS Express (De Novo Software, CA, US).

Western Blotting

As described previously (Roghanian et al, Cancer Cell 27, 473-488, Apr. 13, 2015).

Immunotherapy In Vivo

Adoptive transfer. As detailed previously (Beers et al., Blood. 2010 Jun. 24; 115(25):5191-201).

B cell depletion: Mice were given hCD20 or hFcγRIIB mAb alone or in combination i.v. and leukocytes assessed as before (Beers et al., Blood. 2010 Jun 24; 115(25):5191-201).
CT26

CT26 cells were maintained in complete DMEM and harvested using Trypsin-EDTA. Cells were washed, resuspended in PBS and the concentration was adjusted to $5 \times 10^6$ cells/ml using a haemocytometer. 100 µl cell suspension ($5 \times 10^5$ cells) was injected s.c. into BALB/c mice (bred in-house from original stocks obtained from Charles River, UK). Tumours were allowed to establish and tumour size measured 3 times per week prior to randomisation and treatment. Tumours were considered terminal when tumour length x width exceeded 400 mm².

MC38

MC38 cells were maintained in complete DMEM and harvested using Trypsin-EDTA. Cells were washed, resuspended in PBS and the concentration was adjusted to $5 \times 10^6$ cells/ml using a haemocytometer. 100 µl cell suspension ($5 \times 10^5$ cells) was injected s.c. into C56/BI6 mice (obtained from Taconic, Denmark). Tumours were allowed to establish and tumour size measured prior to randomisation and treatment. Treatment started at a tumor volume of 50-100 mm² and thereafter tumors were measured 2 times per week. Treatments were performed 4 times with 3-4 days in between treatments and the dose of anti-PD-L1 was set at 10 mg/kg and both AT130-2 variants at 20 mg/kg. Tumours were considered terminal when tumour volume exceeded 2000 mm²

Statistical Analysis

To compare experimental groups Wilcoxon, paired or unpaired t test analyses were performed; Kaplan Meier curves were produced and analyzed by Log rank test. For in vivo adaptive transfer assays containing >2 groups, one- or two-way ANOVA were used.

For differences in OR and CR, Chi-square tests were used. Statistical analysis was performed using GraphPadPrism (v5 or 6). Stars denote significance as follows: *p 0.05, p≤0.01, *p ≤0.001 and ****p≤0.0001, unless otherwise stated.

Results

Efficacy of B Cell Depletion Depends on FcγRIIB mAb Format

Figure 2:
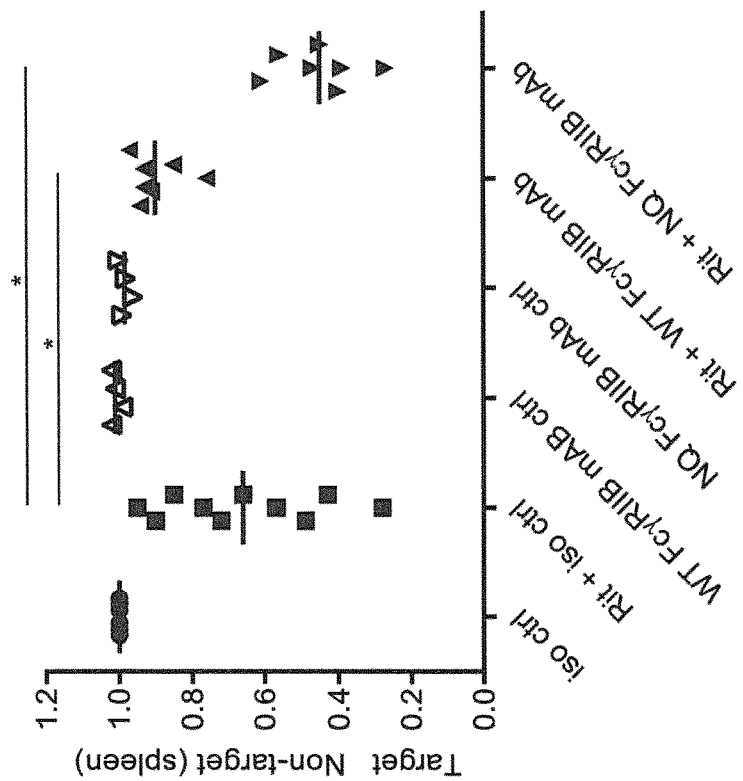
FIG. 2 illustrates that FcγRIIB antibodies with impaired Fc binding to activating Fc receptors, but not wild type antibodies with retained binding to activating Fc receptors boost B cell depletion by CD20 mAb.
Figure 2:
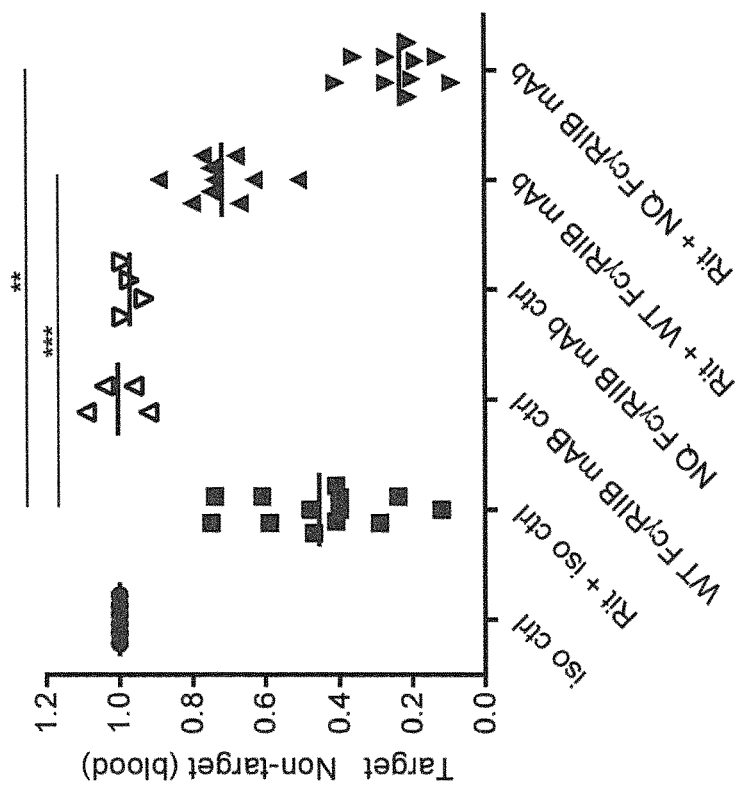

FcγRIIB is expressed both on target B cells and effector monocytes/macrophages, making it difficult to interpret where FcγRIIB mAb contribute their effects to more profound target cell deletion. In order to dissect this further we took advantage of our various hFcγRIIB Tg and KO mouse strains to provide systems in which either target cell or effector or both could be targeted with FcγRIIB mAb. In assays where hCD20$^{+/-}$ targets lacking hFcγRIIB were adoptively transferred into hFcγRIIB$^{+/-}$ x mFcγRIIB$^{-/-}$ recipients, FcγR-null and WT FcγRIIB mAb treatment alone had no effect on B cell deletion as expected (FIG. 2A). FcγR-null FcγRIIB mAb potentiated depletion of both circulating (FIG. 2A) and tissue-resident (FIG. 2B) target cells when combined with rituximab, whereas WT FcγRIIB mAb impaired deletion. This demonstrates that using a normal FcγRIIB monoclonal antibody impairs target cell deletion through a second antibody, which was very unexpected to the inventors. When assessing FcγR expression on splenic F4/80$^+$ macrophages from treated mice, it was evident that that detection of mFcγRIV (FIG. 2C) was lower when WT but not FcγR-null FcγRIIB mAb had been used, which may partially explain the inhibitory effects of WT FcγRIIB mAb. This demonstrates that a normal IgG FcγRIIB monoclonal antibody makes the deletion worse because it blocks the activating FcγRIV.

This so-called scorpion effect (Hogarth review), occurs when a functional Fc domain from a cell surface binding mAb occupies the Fc binding cleft of an FcγR expressed on the same cell and hence is not observed with the FcγR-null FcγRIIB mAb. It has been described previously and accounts for the potential over-interpretation of the relative importance of individual FcγR when they are blocked with Fc-functional anti-FcγR mAb such the FcγRIV mAb 9E9 (Tipton et al, Blood 2015 125:1901-1909).

In addition to physical blockade, this scorpion effect also has the potential to deliver receptor cross-linking and activation of FcγR. As the ITIM-containing FcγRIIB is the only inhibitory FcγR on effector cells and its activation may contribute to inhibition of effector cell function (Dahal et al., Immunol Rev. 2015 November; 268(1):104-22), we assessed its activation following treatment with WT or FcγR-null FcγRIIB mAb. We previously showed that on B-cells (which express only FcγRIIB), treatment with the antagonist 6G11 WT or NQ mAb did not activate FcγRIIB (Roghanian et al, Cancer Cell 27, 473-488, Apr. 13, 2015). However, WT but not FcγR-null FcγRIIB mAb resulted in phosphorylation of FcγRIIB-ITIM in both treated human monocyte derived macrophages (MDMs) (FIG. 2D) and mouse hFcγRIIB$^{+/-}$x mFcγRIIB$^{-/-}$ BMDMs (FIG. 2E), providing evidence for this phenomenon in our system and indicating that effector activation may not be optimal when WT FcγRIIB mAb are used. This demonstrates that the normal FcγRIIB mAb activate the inhibitory signals in the immune effector cells. Taking this observation together with those above considering the optimal FcγRIIB mAb format for deleting the target cells, we next explored how optimal deletion might be achieved.

WT and FcγR-null hFcγRIIB mAb can be Combined for Optimal Target Cell Depletion

Figure 3:
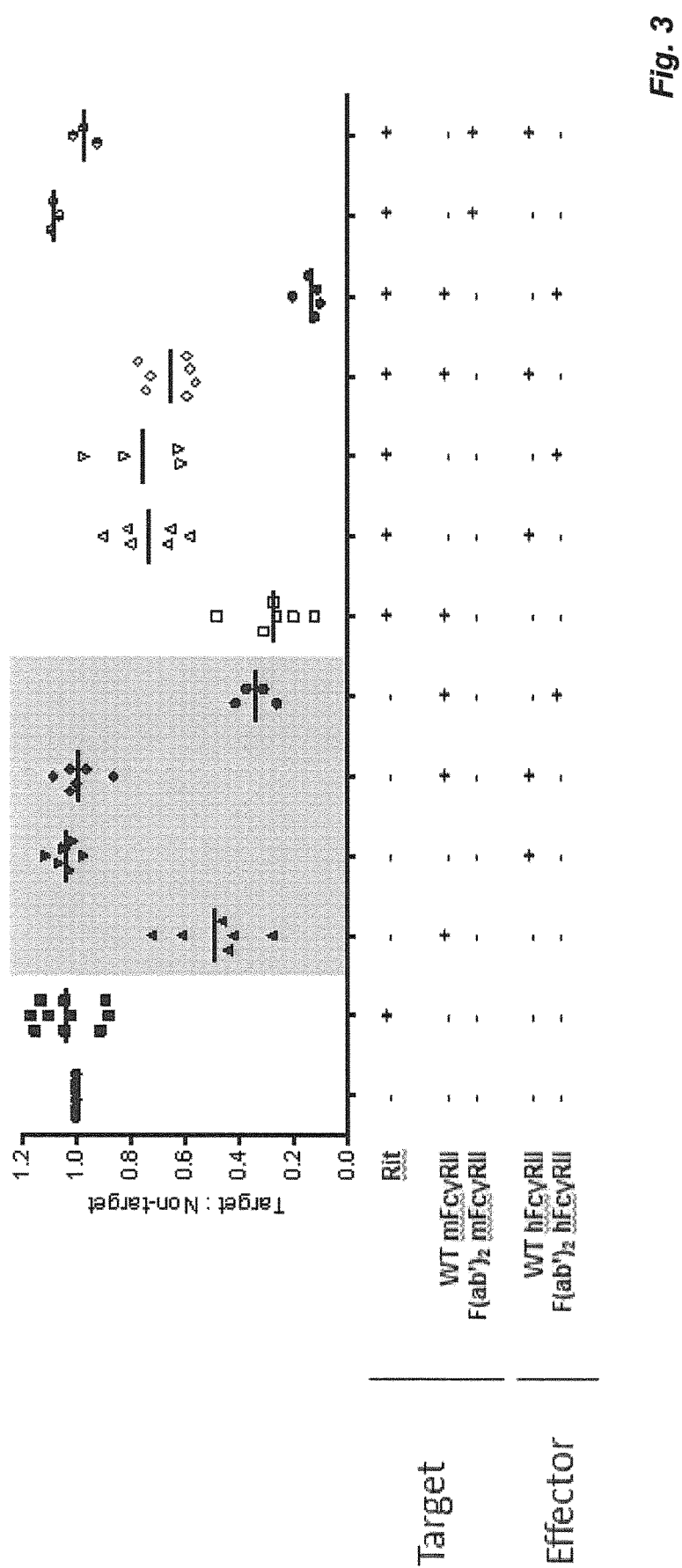
FIG. 3 illustrates that WT and FcγR-null FcγRIIB mAb can be combined for optimal depletion of target cells CFSE$^+$ hCD20$^{+/-}$ (target) and mFcγRII$^{-/-}$ (non-target) splenocytes were injected into hFcγRIIB$^{+/-}$ x mFcγRII$^{-/-}$ (Balb/c) recipient mice. Mice received WT (2×10–20 mg/kg) or F(ab')$_2$ (2×20 mg/kg) mFcγRII (AT130-5) or WT (2×20 mg/kg) or F(ab')$_2$ (2×40 mg/kg) hFcγRIIB mAb (AT10) followed by Rit (0.2-2 mg/kg), as indicated on the X axis, and the ratio of splenic CFSE$^+$ CD19$^+$ cells determined, as before. Data combined from 1-3 independent experiments. Each dot depicts a result from an individual mouse, with mean ratios indicated by the horizontal line. Data analysed using One-way ANOVA.

Next, we examined the efficacy of various hFcγRIIB and mFcγRII mAb forms in the presence or absence of rituximab in a system in which mFcγRIIB was only expressed on target B cells and hFcγRIIB was only expressed on effector cells. This system enabled concomitant analysis of targeting target- and effector-restricted FcγRIIB. Initially we examined the effect on mAb binding FcγRIIB only on the target. Treatment of mice with suboptimal doses of single agent rituximab resulted in minimal depletion of target B cells (FIG. 3). Treatment of mice with optimal doses of single agent WT mFcγRII mAb (targeting FcγRIIB present only on the targets), resulted in around 50% depletion of target cells. Co-administration of WT mFcγRII mAb with rituximab resulted in profound depletion (around 75% of resident splenic B cells); whereas addition of an Fc-null F(ab')$_2$ mFcγRII mAb had no effect either alone or in the presence of rituximab. This demonstrates that in order to delete an FcγRIIB expressing target in the absence of FcγRIIB on the effectors you would use a normal FcγRIIB mAb.

Subsequently we examined targeting of the FcγRIIB specifically on the effector cells; treatment of mice with WT or F(ab')$_2$ hFcγRIIB (targeting FcγRIIB only on the effectors) resulted in no deletion of the B cells as expected. However, a combination of rituximab and WT or F(ab')$_2$ hFcγRIIB resulted in increased target cell depletion compared to rituximab alone. Even more potent deletion was observed when WT mFcγRII mAb was used to target the B cell and F(ab')$_2$ hFcγRIIB used to target the effectors. In contrast, treatment with WT mFcγRIIB mAb, alongside WT hFcγRIIB mAb, abrogated depletion (FIG. 3). This demonstrates that a normal blocking FcγRIIB mAb impairs depletion of the target. The Fc modified Fab2 mAb was used to block the effectors.

Exploring these combinations further, when WT hFcγRIIB mAb was used to block effector cell hFcγRIIB, the depletion with a combination of rituximab and WT mFcγRII mAb was only around 30%. Far more profound depletions were seen when rituximab and WT mFcγRII mAb, both of which opsonize target B cells were combined with an Fc-null F(ab')₂ hFcγRIIB mAb, which blocks effector cell hFcγRIIB, resulting in around 90% depletion of target cells (FIG. 3).

Optimal Formats of FcgRIIB Blocking mAb Augment Treg Deletion

Figure 9:
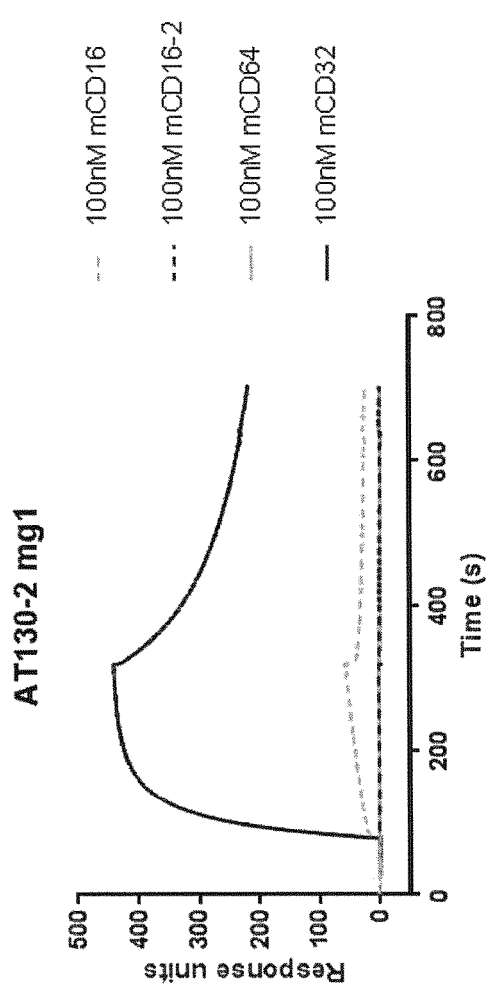
FIG. 9 shows wild-type (top) versus N297A (bottom) formats of the anti-mouse FcγRIIB mAb AT130-2 binding to FcγRs. It shows SPR analysis of AT130-2 in either format binding to the mouse FcγRs indicated (100 nM).
Figure 9:
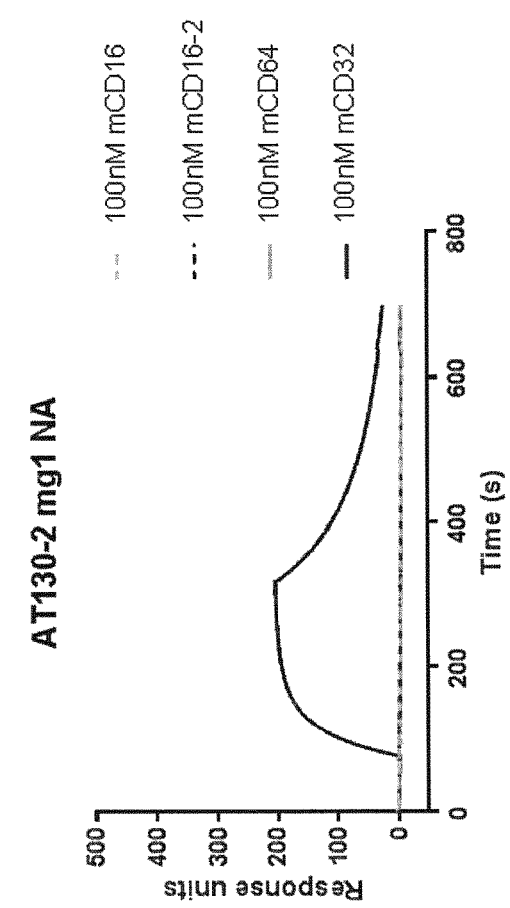
Figure 10:
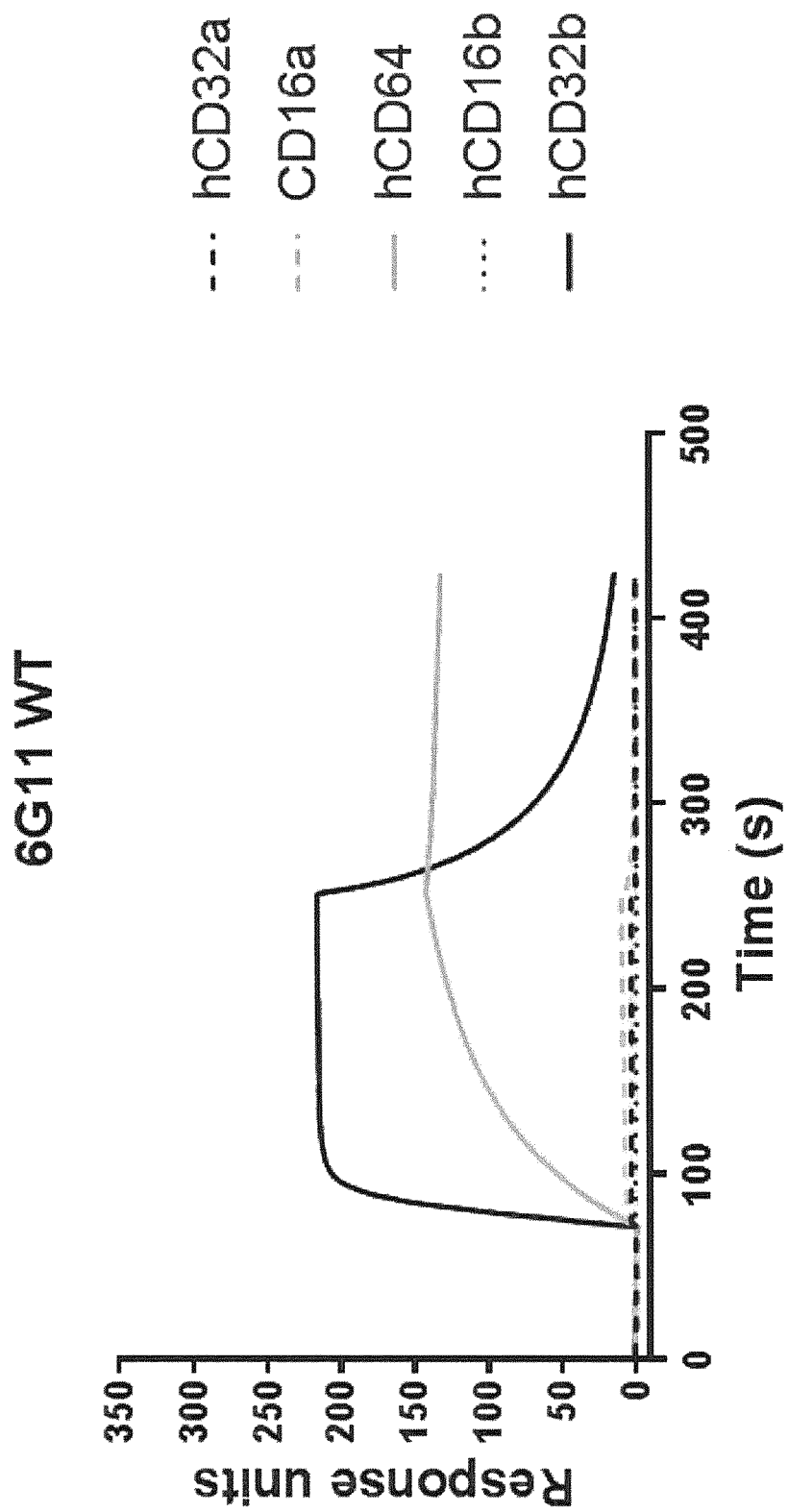
FIG. 10 shows WT 6G11 versus N297A 6G11 binding to Fc gamma receptors (mouse and human). It illustrates SPR analysis of native and N297A anti-huCD32b 6G11 hIgG1 binding to the low affinity human and mouse FcγRs indicated.
Figure 10:
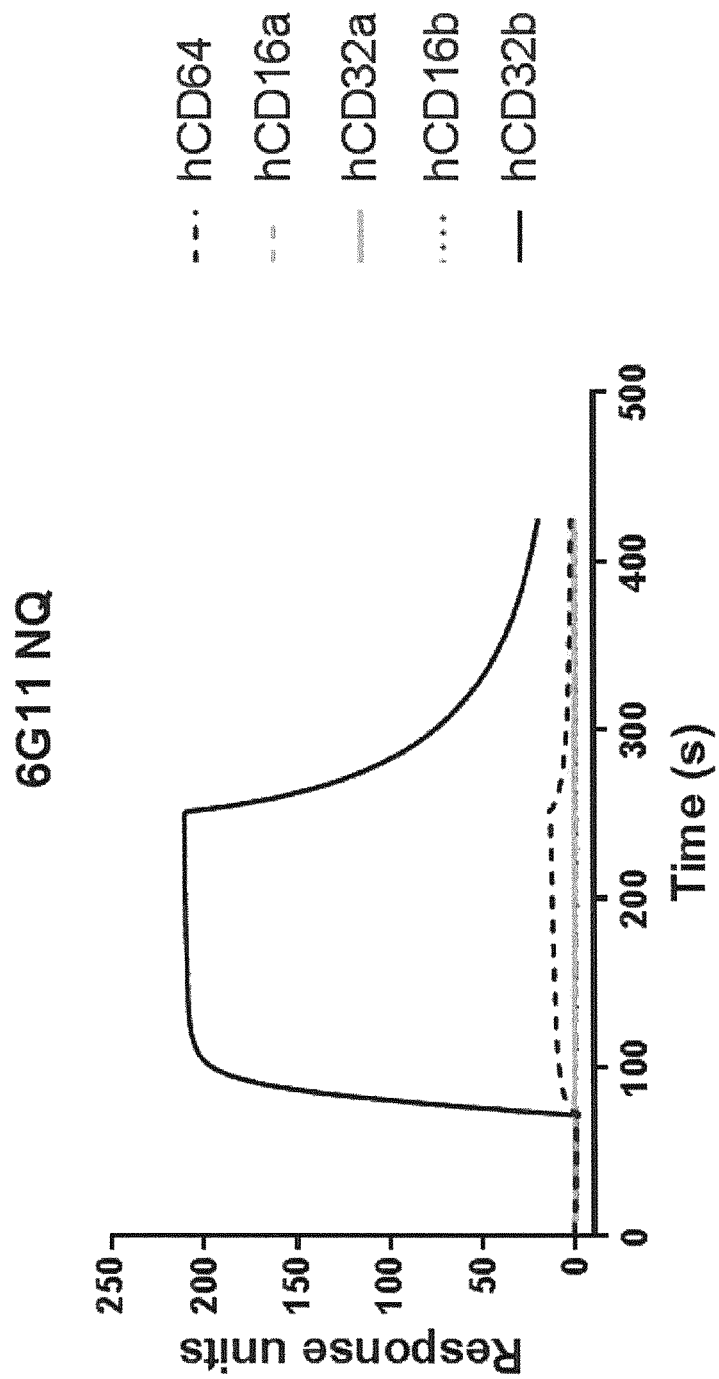
Figure 10:
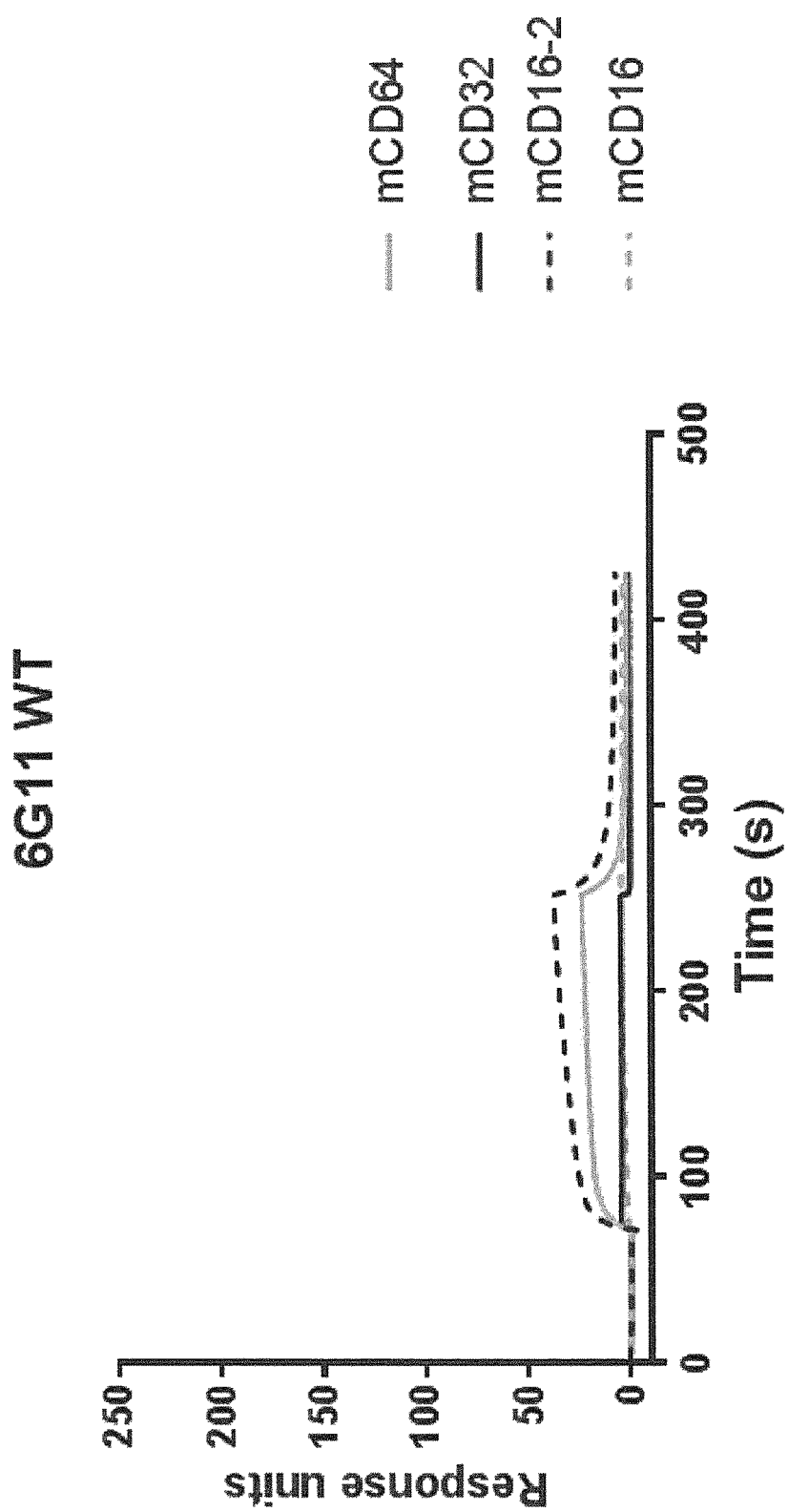
Figure 10:
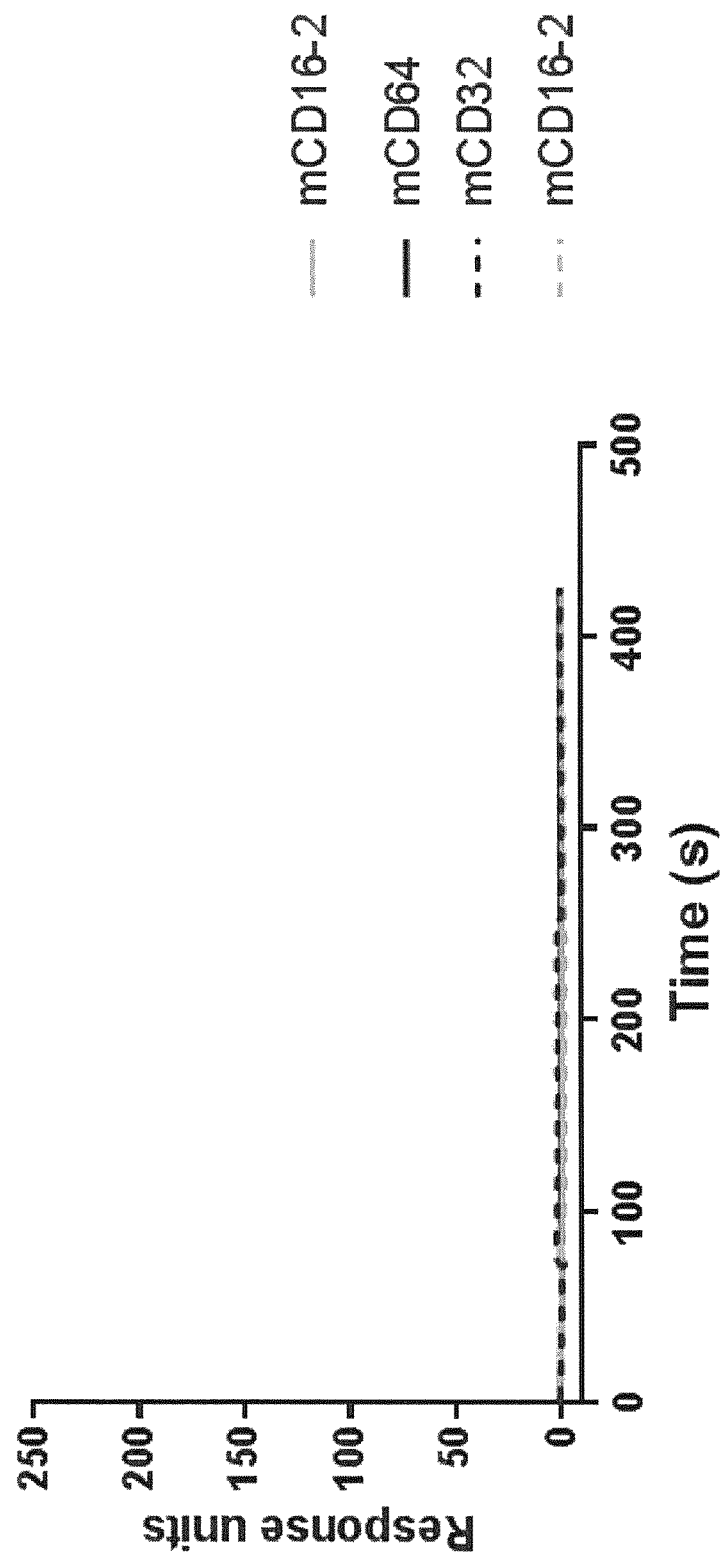
Figure 10:
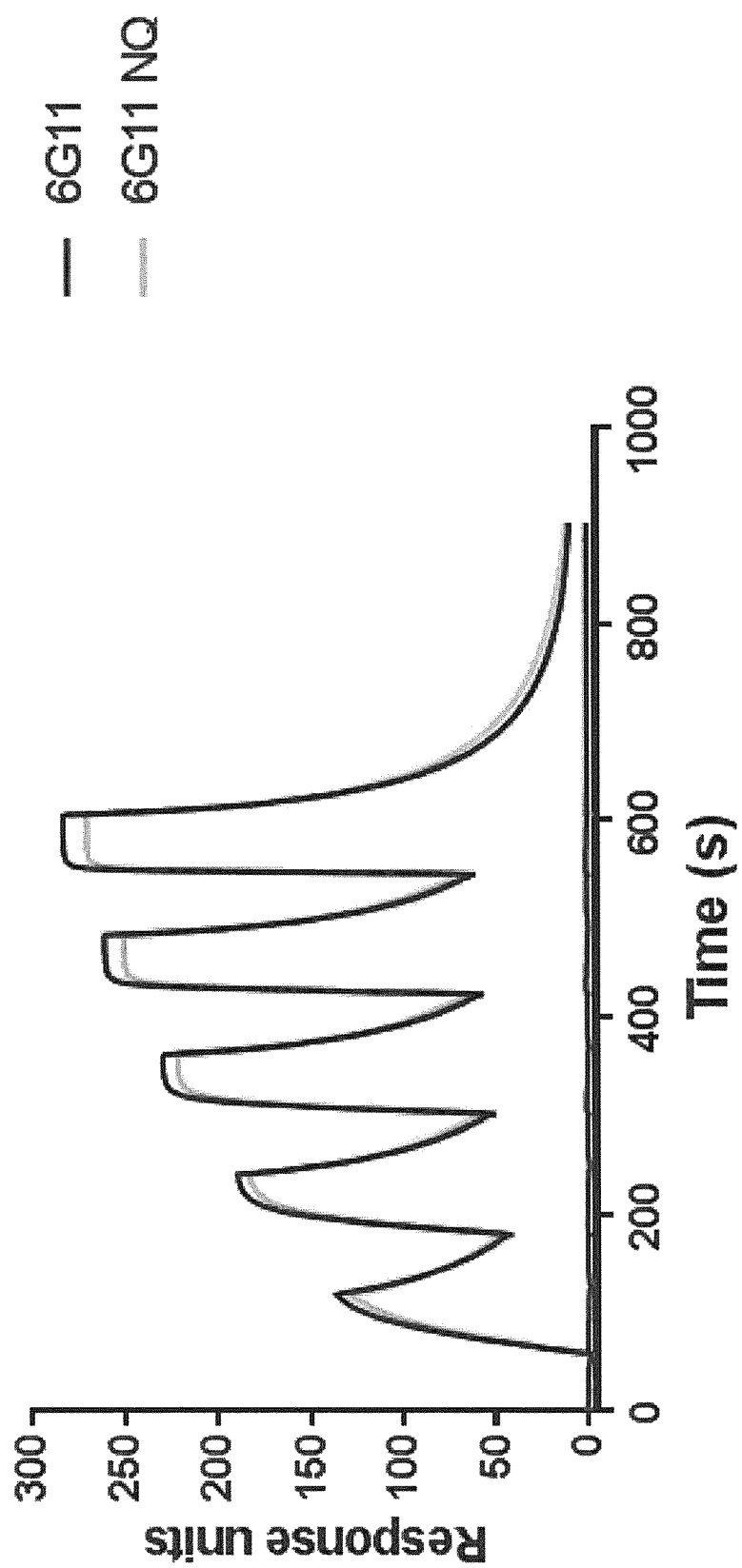
Figure 10:
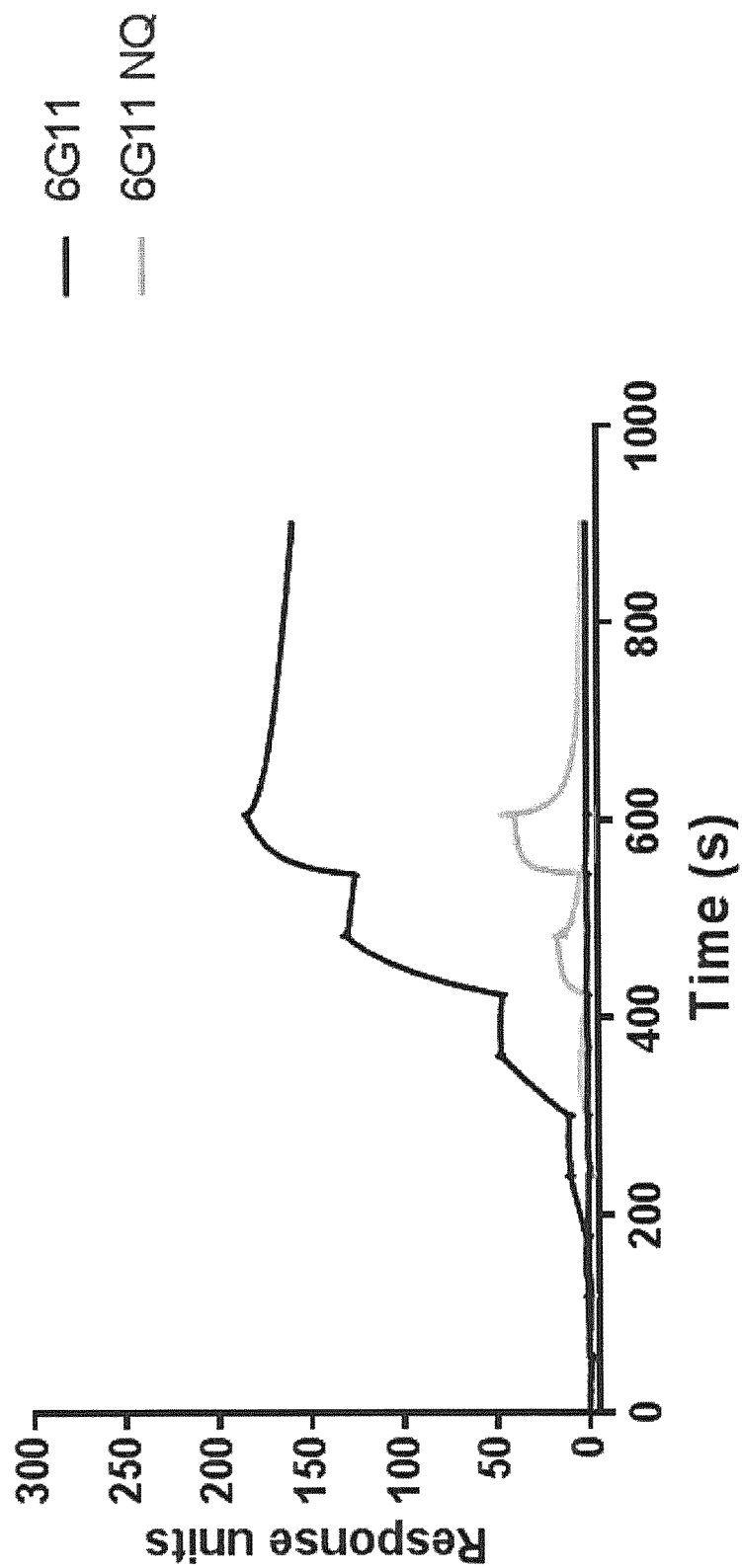
Figure 10:
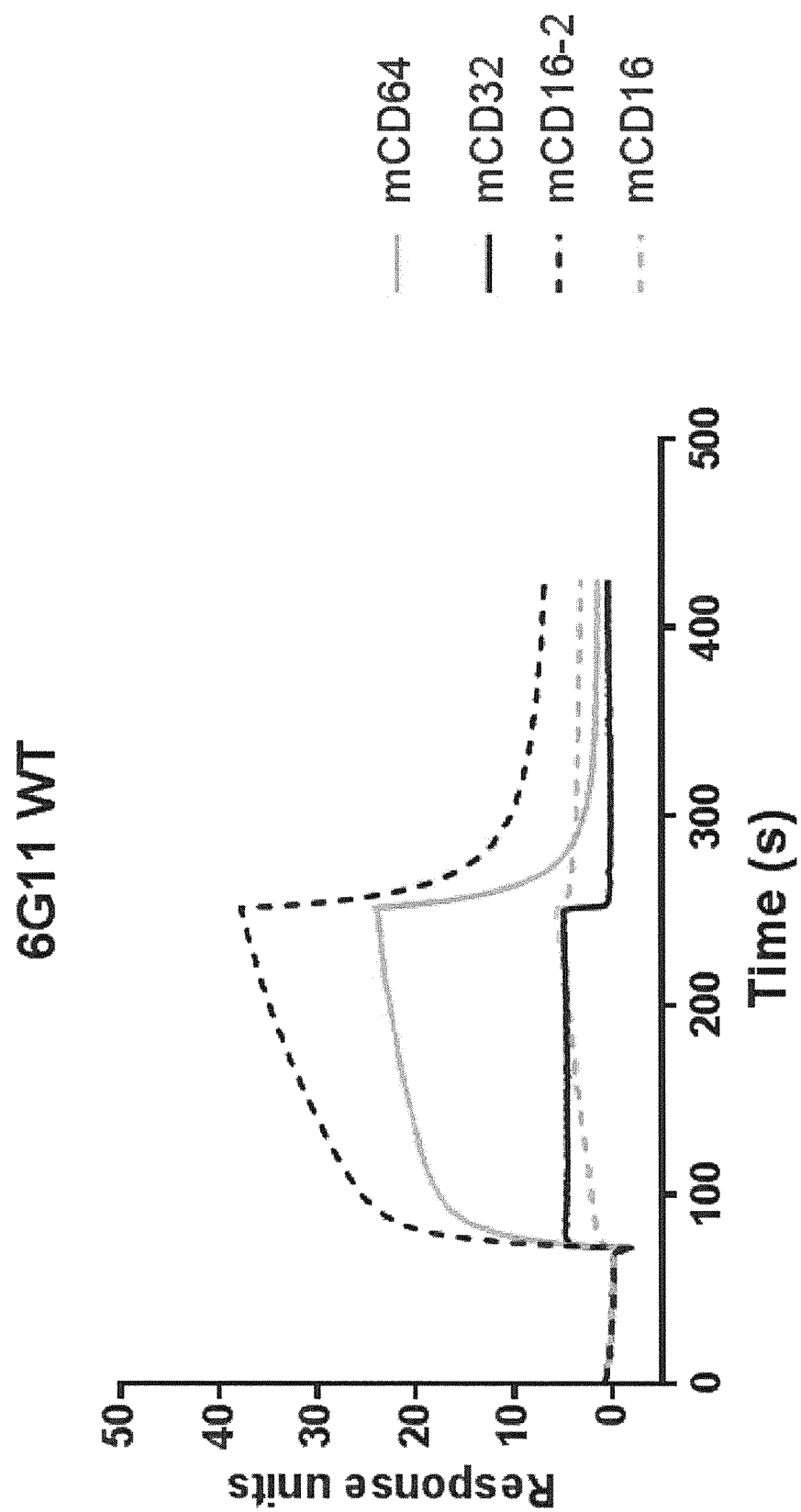
Figure 10H:
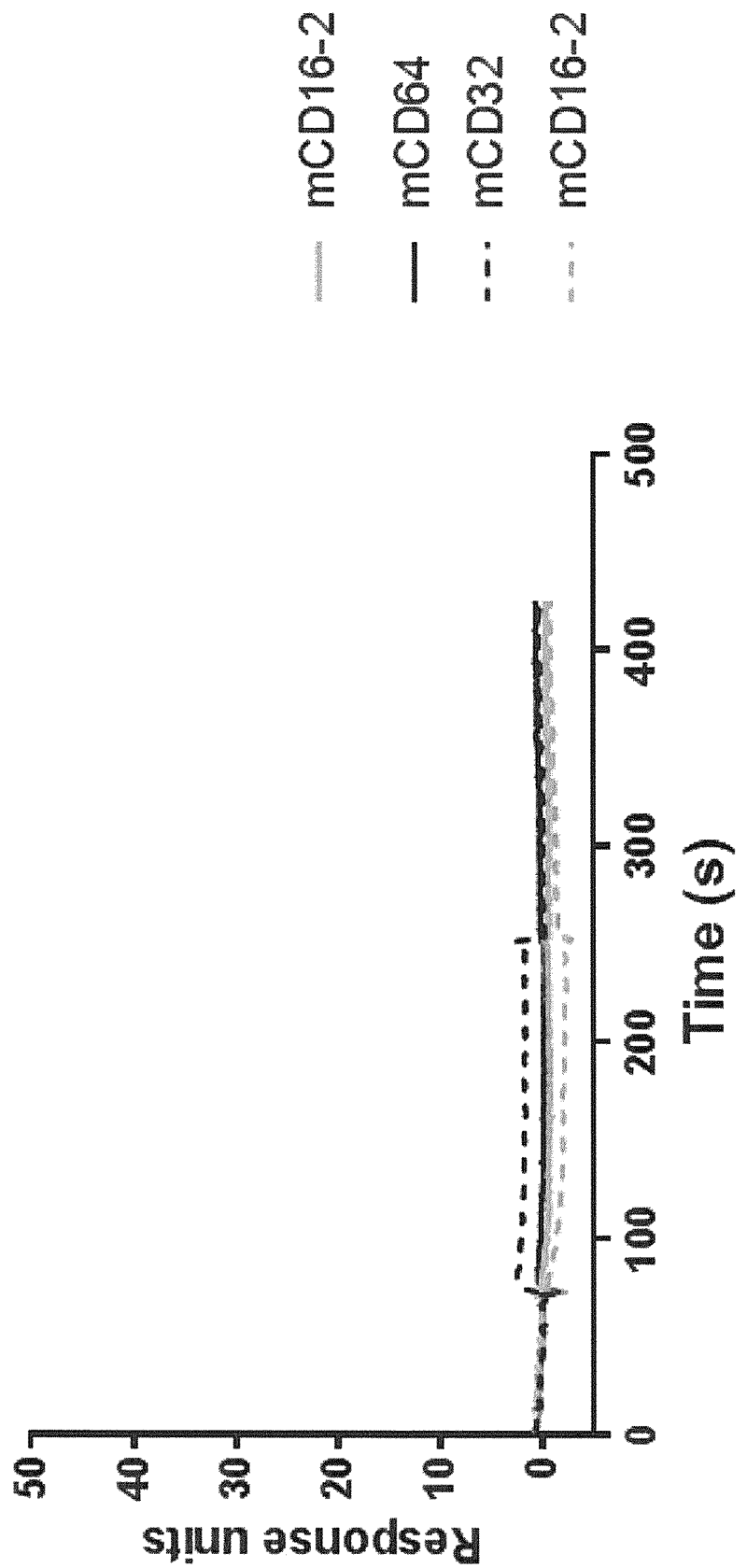
FIG. 10A and B show results for human FcγR (100 nM).
FIG. 10C and D show the results for mouse FcγR (100 nM).
FIG. 10E and E show the results for human FcγR (serial increasing additions)—FcγRIIb and hCD64.
FIG. 10G and H show the results for mouse FcγR (100 nM), i.e. the same as FIG. c and d but rescaled for clearer view.

We next assessed whether this capacity to augment deletion of targets by blocking FcgRIIB could be translated to other cellular targets, such as Treg. This is similar to the example above, but using IL2R to deplete the Tregs. To address this 100 μg of an Fc-inert anti-FcγRIIb mAb (AT130-2 mIgG1 NA, FIG. 9) was given i.p. to Balb/c mice.

Figure 4:
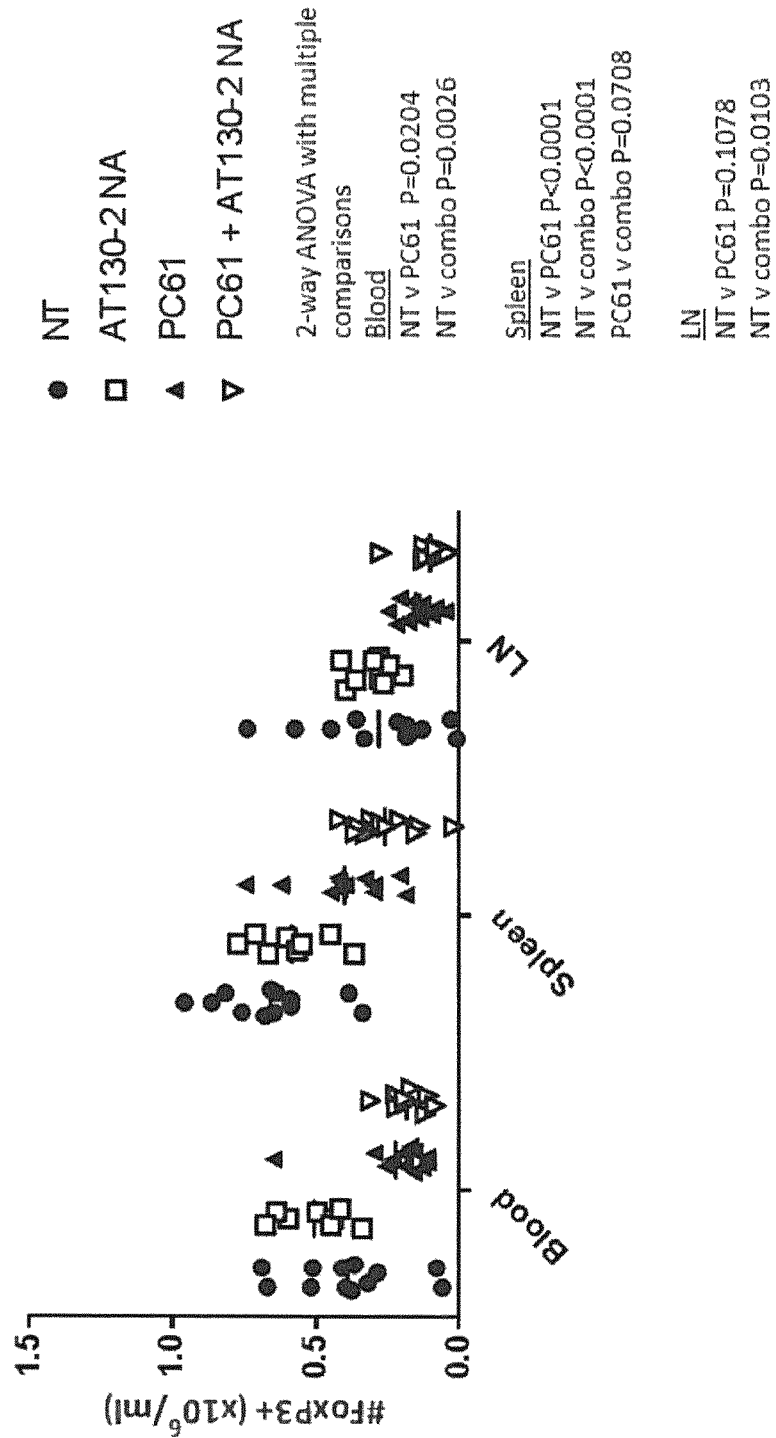
FIG. 4 shows assessment of Treg deletion with anti-IL2R mAb +/− FcγRIIB blockade with Fc-inert-NA mutant mAb.
Figure 4C:
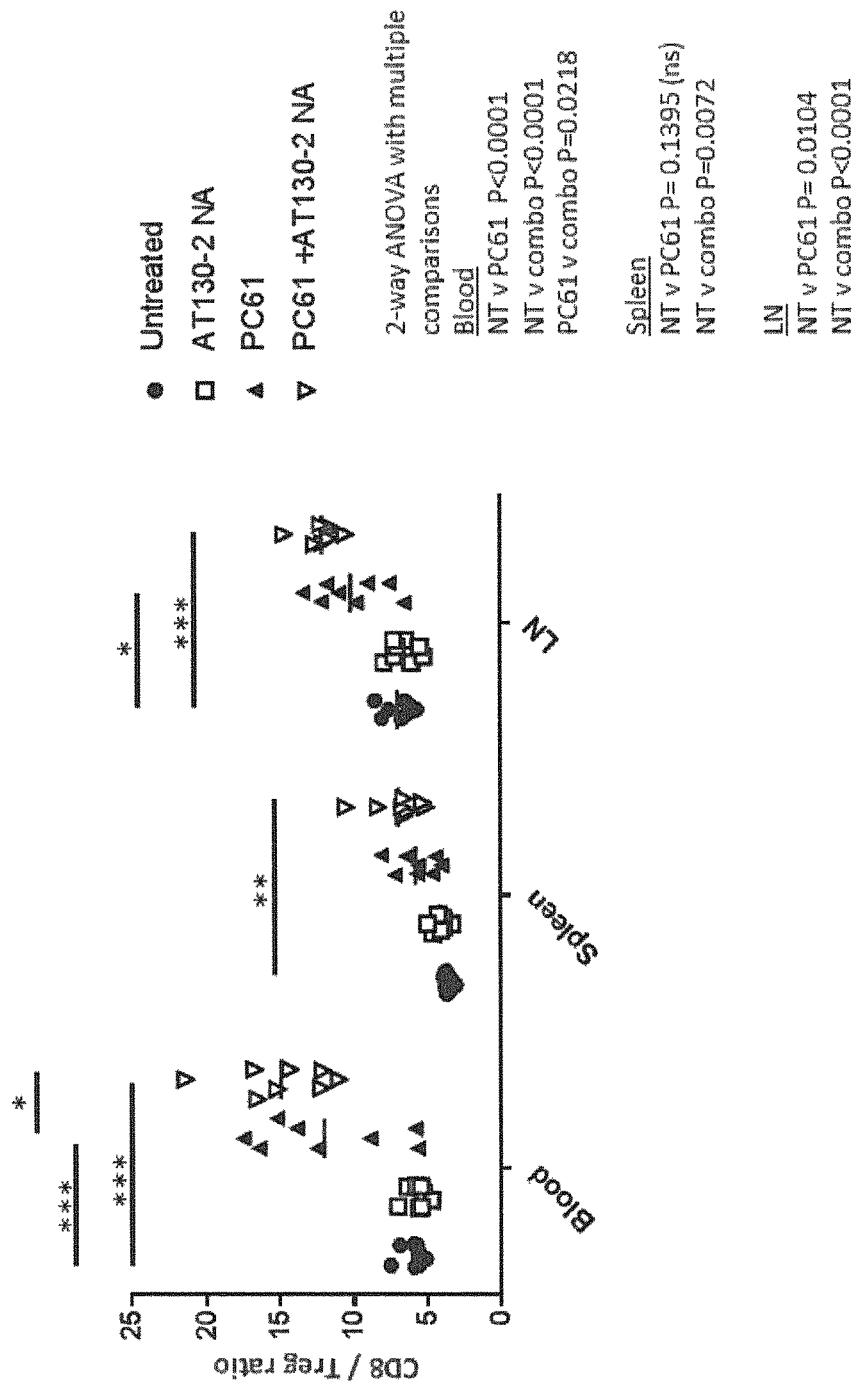
FIG. 4C) CD8/Treg ratio calculated from FIG. 4B).
Figure 5:
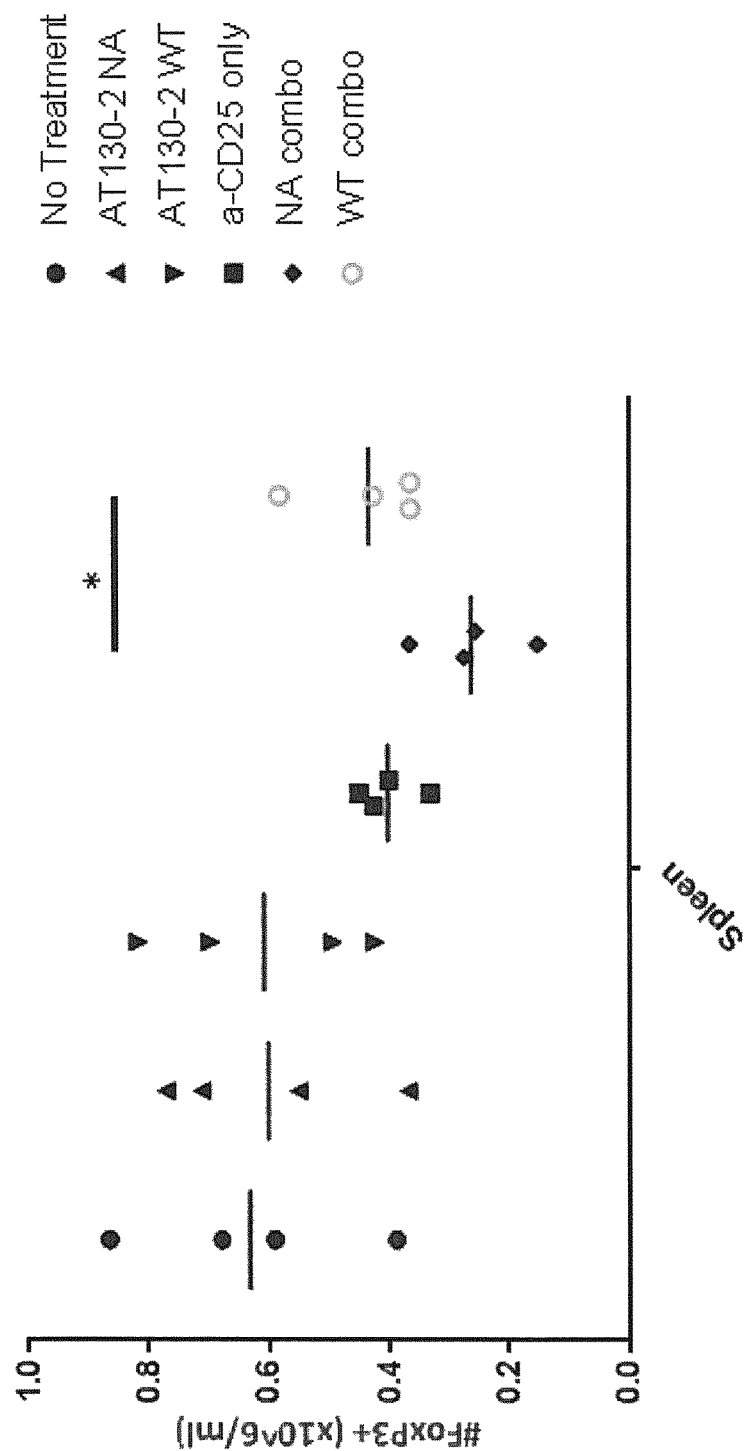
FIG. 5 shows assessment of Treg deletion with anti-IL2R mAb +/− FcγRIIB blockade with wild-type or NA mutant mAb. WT AT130-2 does not appear to give any improvement in deletion; whereas NA variant does. A) 100 μg AT130-2 NA or mIgG1 WT AT130-2 was given i.p. to female Balb/c mice. 100 μg PC61 given i.p 6 hours later. Tregs (FoxP3$^+$) in spleen determined by FACs 4 days later. Mice were culled and single cell suspensions obtained from the spleen which was stained with antibodies against CD4, CD8 and B220 prior to intracellular FoxP3 staining before being analysed on a FACs canto. The white cell count for each tissue was determined. Tregs were defined as being CD8-CD4+ FoxP3+ and the number of Tregs calculated using the white cell count. There was a significantly lower number of Tregs in the spleen of mice 4 days receiving the N297A antibody in combination with PC61 compared to a wild-type mIgG1 AT130-2 (unpaired T-test, P=0.044)

Subsequently 100 μg of the anti-IL2R (PC61) was given i.p 6 hours later in order to delete FoxP3+ Treg cells. These were then assessed in blood, spleen and lymph nodes by FACs after 4 days. AT130-2 NA was shown to improve Treg deletion, particularly in the spleen (FIG. 4A). To address the reproducibility of this affect we repeated this experiment in C57BL/6 mice. Again, AT130-2 NA was seen to improve Treg deletion in B6 mice, particularly in the spleen and LN (FIG. 4B) leading to higher CD8:Treg ratios in the blood, spleen and LN (FIG. 4C). The ratio in blood was significantly higher with the NA combination than PC61 alone (PC61 v combo P=0.0218). To confirm our earlier findings we next assessed the ability of the WT AT130-2 versus the Fc-inert AT130-2 NA mutant to improve the IL2R mAb-mediated deletion of the Tregs. WT AT130-2 did not give any improvement in deletion; whereas NA variant did (* unpaired T-test, P=0.044) (FIG. 5). Thus, this demonstrates that a normal FcγRIIb blocking mAb does not improve depletion.

mAb-Mediated FcgRIIB Blockade Augments CTLA-4 Immunotherapy

Figure 6:
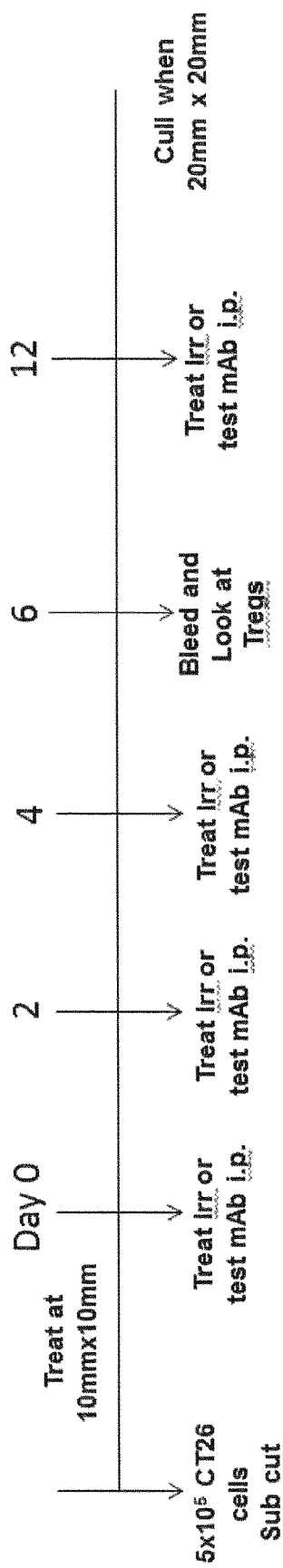
FIG. 6 illustrates combination therapy with anti-CTLA-4 and FcγRIIB blockade. $5×10^5$ CT26 cells were injected S.C into female BALB/c mice. Mice were randomised into treatment groups when tumour width x length was approximately 100 mm$^2$. Treatment was performed on days 0, 2, 4 and 11. 9H10 (hamster anti-mouse CTLA4) only mice received 200 μg antibody I.P in 200 μl PBS on each day. On day 0 combination mice received 100 μg AT130-2 N297A (anti-mouse CD32) in 200 μl PBS I.P, 6 hours later they received 200 μg 9H10 I.P in 200 μl PBS. On days 2, 4 and 11 combination mice received both antibodies (200 μg 9H10 and 100 μg AT130-2 NA) in a single 200 μl I.P injection. The width and length of tumours was measured and mice were culled when tumour length×width exceeded 400 mm$^2$.
Figure 6:
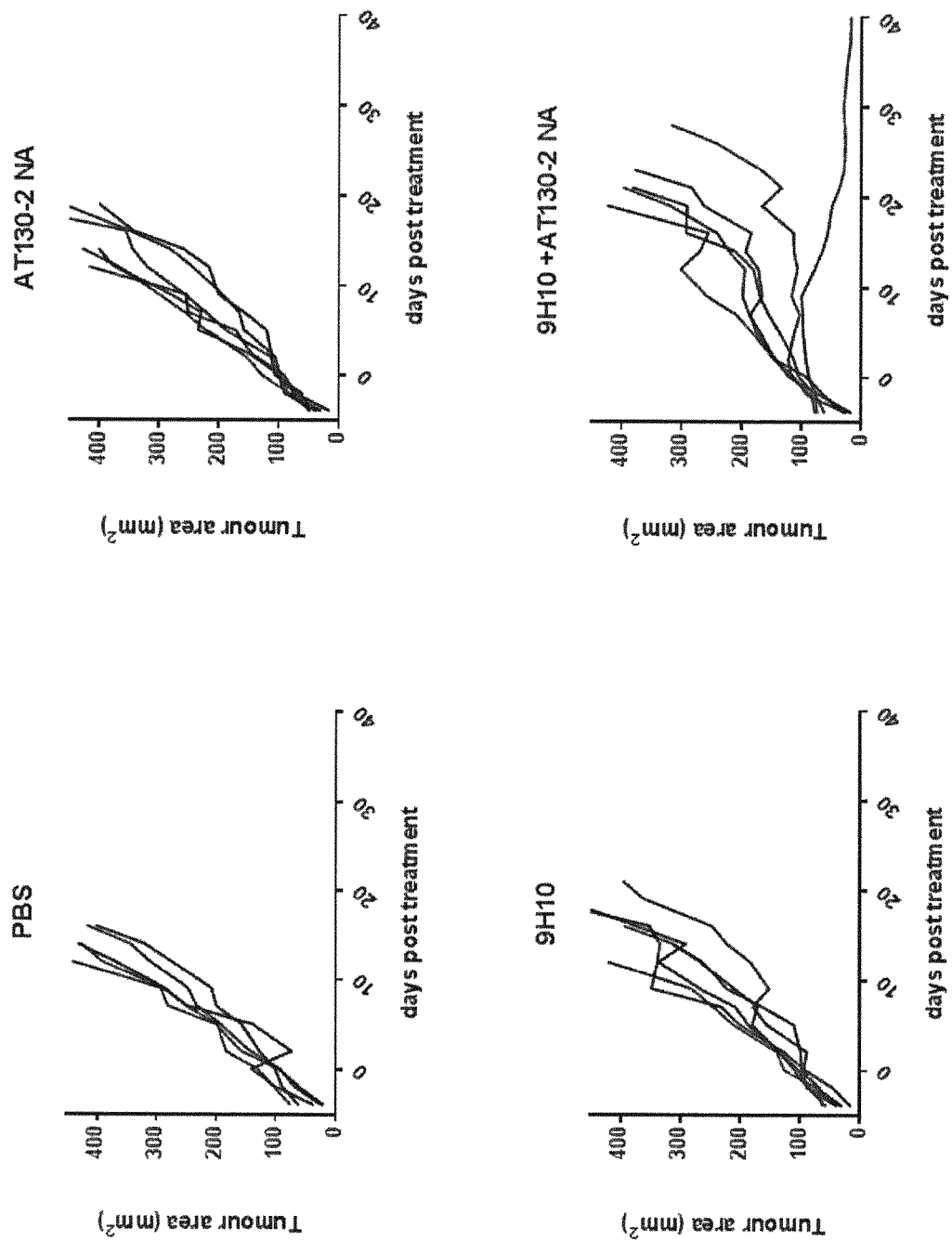
Figure 6:
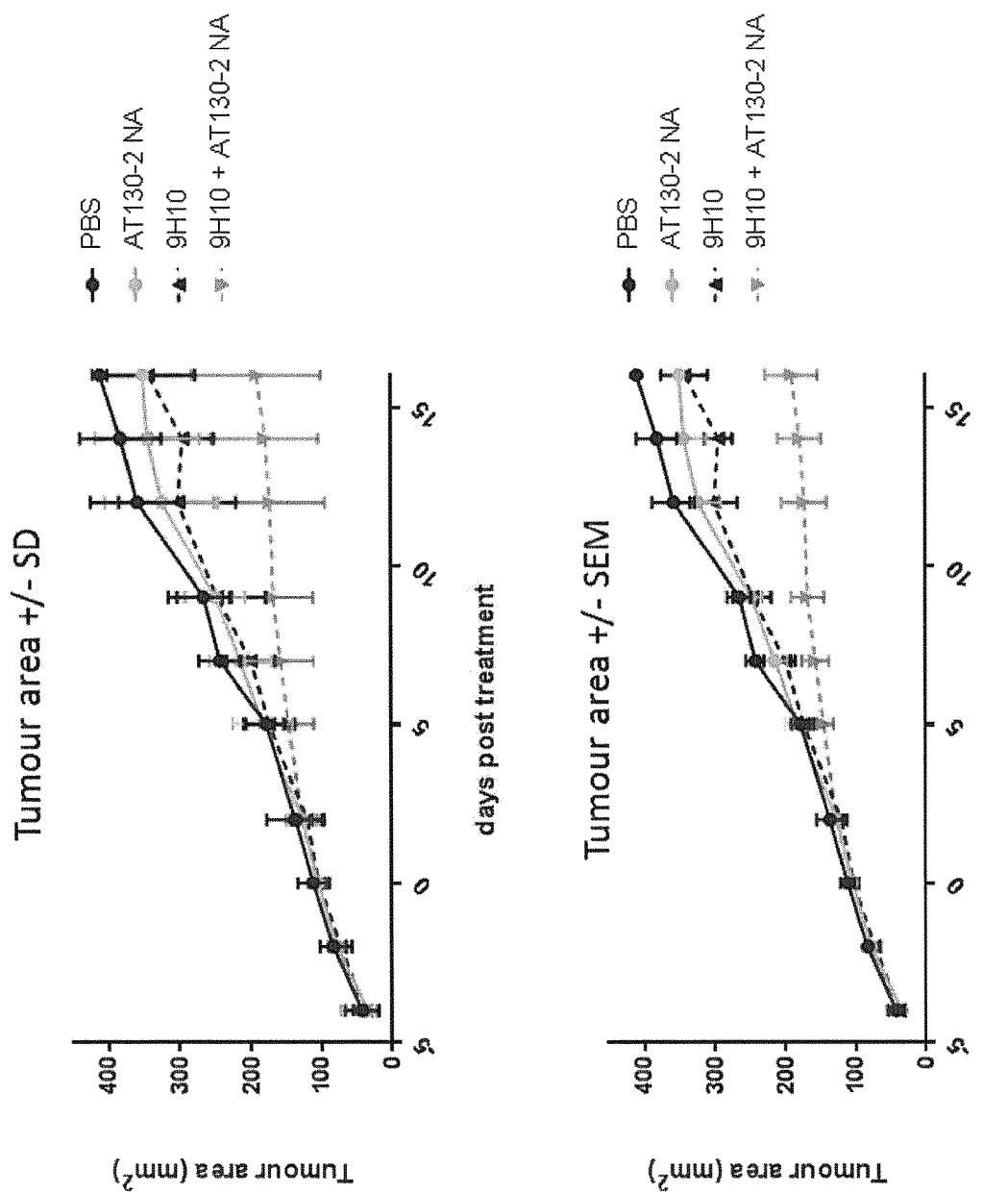
Figure 6D:
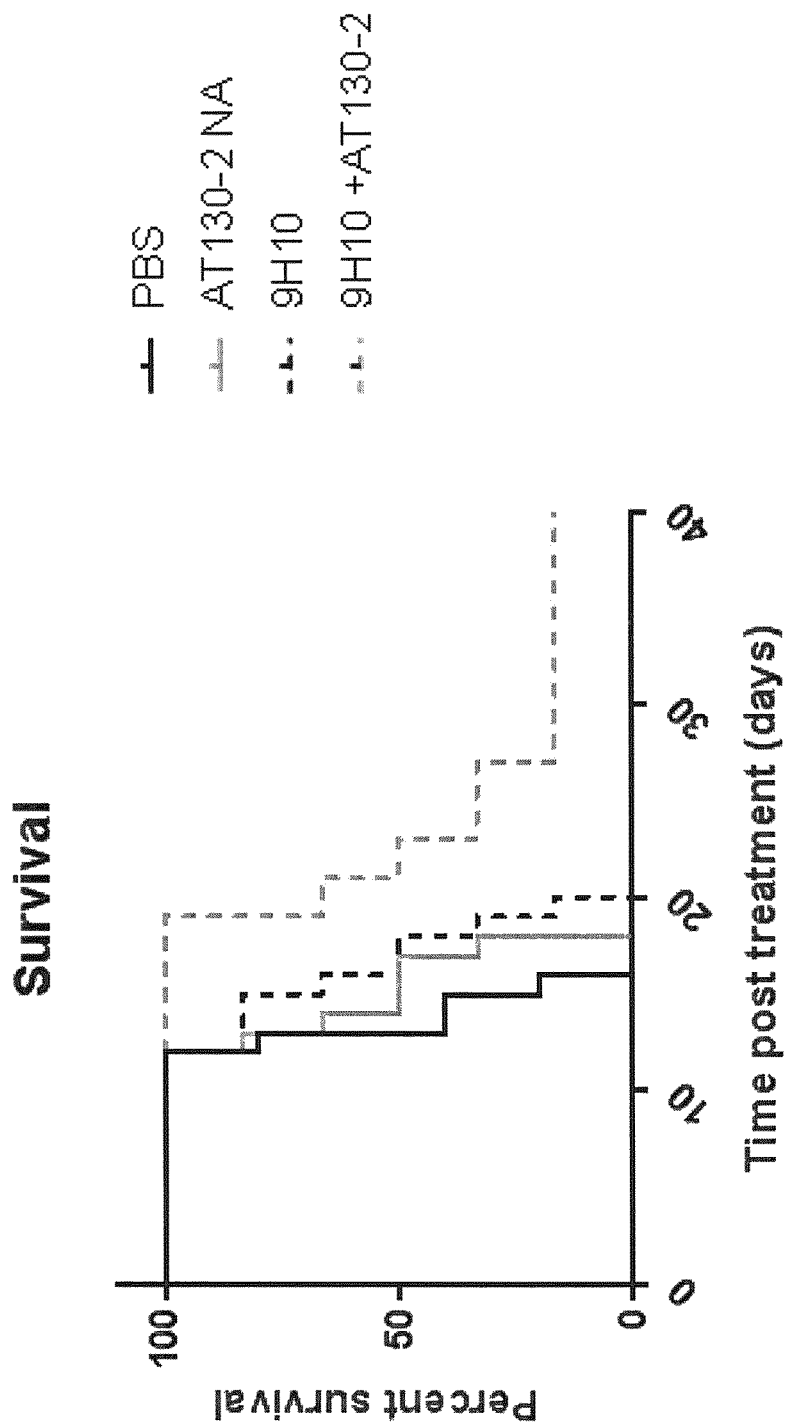
FIG. 6D) represents animal survival.
Figure 6:
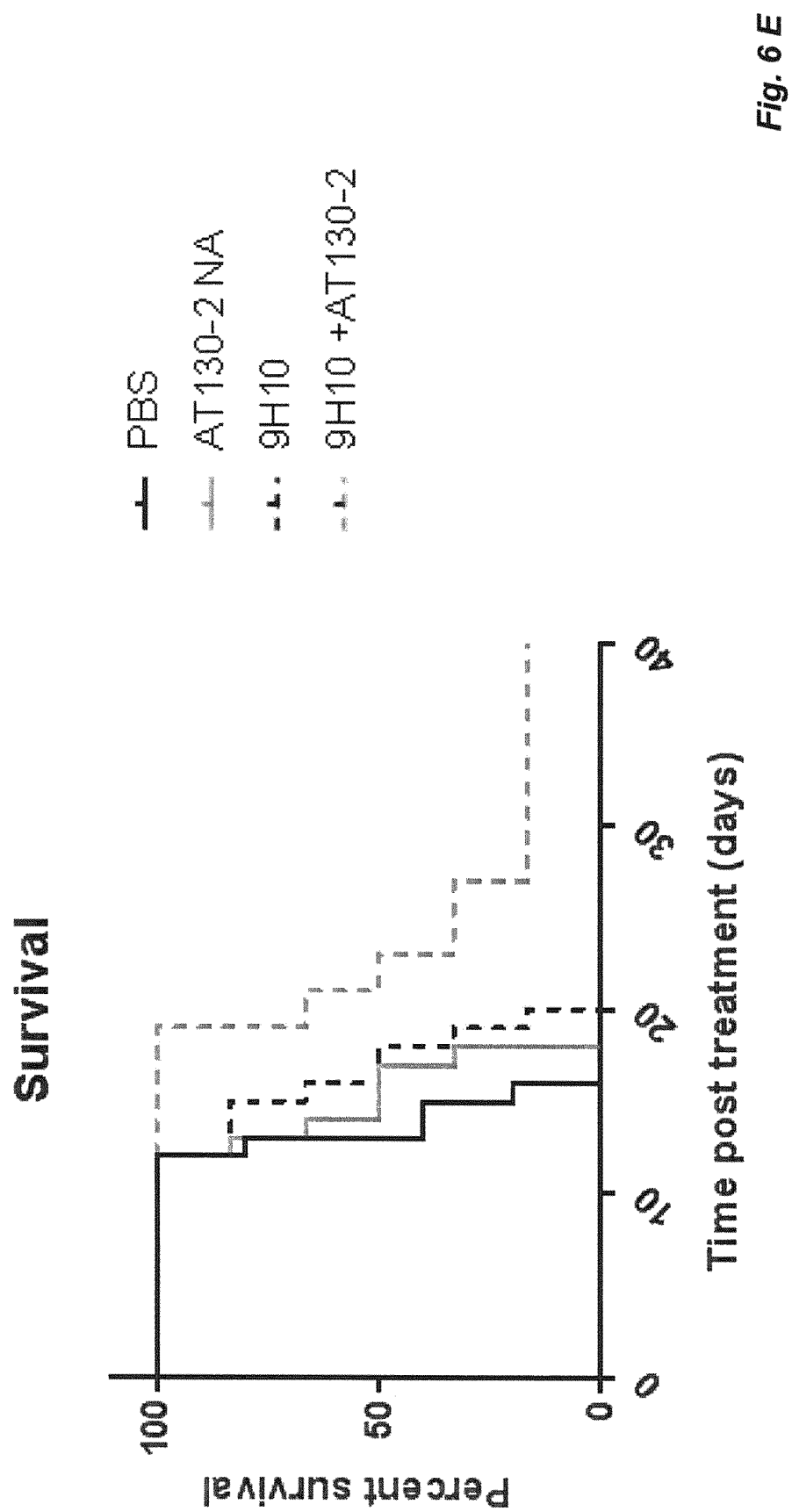
Figure 7:
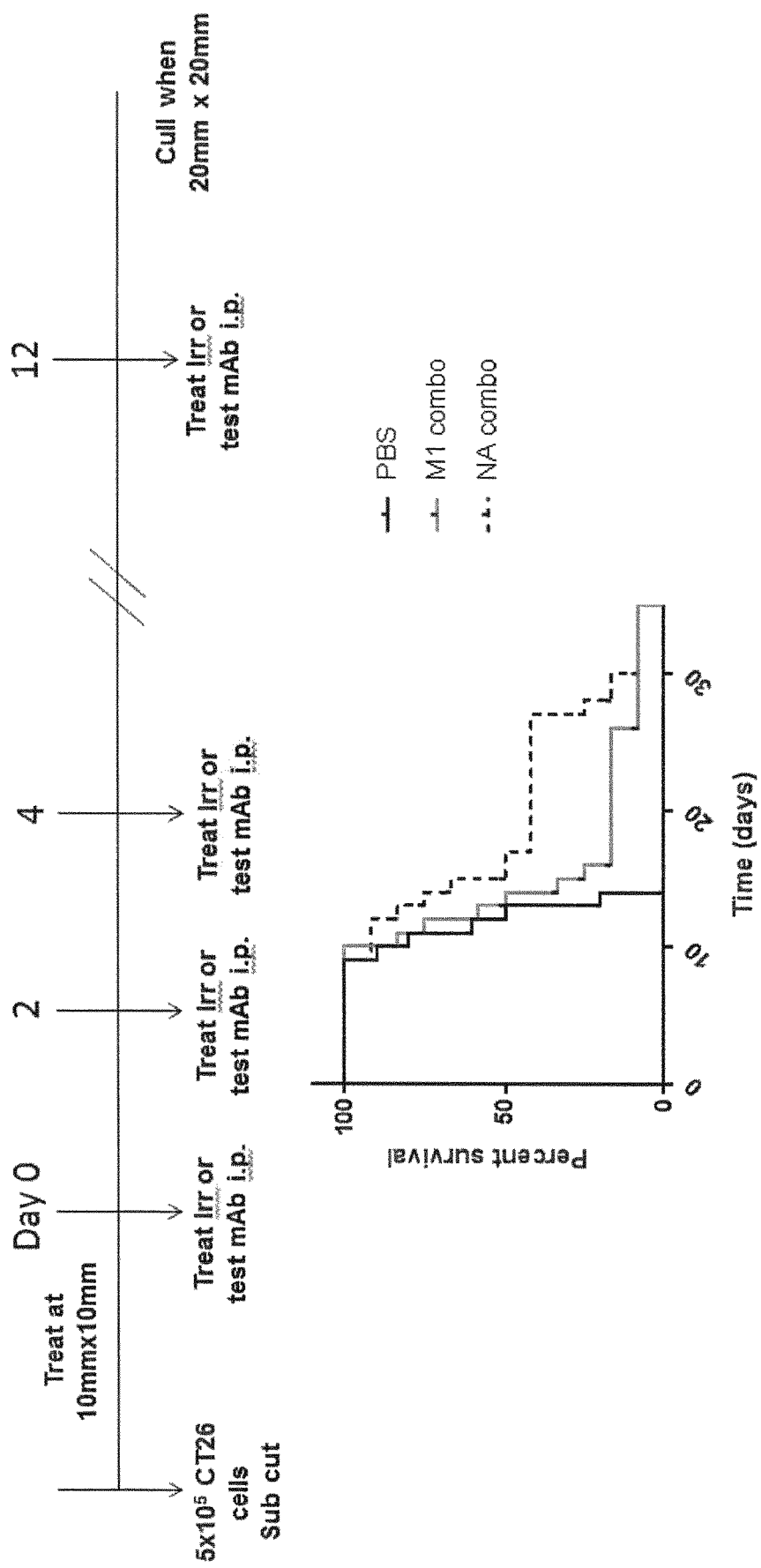
FIG. 7 illustrates combination therapy of anti-CTLA-4 and FcγRIIB blockade comparing WT (denoted M1 combo) and Fc-inert (denoted NA combo) AT130-2 mAb. 5×105 CT26 cells injected S.0 into female BALB/c mice. Mice were randomised into treatment groups when tumour width x length was approximately 100 mm$^2$. Treatment was performed on days 0, 2, 4 and 11. On day 0 combination mice received 100 μg AT130-2 N297A or AT130-2 mIgG1 (anti-mouse CD32) in 200 μl PBS I.P, 6 hours later they received 200 μg 9H10 I.P in 200 μl PBS. On days 2, 4 and 11 combination mice received both antibodies (200 μg 9H10 and 100 μg AT130-2 NA/mIgG1) in a single 200 μl I.P injection. The width and length of tumours was measured and mice were culled when tumour length x width exceeded 400 mm². Data is shown in the survival curve below N=11-12. There was significantly longer survival in the NA combination treated group compared to mice receiving the mIgG1 combination (log-rank test P=0.0460).

Again, this is the same concept as above, but using an antibody to yet another target strongly expressed on tumor-associated Treg cells(CTLA-4), resulting in antitumour immunity. Thus, to address whether this approach might augment anti-cancer immunotherapy we inoculated CT26 cells S.C into female BALB/c mice. Mice were randomised into treatment groups when tumour width x length was approximately 100 mm². Mice received 200 μg 9H10 (hamster anti-mouse CTLA4) antibody LP in 200 μl PBS on days 0, 2, 4 and 11. On day 0 combination mice received 100 μg AT130-2 N297A. The width and length of tumours was measured and mice were culled when tumour length×width exceeded 400 mm² (FIG. 6A). FIG. 6B shows the growth of individual tumours in each group and FIG. 6C representing the median area (+/−SEM or SD). The survival curve for these mice is shown in FIG. 6D with a composite survival curve from a second experiment represented in FIG. 6E where the difference in survival between the NA combination versus 9H10 alone was statistically significant (log-rank test 0.0179). Finally, to address whether this effect was dependent upon the NA format of the antibody the experiment was repeated using WT mIgG1 and compared with the NA format as before. The NA variant was not significantly different than the 9H10 alone group and the NA combination was significantly more effective than the combination with the WT mAb (logrank test P=0.0460) (FIG. 7). This demonstrate that a WT Ab, i.e. a normal, glycosylated mAb, does not combine effectively and instead impairs the desired therapeutic effect.

mAb-mediated FcγRIIB Blockade augments PD-L1 immunotherapy

Figure 8A:
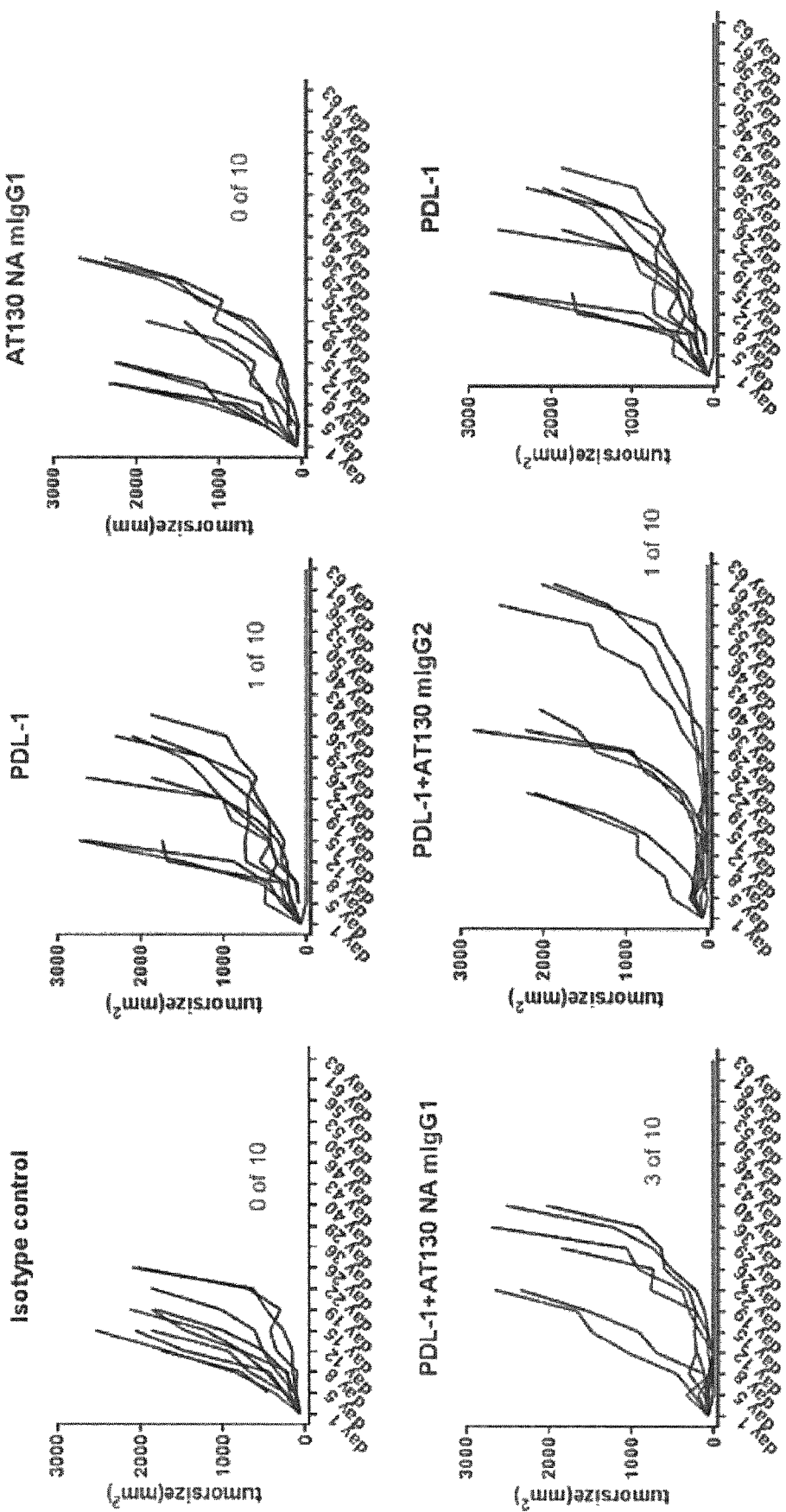
FIG. 8A shows the growth of individual tumours in each group (one graph per group). The number indicates the number of surviving mice in each group.
Figure 8:
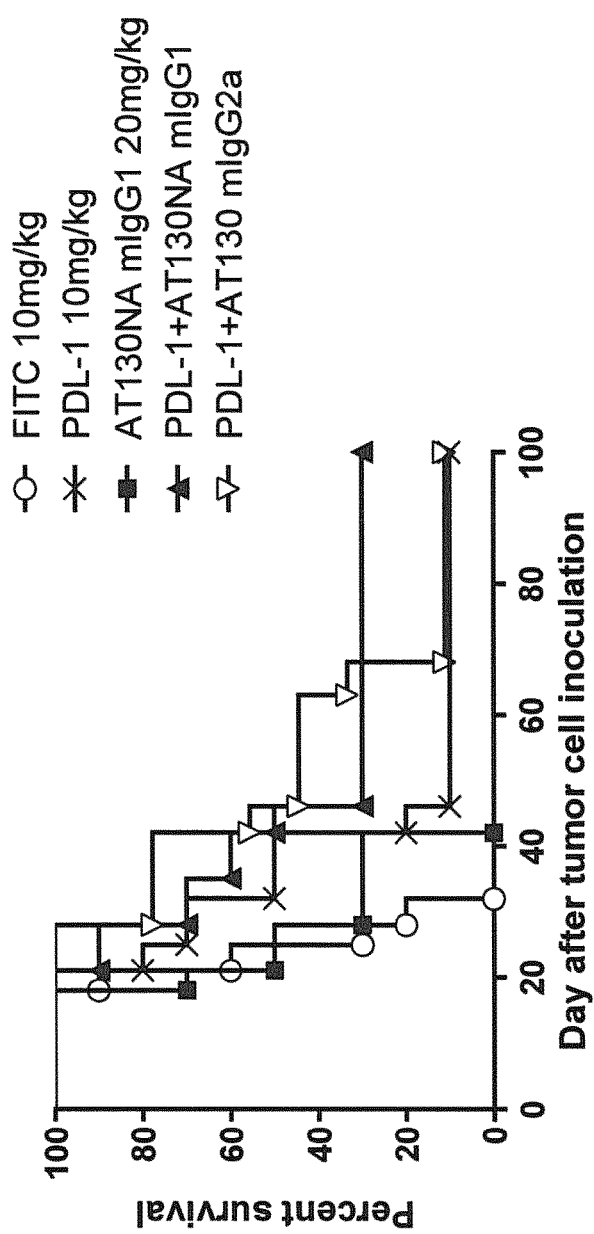
FIG. 8 illustrates combination therapy with anti-PD-L1 and FcγRIIB blockade, and to address whether this effect was dependent upon the NA format of the antibody, the experiment was performed using both WT mIgG1 and the NA format.

As with CTLA4, the effect of antibodies targeting PD-L1 is believed to be dependent on activating FcγRs. However, distinct form CTLA-4, PD-L1 is expressed on a variety of cells, most notably cells of the myeloid lineage and cancer cells. To address whether combining a PD-L1 antibody with FcγRIIB blockade augments anti-cancer immunotherapy, we inoculated MC38 cells S.C into female C57/Bl6 mice. Mice were randomised into treatment groups when tumour width× length was approximately 100 mm². Mice received 10 mg/kg 9H10 (hamster anti-mouse CTLA4) antibody i.p. in 200 μl PBS on days 0, 2, 4 and 11. On day 0 combination mice received 100 μg AT130-2 N297A or WT AT130-2. The width and length of tumours was measured and mice were culled when tumour volume exceeded 2000 mm². FIG. 8A shows the growth of individual tumours in each group. The number indicates the number of surviving mice in each group. FIG. 8B shows the survival curves for the mice. To address whether this effect was dependent upon the NA format of the antibody, the experiment was performed using both WT mIgG1 and the NA format as before. The NA variant was more effective than the combination with the WT mAb and resulted In more mice surviving (FIG. 8B). This demonstrates that the most efficacious combination for PD-L1 antibodies, targeting primarily cancer cells and monocytes/macrophages/myeloid derived suppressor cells, is the aglycosylated NA format.

Together, the above data shows that blockade of FcγRIIB as a mean of enhancing the therapeutic efficacy of other antibodies is broad and applicable for antibodies against various targets (CD20, CD25, CTLA4 and PD-L1) expressed on various cell types (B cells, Treg cells and myeloid cells).

Comparison of WT 6G11 Versus N297A 6G11 Binding to Fc Gamma Receptors (Mouse and Human)

SPR analysis was performed on a Biacore T200 (GE Healthcare). Samples were run at 25° C. in HBS-EP+buffer at 30 mL/min. Data was analyzed with BiaEvaluation software. The response of the blank control flow-cell was automatically subtracted prior to data analysis. For comparison of FcγR binding, 6G11 WT or 6G11 N297Q hIgG1 was immobilized at pH 5 onto a CM5 sensor chip by amine coupling and recombinant human or mouse FcγRs (100 nM) (R&D Systems) were injected across both surfaces for 180 s. Alternatively a range of concentrations of FcγR were added (0-500 nM) sequentially and the responses measured. The results are shown in FIG. 10A-H.

The invention claimed is:

1. A method for treatment of an FcγRIIb-negative cancer in a patient, the method comprising:
   (a) identifying a patient who is determined to have a cancer that is FcγRIIb negative, and
   (b) administering to the patient:
      (i) a first antibody molecule that specifically binds FcγRIIb via its Fab region and that lacks Fc region or has reduced binding to Fcγ receptors via its Fc region, and
      (ii) a second antibody molecule that specifically binds to a receptor present on an immune cell, wherein the immune cell is an immune cell that suppresses anti-cancer immunity, which second antibody molecule has an Fc region that is capable of activating at least one activating Fcγ receptor, and wherein the binding of the second antibody to the receptor on the immune cell causes depletion and/or deactivation of the immune cell.

2. The method according to claim 1, wherein the first antibody lacks an Fc region.

3. The method according to claim 1, wherein the immune cell that suppresses anti-cancer immunity is a regulatory T cell (Treg), a myeloid cell, or both.

4. The method according to claim 3, wherein the myeloid cell is a tumour-associated macrophage and/or the FcγRIIb-negative cancer is a solid cancer selected from the group consisting of: a carcinoma; a sarcoma; and a lymphoma; or more specifically from the group consisting of: melanoma, breast cancer, prostate cancer, colorectal cancer, lung cancer, bladder cancer, kidney cancer, mesothelioma, Merkel cell carcinoma, and head and neck cancer.

5. The method according to claim 1, wherein the first antibody molecule is selected from the group consisting of a human antibody molecule, a humanized antibody molecule, and an originally human antibody that has been modified, and wherein the first antibody molecule is further selected from the group consisting of: a full-length antibody, a chimeric antibody, a single chain antibody, a Fab fragment, a (Fab')₂ fragment, a Fab' fragment a Fv fragment, and an scFv fragment.

6. The method according to claim 1, wherein the first antibody molecule is a monoclonal antibody molecule, and wherein the first antibody molecule is a human IgG antibody molecule having an aglycosylated Fc region or an IgG antibody molecule of human origin having an aglycosylated Fc region.

7. The method according to claim 6, wherein the IgG antibody molecule is an IgG1 or IgG2 antibody molecule.

8. The method according to claim 7, wherein the IgG antibody molecule is an aglycosylated human IgG1 or an aglycosylated humanized murine antibody or an aglycosylated humanized lama hcIgG antibody or an aglycosylated chimerized murine IgG, wherein the IgG antibody molecule has been aglycosylated through amino acid substitution in position 297.

9. The method according to claim 8, wherein the IgG antibody molecule has been aglycosylated through an N297Q substitution.

10. The method according to claim 1, wherein the first antibody molecule comprises a variable heavy chain (VH) and variable light chain (VL) comprising the following CDR amino acid sequences:
   (i) the VH comprising SEQ ID NO: 51 and SEQ ID NO: 52 and SEQ ID NO: 53 and the VL comprising SEQ ID NO: 54 and SEQ ID NO: 55 and SEQ ID NO: 56; or
   (ii) the VH comprising SEQ ID NO: 57 and SEQ ID NO: 58 and SEQ ID NO: 59 and the VL comprising SEQ ID NO: 60 and SEQ ID NO: 61 and SEQ ID NO: 62; or
   (iii) the VH comprising SEQ ID NO: 63 and SEQ ID NO: 64 and SEQ ID NO: 65 and the VL comprising SEQ ID NO: 66 and SEQ ID NO: 67 and SEQ ID NO: 68; or
   (iv) the VH comprising SEQ ID NO: 69 and SEQ ID NO: 70 and SEQ ID NO: 71 and the VL comprising SEQ ID NO: 72 and SEQ ID NO: 73 and SEQ ID NO: 74; or
   (v) the VH comprising SEQ ID NO: 75 and SEQ ID NO: 76 and SEQ ID NO: 77 and the VL comprising SEQ ID NO: 78 and SEQ ID NO: 79 and SEQ ID NO: 80; or
   (vi) the VH comprising SEQ ID NO: 81 and SEQ ID NO: 82 and SEQ ID NO: 83 and the VL comprising SEQ ID NO: 84 and SEQ ID NO: 85 and SEQ ID NO: 86; or
   (vii) the VH comprising SEQ ID NO: 87 and SEQ ID NO: 88 and SEQ ID NO: 89 and the VL comprising SEQ ID NO: 90 and SEQ ID NO: 91 and SEQ ID NO: 92; or
   (viii) the VH comprising SEQ ID NO: 93 and SEQ ID NO: 94 and SEQ ID NO: 95 and the VL comprising SEQ ID NO: 96 and SEQ ID NO: 97 and SEQ ID NO: 98; or
   (ix) the VH comprising SEQ ID NO: 99 and SEQ ID NO: 100 and SEQ ID NO: 101 and the VL comprising SEQ ID NO: 102 and SEQ ID NO: 103 and SEQ ID NO: 104; or
   (x) the VH comprising SEQ ID NO: 105 and SEQ ID NO: 106 and SEQ ID NO: 107 and the VL comprising SEQ ID NO: 108 and SEQ ID NO: 109 and SEQ ID NO: 110; or
   (xi) the VH comprising SEQ ID NO: 111 and SEQ ID NO: 112 and SEQ ID NO: 113 and the VL comprising SEQ ID NO: 114 and SEQ ID NO: 115 and SEQ ID NO: 116; or
   (xii) the VH comprising SEQ ID NO: 117 and SEQ ID NO: 118 and SEQ ID NO: 119 and the VL comprising SEQ ID NO: 120 and SEQ ID NO: 121 and SEQ ID NO: 122; or
   (xiii) the VH comprising SEQ ID NO: 123 and SEQ ID NO: 124 and SEQ ID NO: 125 and the VL comprising SEQ ID NO: 126 and SEQ ID NO: 127 and SEQ ID NO: 128; or
   (xiv) the VH comprising SEQ ID NO: 129 and SEQ ID NO: 130 and SEQ ID NO: 131 and the VL comprising SEQ ID NO: 132 and SEQ ID NO: 133 and SEQ ID NO: 134; or
   (xv) the VH comprising SEQ ID NO: 135 and SEQ ID NO: 136 and SEQ ID NO: 137 and SEQ ID NO: 138 and SEQ ID NO: 139 and SEQ ID NO: 140; or
   (xvi) the VH comprising SEQ ID NO: 141 and SEQ ID NO: 142 and SEQ ID NO: 143 and the VL comprising SEQ ID NO: 144 and SEQ ID NO: 145 and SEQ ID NO: 146; or
   (xvii) the VH comprising SEQ ID NO: 147 and SEQ ID NO: 148 and SEQ ID NO: 149 and the VL comprising SEQ ID NO: 150 and SEQ ID NO: 151 and SEQ ID NO: 152; or
   (xviii) the VH comprising SEQ ID NO: 153 and SEQ ID NO: 154 and SEQ ID NO: 155 and the VL comprising SEQ ID NO: 156 and SEQ ID NO: 157and SEQ ID NO: 158; or
   (xix) the VH comprising SEQ ID NO: 159 and SEQ ID NO: 160 and SEQ ID NO: 161 and the VL comprising SEQ ID NO: 162 and SEQ ID NO: 163 and SEQ ID NO: 164; or
   (xx) the VH comprising SEQ ID NO: 165 and SEQ ID NO: 166 and SEQ ID NO: 167 and the VL comprising SEQ ID NO: 168 and SEQ ID NO: 169 and SEQ ID NO: 170; or
   (xxi) the VH comprising SEQ ID NO: 171 and SEQ ID NO: 172 and SEQ ID NO: 173and the VL comprising SEQ ID NO: 174 and SEQ ID NO: 175 and SEQ ID NO: 176; or
   (xxii) the VH comprising SEQ ID NO: 177 and SEQ ID NO: 178 and SEQ ID NO: 179 and the VL comprising SEQ ID NO: 180 and SEQ ID NO: 181 and SEQ ID NO: 182; or
   (xxiii) the VH comprising SEQ ID NO: 183 and SEQ ID NO: 184 and SEQ ID NO: 185 and the VL comprising SEQ ID NO: 186 and SEQ ID NO: 187 and SEQ ID NO: 188; or
   (xxiv) the VH comprising SEQ ID NO: 189 and SEQ ID NO: 190 and SEQ ID NO: 191 and the VL comprising SEQ ID NO: 192 and SEQ ID NO: 193 and SEQ ID NO: 194.

11. The method according to claim 1, wherein the first antibody molecule comprises a variable heavy chain (VH) and variable light chain (VL) comprising the following amino acid sequences:
   (i) the VH comprising SEQ ID NO: 3 and the VL comprising SEQ ID NO: 27; or
   (ii) the VH comprising SEQ ID NO: 4 and the VL comprising SEQ ID NO: 28; or
   (iii) the VH comprising SEQ ID NO: 5 and the VL comprising SEQ ID NO: 29; or
   (iv) the VH comprising SEQ ID NO: 6 and the VL comprising SEQ ID NO: 30; or
   (v) the VH comprising SEQ ID NO: 7 and the VL comprising SEQ ID NO: 31; or
   (vi) the VH comprising SEQ ID NO: 8 and the VL comprising SEQ ID NO: 32; or
   (vii) the VH comprising SEQ ID NO: 9 and the VL comprising SEQ ID NO: 33; or
   (viii) the VH comprising SEQ ID NO: 10 and the VL comprising SEQ ID NO: 34; or
   (ix) the VH comprising SEQ ID NO: 11 and the VL comprising SEQ ID NO: 35; or
   (x) the VH comprising SEQ ID NO: 12 and the VL comprising SEQ ID NO: 36; or (xi) the VH comprising SEQ ID NO: 13 and the VL comprising SEQ ID NO: 37; or
(xii) the VH comprising SEQ ID NO: 14 and the VL comprising SEQ ID NO: 38; or
(xiii) the VH comprising SEQ ID NO: 15 and the VL comprising SEQ ID NO: 39; or
(xiv) the VH comprising SEQ ID NO: 16 and the VL comprising SEQ ID NO: 40; or
(xv) the VH comprising SEQ ID NO: 17 and the VL comprising SEQ ID NO: 41; or
(xvi) the VH comprising SEQ ID NO: 18 and the VL comprising SEQ ID NO: 42; or
(xvii) the VH comprising SEQ ID NO: 19 and the VL comprising SEQ ID NO: 43; or
(xviii) the VH comprising SEQ ID NO: 20 and the VL comprising SEQ ID NO: 44; or
(xix) the VH comprising SEQ ID NO: 21 and the VL comprising SEQ ID NO: 45; or
(xx) the VH comprising SEQ ID NO: 22 and the VL comprising SEQ ID NO: 46; or
(xxi) the VH comprising SEQ ID NO: 23 and the VL comprising SEQ ID NO: 47; or
(xxii) the VH comprising SEQ ID NO: 24 and the VL comprising SEQ ID NO: 48; or
(xxiii) the VH comprising SEQ ID NO: 25 and the VL comprising SEQ ID NO: 49; or
(xxiv) the VH comprising SEQ ID NO: 26 and the VL comprising SEQ ID NO: 50.

12. The method according to claim 1, wherein the second antibody molecule is selected from the group consisting of a human antibody molecule, a humanized antibody molecule and an originally human antibody that has been modified.

13. The method according to claim 1, wherein the second antibody molecule is a human IgG antibody that specifically binds to a receptor selected from the group consisting of: CTLA-4; 4-1BB; OX40; TNFR2; PD-L1; IL-2R; and GITR.

14. The method according to claim 13, wherein second antibody molecule specifically binds to CTLA-4 or PD-L1.

15. A method for treatment of an FcγRIIb-negative cancer in a patient, the method comprising:
(a) identifying a patient who is determined to have, a cancer that is FcγRIIb negative, and
(b) administering to the patient:
(i) a first antibody molecule that comprises: a variable heavy chain (VH) comprising SEQ ID NO: 171 and SEQ ID NO: 172 and SEQ ID NO: 173; and a variable light chain (VL) comprising SEQ ID NO: 174 and SEQ ID NO: 175 and SEQ ID NO: 176; and
(ii) a second antibody molecule that is an anti-CTLA-4 antibody.

16. The method of claim 15, wherein the first antibody molecule and the second antibody molecule are administered to the patient in two separate compositions.

* * * * *